(12) United States Patent
Mu et al.

(10) Patent No.: US 8,133,905 B2
(45) Date of Patent: Mar. 13, 2012

(54) BIPHENYL COMPOUNDS USEFUL AS MUSCARINIC RECEPTOR ANTAGONISTS

(75) Inventors: YongQi Mu, Los Altos, CA (US); YuHua Ji, Redwood City, CA (US); Mathai Mammen, Menlo Park, CA (US); Viengkham Malathong, Irvine, CA (US)

(73) Assignee: Theravance, Inc., South San Francisco, CA (US)

( * ) Notice: Subject to any disclaimer, the term of this patent is extended or adjusted under 35 U.S.C. 154(b) by 141 days.

(21) Appl. No.: 12/640,869

(22) Filed: Dec. 17, 2009

(65) Prior Publication Data
US 2010/0093753 A1 Apr. 15, 2010

Related U.S. Application Data

(62) Division of application No. 11/371,603, filed on Mar. 9, 2006, now Pat. No. 7,659,403.

(60) Provisional application No. 60/660,435, filed on Mar. 10, 2005.

(51) Int. Cl.
A61K 31/45 (2006.01)
A61K 31/454 (2006.01)
A61K 31/4545 (2006.01)
C07D 401/10 (2006.01)
C07D 295/08 (2006.01)

(52) U.S. Cl. ........ 514/326; 514/290; 546/184; 546/207; 546/208; 546/209

(58) Field of Classification Search ................. 546/184, 546/207, 208, 209; 514/326, 290
See application file for complete search history.

(56) References Cited

U.S. PATENT DOCUMENTS

| | | | |
|---|---|---|---|
| 6,617,325 B1 | 9/2003 | Lehman-Lintz et al. |
| 6,635,764 B2 | 10/2003 | Mammen et al. |
| 6,656,694 B2 | 12/2003 | Mammen |
| 6,693,202 B1 | 2/2004 | Aggen et al. |
| 7,141,671 B2 | 11/2006 | Mammen et al. |
| 7,238,709 B2 | 7/2007 | Mammen et al. |
| 7,262,205 B2 | 8/2007 | Mammen et al. |
| 7,265,133 B2 | 9/2007 | Mammen et al. |
| 7,288,657 B2 | 10/2007 | Mammen et al. |
| 7,345,060 B2 | 3/2008 | Mammen et al. |
| 7,456,199 B2 | 11/2008 | Mammen et al. |
| 7,479,562 B2 | 1/2009 | Ji et al. |
| 7,491,736 B2 | 2/2009 | Mammen et al. |
| 7,501,442 B2 | 3/2009 | Mammen et al. |
| 7,521,041 B2 | 4/2009 | Mammen et al. |
| 7,524,962 B2 | 4/2009 | Mammen et al. |
| 7,550,595 B2 | 6/2009 | Mammen et al. |
| 7,560,469 B2 | 7/2009 | Mammen et al. |
| 7,569,588 B2 | 8/2009 | Mammen et al. |
| 7,585,879 B2 | 9/2009 | Mammen et al. |
| 2003/0018019 A1 | 1/2003 | Meade et al. |
| 2004/0209860 A1 | 10/2004 | Mammen et al. |
| 2004/0209915 A1 | 10/2004 | Mammen et al. |
| 2006/0205775 A1 | 9/2006 | Ji et al. |
| 2006/0205777 A1 | 9/2006 | Mu et al. |
| 2006/0205778 A1 | 9/2006 | Mu et al. |
| 2006/0205779 A1 | 9/2006 | Mu et al. |
| 2006/0281740 A1 | 12/2006 | Ji et al. |
| 2007/0293461 A1 | 12/2007 | Mammen et al. |
| 2008/0071088 A1 | 3/2008 | Mammen et al. |
| 2009/0018165 A1 | 1/2009 | Mammen et al. |
| 2009/0076026 A1 | 3/2009 | Ji et al. |
| 2009/0082397 A1 | 3/2009 | Mammen et al. |
| 2009/0088453 A1 | 4/2009 | Mammen et al. |
| 2009/0226379 A1 | 9/2009 | Mammen et al. |

FOREIGN PATENT DOCUMENTS

| | | |
|---|---|---|
| EP | 0 747 355 A1 | 12/1996 |
| WO | WO 95/06635 A1 | 3/1995 |
| WO | WO 99/64043 A1 | 12/1999 |
| WO | WO 02/051841 A1 | 7/2002 |
| WO | WO 2004/012684 A2 | 2/2004 |

OTHER PUBLICATIONS

Broadley et al., "Muscarinic Receptor Agonists and Antagonists", Molecules, 6, pp. 142-193 (2001).
Dorwald F. A., "Side Reactions in Organic Synthesis", 2005, Wiley: VCH, Weinheim p. IX of Preface.
Eglen et al., "Muscarinic Receptor Subtypes:Pharmacology and Therapeutic Potential", DN&P, 10(8), pp. 462-469 (1997).
Zlotos et al., "Muscarinic receptor agonists and antagonists", Exp. Opin. Ther. Patents, 9(8), pp. 1029-1053 (1999). Naito et al., "Selective Muscarinic Antagonist. II.[1]) Synthesis and Antimuscarinic Properties of Biphenylylcarbamate Derivatives", Chem. Pharm. Bull., vol. 46, No. 8, pp. 1286-1294 (1998).

*Primary Examiner* — Rita Desai
(74) *Attorney, Agent, or Firm* — Jeffrey A. Hagenah; Shelley Eberle

(57) ABSTRACT

The invention provides compounds of formula I:

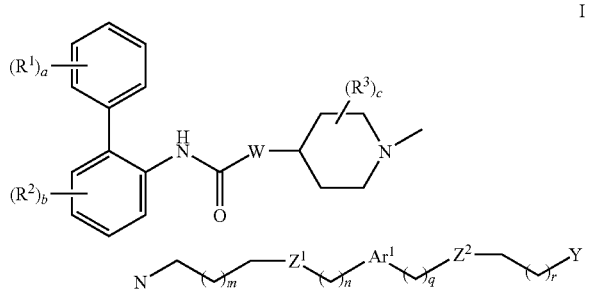

wherein a, b, c, m, n, q, r, W, $Z^1$, $Ar^1$, $Z^2$, Y, $R^1$, $R^2$, and $R^3$ are as defined in the specification. The compounds of formula I are muscarinic receptor antagonists. The invention also provides pharmaceutical compositions containing such compounds, processes and intermediates for preparing such compounds and methods of using such compounds to treat pulmonary disorders.

20 Claims, 6 Drawing Sheets

BIPHENYL COMPOUNDS USEFUL AS MUSCARINIC RECEPTOR ANTAGONISTS

CROSS-REFERENCE TO RELATED APPLICATIONS

This application is a divisional application of U.S. Ser. No. 11/371,603, filed Mar. 9, 2006, now allowed, which claims the benefit of U.S. Provisional Application No. 60/660,435, filed on Mar. 10, 2005; the entire disclosures of which are incorporated herein by reference.

BACKGROUND OF THE INVENTION

1. Field of the Invention

The present invention relates to novel biphenyl compounds having muscarinic receptor antagonist or anticholinergic activity. The invention also relates to pharmaceutical compositions comprising such biphenyl compounds, processes and intermediates for preparing such biphenyl compounds and methods of using such biphenyl compounds to treat pulmonary disorders.

2. State of the Art

Pulmonary or respiratory disorders, such as chronic obstructive pulmonary disease (COPD) and asthma, afflict many millions of people worldwide and such disorders are a leading cause of morbidity and mortality.

Muscarinic receptor antagonists are known to provide bronchoprotective effects and therefore, such compounds are useful for treating respiratory disorders such as COPD and asthma. When used to treat such disorders, muscarinic receptor antagonists are typically administered by inhalation. However, even when administered by inhalation, a significant amount of the muscarinic receptor antagonist is often absorbed into the systemic circulation resulting in systemic side effects such as dry mouth, mydriasis and cardiovascular side effects.

Additionally, many inhaled muscarinic receptor antagonists have a relatively short duration of action requiring that they be administered several times per day. Such a multiple-daily dosing regime is not only inconvenient but also creates a significant risk of inadequate treatment due to patient non-compliance with the required frequent dosing schedule.

Accordingly, a need exists for new muscarinic receptor antagonists. In particular, a need exists for new muscarinic receptor antagonists that having high potency and reduced systemic side effects when administered by inhalation. Additionally, a need exists for inhaled muscarinic receptor antagonists having a long duration of action thereby allowing for once-daily or even once-weekly dosing. Such compounds are expected to be particularly effective for treating pulmonary disorders, such as COPD and asthma, while reducing or eliminating side effects such as dry-mouth and constipation.

SUMMARY OF THE INVENTION

The present invention provides novel biphenyl compounds having muscarinic receptor antagonist or anticholinergic activity. Among other properties, compounds of the invention are expected to possess high potency and reduced systemic side effects when administered by inhalation and to have a long duration of action.

One aspect of the invention relates to a compound of formula I:

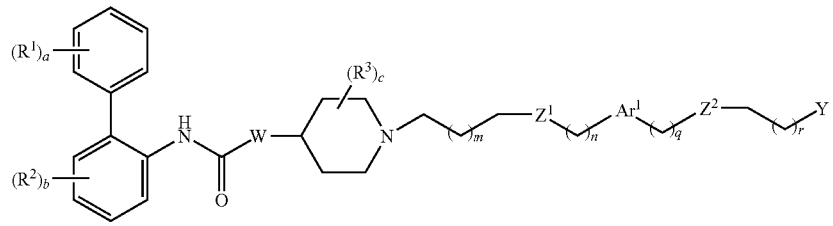

I wherein:
a is 0 or an integer of from 1 to 5;
each $R^1$ is independently selected from (1-4C)alkyl, (2-4C)alkenyl, (2-4C)alkynyl, (3-6C)cycloalkyl, cyano, halo, $-OR^{1a}$, $-C(O)OR^{1b}$, $-SR^{1c}$, $-S(O)R^{1d}$, $-S(O)_2R^{1e}$, $-NR^{1f}R^{1g}$, $-NR^{1h}S(O)_2R^{1i}$, and $-NR^{1j}C(O)R^{1k}$; where each of $R^{1a}$, $R^{1b}$, $R^{1c}$, $R^{1d}$, $R^{1e}$, $R^{1f}$, $R^{1g}$, $R^{1h}$, $R^{1i}$, $R^{1j}$, and $R^{1k}$ is independently hydrogen, (1-4C)alkyl or phenyl(1-4C)alkyl;
b is 0 or an integer of from 1 to 4;
each $R^2$ is independently selected from (1-4C)alkyl, (2-4C)alkenyl, (2-4C)alkynyl, (3-6C)cycloalkyl, cyano, halo, $-OR^{2a}$, $-C(O)OR^{2b}$, $-SR^{2c}$, $-S(O)R^{2d}$, $-S(O)_2R^{2e}$, $-NR^{2f}R^{2g}$, $-NR^{2h}S(O)_2R^{2i}$, and $-NR^{2j}C(O)R^{2k}$; where each of $R^{2a}$, $R^{2b}$, $R^{2c}$, $R^{2d}$, $R^{2e}$, $R^{2f}$, $R^{2g}$, $R^{2h}$, $R^{2i}$, $R^{2j}$, and $R^{2k}$ is independently hydrogen, (1-4C)alkyl or phenyl(1-4C)alkyl;
W represents O or $NW^a$, where $W^a$ is hydrogen or (1-4C)alkyl;
c is 0 or an integer from 1 to 5;
each $R^3$ independently represents (1-4C)alkyl or two $R^3$ groups are joined to form (1-3C)alkylene, (2-3C)alkenylene or oxiran-2,3-diyl;
m is 0 or 1;
$Z^1$ is selected from $-C(O)N(R^4)-$ and $-N(R^4)C(O)-$, where $R^4$ is selected from hydrogen, (1-4C)alkyl, and (3-4C)cycloalkyl;
n is 0 or 1;
$Ar^1$ represents a phenylene group or a (3-5C)heteroarylene group containing 1 or 2 heteroatoms independently selected from oxygen, nitrogen or sulfur; wherein the phenylene or heteroarylene group is substituted with $(R^5)_p$ where p is 0 or an integer from 1 to 4 and each $R^5$ is independently selected from halo, hydroxy, (1-4C)alkyl or (1-4C)alkoxy;
q is 0 or 1;
$Z^2$ is selected from $-C(O)N(R^6)-$ and $-N(R^6)C(O)-$, where $R^6$ is selected from hydrogen, (1-4C)alkyl, and (3-4C)cycloalkyl;
r is 0, 1 or 2;

Y is selected from

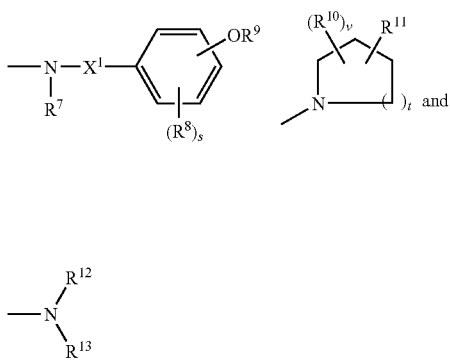

where:

R⁷ is selected from hydrogen, (1-4C)alkyl, (3-4C)cycloalkyl, —C(O)(1-4C)alkyl, -(1-4C)alkyleneC(O)OR$^{7a}$, —C(O)heterocyclyl, —C(O)CH(NH₂)(1-4C)alkyleneQ, -(1-4C)alkyleneC(O)Q', —C(O)(1-4C)alkyleneQ', and —S(O)₂(1-4C)alkyleneQ'; where Q is a nitrogen-containing substituent selected from —NR$^{7b}$R$^{7c}$ and heteroaryl; Q' is a nitrogen-containing substituent selected from —NR$^{7d}$R$^{7e}$ and heterocyclyl; R$^{7a}$ is hydrogen or (1-4C)alkyl; each of R$^{7b}$, R$^{7c}$, R$^{7d}$ and R$^{7e}$ independently represents hydrogen, (1-4C)alkyl, (3-6C)cycloalkyl or hydroxyphenyl, and where (1-4C)alkyl is unsubstituted or substituted by 1 or 2 substituents independently selected from amido, cyano, furyl, hydroxyl, and methylimidazolyl; the heterocyclyl contains 1 or 2 nitrogen atoms, and is unsubstituted or substituted by 1 or 2 substituents independently selected from hydroxyl, amido, (1-4C)alkoxy, oxo, —S(O)₂(1-4C)alkyl, —(CH₂)O(1-4C)alkyl, -(1-4C)alkyleneOH, —NR$^{7f}$R$^{7g}$ and —C(O)NR$^{7h}$R$^{7i}$, where each of R$^{7f}$, R$^{7g}$ R$^{7h}$ and R$^{7i}$ independently represents hydrogen or (1-4C)alkyl; and the heteroaryl contains 1 or 2 nitrogen atoms;

X¹ is selected from (1-3C)alkylene, —C(O)(1-3C)alkylene, (1-3C)alkyleneC(O)—, —SO₂—, —SO₂(1-3C)alkylene and (1-3C)alkyleneSO₂—; where the alkylene group in any X¹ is optionally substituted with 1 or 2 substituents independently selected from (1-4C)alkyl and —NR$^{Xa}$R$^{Xb}$;

wherein R$^{Xa}$ and R$^{Xb}$ are independently selected from hydrogen and (1-4alkyl);

s is 0, 1 or 2;

each R⁸ independently represents (1-4C)alkyl, (2-4C)alkenyl, (2-4C)alkynyl, (3-6C)cycloalkyl, cyano, nitro, halo, N,N-di(1-4C)alkylamino(2-4C)alkoxy, —OR$^{8a}$, —C(O)OR$^{8b}$, —SR$^{8c}$, —S(O)R$^{8d}$, —S(O)₂R$^{8e}$ or —NR$^{8f}$R$^{8g}$; each of R$^{8a}$, R$^{8b}$, R$^{8c}$, R$^{8d}$, R$^{8e}$, R$^{8f}$ and R$^{8g}$ is independently hydrogen, (1-4C)alkyl, (3-6C)cycloalkyl, phenyl or phenyl(1-4C)alkyl, wherein each phenyl group is unsubstituted or substituted by 1 or 2 substituents independently selected from halo, (1-4C)alkyl and (1-4C)alkoxy;

R⁹ is selected from hydrogen, (1-4C)alkyl, (1-4C)alkyleneNR$^{9a}$R$^{9b}$, and phenyl, each of R$^{9a}$ and R$^{9b}$ is independently hydrogen or (1-4C)alkyl; or R⁹ is taken together with R⁸ to form a ring having 1 to 2 oxygen atoms, where said ring is unsubstituted or substituted by 1 or 2 (1-4C)alkyl substituents;

t is 0 or an integer from 1 to 3;

v is 0 or an integer from 1 to 4;

each R¹⁰ independently represents fluoro or (1-4C)alkyl;

R¹¹ is selected from hydrogen, —OH, -(1-4C)alkyleneOH, —C(O)NR$^{11a}$R$^{11b}$, and —CH₂C(O)NR$^{11a}$R$^{11b}$, where R$^{11a}$ and R$^{11b}$ are independently selected from hydrogen, (1-4C)alkyl, hydroxy, (1-4C)alkoxy, (1-4C)alkyleneOR$^{11c}$, (3-6C)cycloalkyl, phenyl optionally substituted with hydroxy, and (1-4C)alkyleneC(O)NR$^{11d}$R$^{11e}$, where said (3-6C)cycloalkyl is unsubstituted or substituted with 1 or 2 (1-6C)alkyl or —NR$^{11d}$R$^{11e}$ groups, and where each of R$^{11c}$, R$^{11d}$ and R$^{11e}$ is independently hydrogen or (1-4C)alkyl; or R$^{11a}$ is taken together with R$^{11b}$ to form a 3-7 membered ring, optionally substituted with hydroxyl;

R¹² is selected from hydrogen, (1-4C)alkyl, -(1-4C)alkyleneOH, and -(1-4C)alkyleneheteroaryl; and R¹³ is selected from (1-4C)alkyl, -(1-4C)alkyleneOH, -(1-4C)alkyleneheteroaryl, (3-6C)cycloalkyl, -(1-4C)alkylene(3-6C)cycloalkyl, and -(1-4C)alkyleneC(O)NR$^{13a}$R$^{13b}$, where R$^{13a}$ and R$^{13b}$ are independently hydrogen or (1-4C)alkyl; or R¹² and R¹³ are taken together to form a ring selected from piperazinone, morpholine, and piperazine; and said piperazine is substituted with (R$^{13c}$)$_w$ where w is 0 or an integer from 1 to 3 and each R$^{13c}$ is independently selected from (1-4C)alkyl, phenyl or benzyl, optionally substituted with 1 to 5 fluoro substituents, or two R$^{13c}$ groups are joined to form (1-3C)alkylene;

wherein each alkyl and alkoxy group in R¹, R$^{1a-1k}$, R², R$^{2a-2k}$, R³, R⁵, R⁸R$^{8a-8g}$, R⁹, and R$^{9a-9b}$ is optionally substituted with 1 to 5 fluoro substituents;

or a pharmaceutically acceptable salt or solvate or stereoisomer thereof.

Another aspect of the invention relates to a compound of formula Ia:

Ia

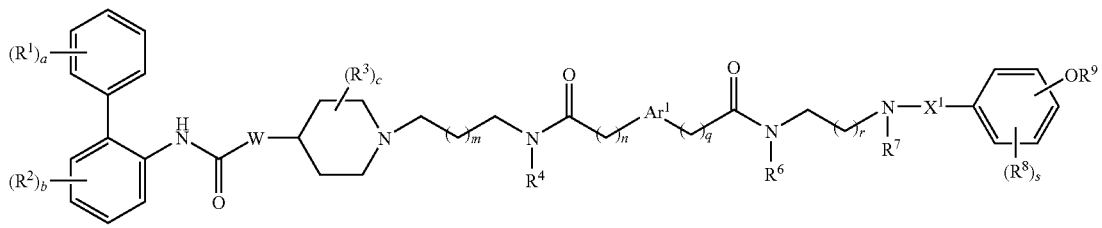

where a, b, c, m, n, q, r, s, W, Ar¹, X¹, R$^{1-4}$ and R$^{6-9}$ are as defined above; or a pharmaceutically acceptable salt or solvate or stereoisomer thereof.

Another aspect of the invention relates to a compound of formula Ia':

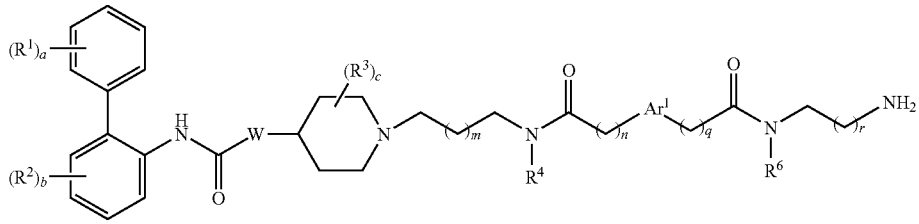

Ia' where a, b, c, m, n, q, r, W, Ar¹, R¹⁻⁴ and R⁶ are as defined above; or a pharmaceutically acceptable salt or solvate or stereoisomer thereof.

Another aspect of the invention relates to a compound of formula Ib:

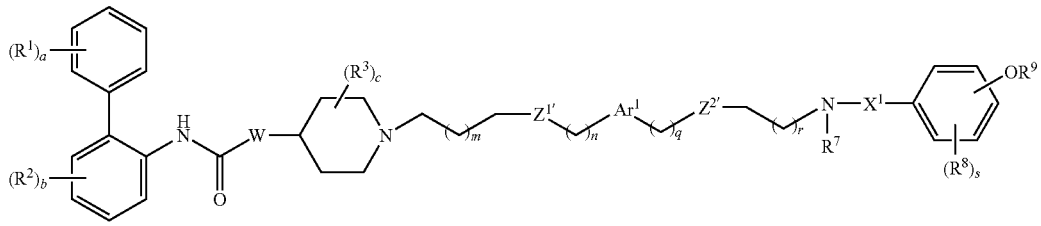

Ib where a, b, c, m, n, q, r, s, W, Ar¹, X¹, R¹⁻³ and R⁷⁻⁹ are as defined above; Z¹' is —C(O)N(R⁴)— and Z²' is selected from —C(O)N(R⁶)— and —N(R⁶)C(O)—; or Z¹' is —N(R⁴)C(O)— and Z²' is —N(R⁶)C(O)—; or a pharmaceutically acceptable salt or solvate or stereoisomer thereof.

Another aspect of the invention relates to a compound of formula Ic:

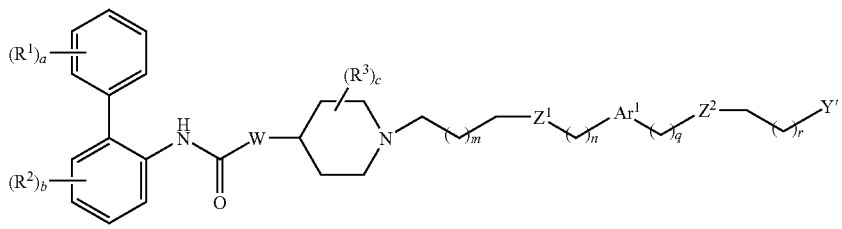

Ic where a, b, c, m, n, q, r, W, Z¹, Ar¹, Z², and R¹⁻³ are as defined above; Y' is selected from

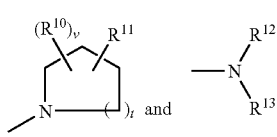

where t, v, and R¹⁰⁻¹³ are as defined above; or a pharmaceutically acceptable salt or solvate or stereoisomer thereof.

Another aspect of the invention pertains to a pharmaceutical composition comprising a pharmaceutically acceptable carrier and a therapeutically effective amount of a compound of the invention or a pharmaceutically acceptable salt or solvate or stereoisomer thereof. Yet another aspect of the invention pertains to compositions comprising a compound of the invention in combination with one or more other therapeutic agents. Accordingly, in one embodiment, the invention is directed to a composition comprising (a) a pharmaceutically acceptable carrier and a therapeutically effective amount of a compound of the invention or a pharmaceutically acceptable salt or solvate or stereoisomer thereof; and (b) a therapeutically effective amount of an agent selected from a steroidal anti-inflammatory agent such as a corticosteroid; a $\beta_2$ adrenergic receptor agonist; a phosphodiesterase-4 inhibitor; or a combination thereof; wherein the compound of the invention and the agent are formulated together or separately. When the agent is formulated separately, a pharmaceutically acceptable carrier may be included.

Compounds of the invention possess muscarinic receptor antagonist activity, and are therefore expected to be useful for treating pulmonary disorders such as chronic obstructive pulmonary disease and asthma.

Yet another aspect of the invention relates to a method for treating a pulmonary disorder, comprising administering to a patient a therapeutically effective amount of a compound of the invention or a pharmaceutically acceptable salt or solvate or stereoisomer thereof. Still another aspect of the invention pertains to a method of producing bronchodilation in a patient, comprising administering to the patient a bronchodilation-producing amount of a compound of the invention or a pharmaceutically acceptable salt or solvate or stereoisomer thereof. In one embodiment, the compound is administered by inhalation. The invention is also directed to a method of treating chronic obstructive pulmonary disease or asthma, comprising administering to a patient a therapeutically effective amount of a compound of the invention or a pharmaceutically acceptable salt or solvate or stereoisomer thereof. Another aspect of the invention relates to a method for antagonizing a muscarinic receptor in a mammal comprising administering to the mammal, a therapeutically effective amount of the compound of the invention.

Since compounds of the invention possess muscarinic receptor antagonist activity, such compounds are also useful as research tools. Accordingly, another aspect of the invention is directed to a method for using a compound of the invention or a pharmaceutically acceptable salt or solvate or stereoisomer thereof as a research tool for studying a biological system or sample, or for discovering new chemical compounds having muscarinic receptor antagonist activity.

The invention is also directed to processes and intermediates useful for preparing compounds of the invention, and pharmaceutically acceptable salts, solvates, and stereoisomers thereof. Accordingly, another aspect of the invention relates to a process of preparing a compound of the invention (formula I, Ia-Ic or Ia'), comprising:

(a) reacting a compound of formula II with a compound of formula III; or
(b) coupling a compound of formula IVa with a compound of formula Va, or coupling a compound of formula IVb with a compound of formula Vb; or
(c) coupling a compound of formula VIa with a compound of formula VIIa, or coupling a compound of formula VIb with a compound of formula VIIb; or
(d) reacting a compound of formula VIII with a compound of formula IX; or
(e) reacting a compound of formula II with a compound of formula X in the presence of a reducing agent; or
(f) reacting a compound of formula XI with a compound of formula IX in the presence of a reducing agent; and then removing any protecting groups that may be present to provide a compound of formula I, Ia-Ic or Ia', and optionally, forming a pharmaceutically acceptable salt thereof, wherein compounds of formula I-XI are as defined herein.

In one embodiment, the above process further comprises the step of forming a pharmaceutically acceptable salt of a compound of formula I, Ia-Ic or Ia'. In other embodiments, the invention is directed to the other processes described herein; and to the product prepared by any of the processes described herein.

The invention is also directed to a compound of the invention or a pharmaceutically acceptable salt or solvate or stereoisomer thereof, for use in therapy or as a medicament.

Additionally, the invention is directed to the use of a compound of the invention or a pharmaceutically acceptable salt or solvate or stereoisomer thereof, for the manufacture of a medicament; especially for the manufacture of a medicament for the treatment of a pulmonary disorder, for antagonizing a muscarinic receptor in a mammal, for producing bronchodilation, or for treating chronic obstructive pulmonary disease or asthma.

BRIEF DESCRIPTION OF THE DRAWINGS

Various aspects of the present invention are illustrated by reference to the accompanying drawings.

DETAILED DESCRIPTION OF THE INVENTION

Figure 1:
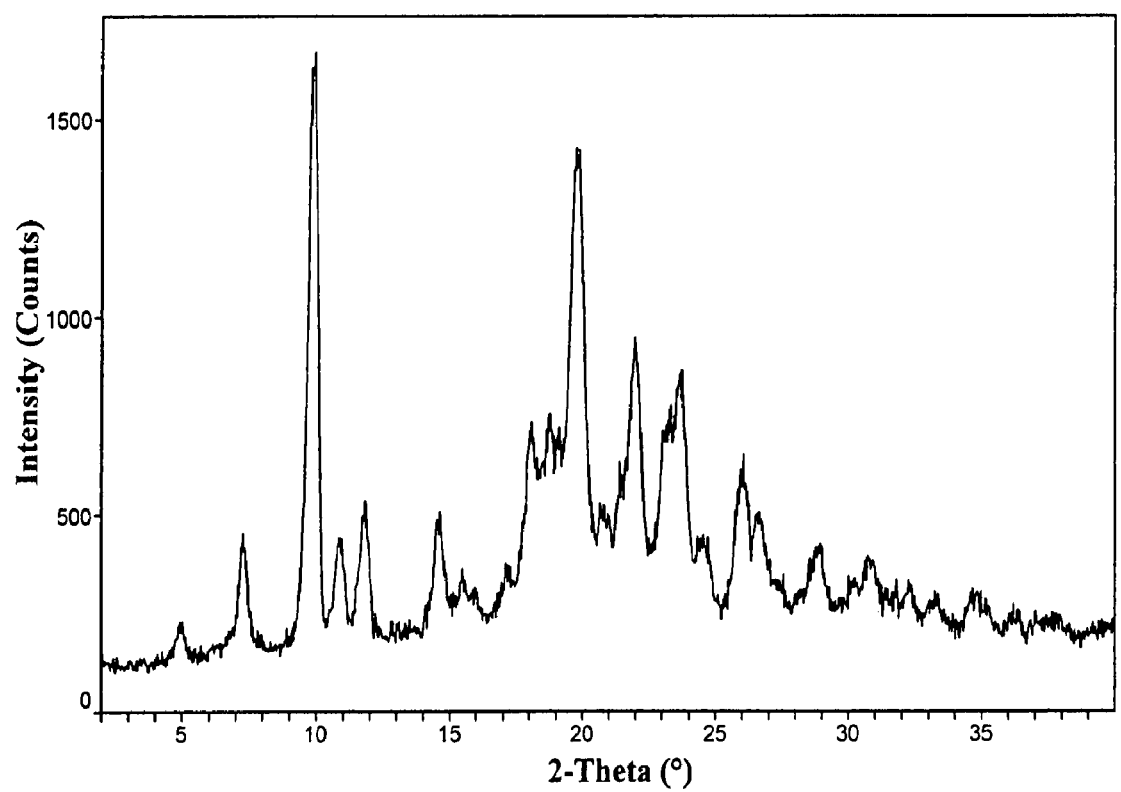
FIG. 1 shows a powder x-ray diffraction (PXRD) pattern of a crystalline diacetate salt of biphenyl-2-ylcarbamic acid 1-[2-({3-[2-(4-hydroxybenzylamino)ethylcarbamoyl]benzoyl}methylamino)ethyl]piperidin-4-yl ester (the compound of Example 1).

The invention is directed to novel biphenyl compounds of formula I, and pharmaceutically acceptable salts, solvates or stereoisomers thereof. Compounds of formula I of particular interest include those compounds having formula Ia, Ib and Ic. The invention is also directed to novel biphenyl compounds of formula Ia', and pharmaceutically acceptable salts, solvates or stereoisomers thereof. Compounds of formula Ia' are useful as intermediates in the synthesis of compounds of formula Ia. Further, compounds of formula Ia' may be metabolites of compounds of formula Ia, and more particularly, may be active metabolites of compounds of formula Ia.

The compounds of the invention may contain one or more chiral centers and therefore, the invention is directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions of the invention unless otherwise indicated, provided that the desired utility of the composition as a whole is not eliminated by the presence of such other isomers.

The compounds of the invention also contain several basic groups (e.g., amino groups) and therefore, can exist as the free base or in various salt forms. All such salt forms are included within the scope of the invention. Furthermore, solvates of compounds of the invention or salts thereof are included within the scope of the invention. Additionally, where applicable, all cis-trans or E/Z isomers (geometric isomers), tautomeric forms and topoisomeric forms of the compounds of the invention are included within the scope of the invention unless otherwise specified.

The compounds of the invention, as well as those compounds used in their synthesis, may also include isotopically-labeled compounds, i.e., where one or more atoms have been enriched with atoms having an atomic mass different from the atomic mass predominately found in nature. Examples of isotopes that may be incorporated into the compounds of the invention include, but are not limited to, $^2$H, $^3$H, $^{13}$C, $^{14}$C, $^{15}$N, $^{18}$O and $^{17}$O.

The nomenclature used herein to name the compounds of the invention is illustrated in the Examples herein. This nomenclature has been derived using the commercially-available AutoNom software (MDL, San Leandro, Calif.). For example, compounds of formulas I, Ia-Ic and Ia', where W is O have typically been named as ester derivatives of biphenyl-2-ylcarbamic acid.

Representative Embodiments

The following substituents and values for compounds of the invention (formulas I, Ia-Ic, and Ia'), are intended to provide representative examples of various aspects and embodiments of the invention. These representative values are intended to further define and illustrate such aspects and embodiments and are not intended to exclude other embodiments or to limit the scope of the invention. In this regard, the representation that a particular value or substituent is preferred is not intended in any way to exclude other values or substituents from the invention unless specifically indicated.

One embodiment of the invention pertains to compounds of formula I, where $Z^1$ is —N($R^4$)C(O)—, $Z^2$ is —C(O)N($R^6$)—, and Y is:

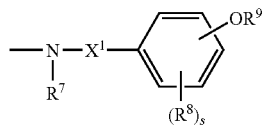

These compounds have the following formula Ia:

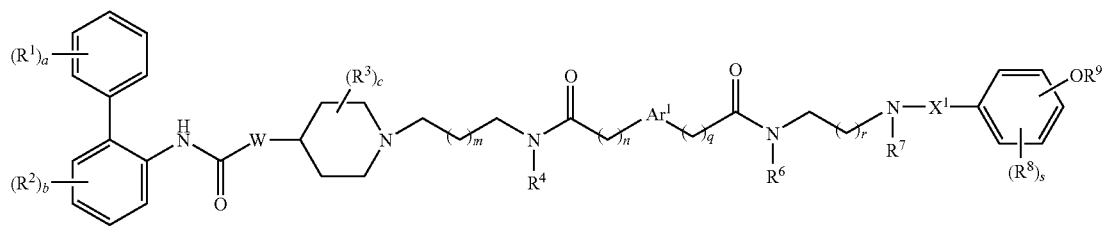

$Ar^1$ represents a phenylene group or a (3-5C)heteroarylene group containing 1 or 2 heteroatoms independently selected from oxygen, nitrogen or sulfur; wherein the phenylene or heteroarylene group is substituted with $(R^5)_p$ where p is 0 or an integer from 1 to 4 and each $R^5$ is independently selected from halo, hydroxy, (1-4C)alkyl or (1-4C)alkoxy;

q is 0 or 1;

$R^6$ is selected from hydrogen, (1-4C)alkyl, and (3-4C)cycloalkyl;

r is 0, 1 or 2;

$R^7$ is selected from hydrogen, (1-4C)alkyl, (3-4C)cycloalkyl, —C(O)(1-4C)alkyl, -(1-4C)alkyleneC(O)$OR^{7a}$, —C(O)heterocyclyl, —C(O)CH($NH_2$)(1-4C)alkyleneQ, -(1-4C)alkyleneC(O)Q', —C(O)(1-4C)alkyleneQ', and —S(O)$_2$(1-4C)alkyleneQ'; where Q is a nitrogen-containing substituent selected from —NR$^{7b}$R$^{7c}$ and heteroaryl; Q' is a nitrogen-containing substituent selected from —NR$^{7d}$R$^{7e}$ and heterocyclyl; $R^{7a}$ is hydrogen or (1-4C)alkyl; each of $R^{7b}$, $R^{7c}$, $R^{7d}$ and $R^{7e}$ independently represents hydrogen, (1-4C)alkyl, (3-6C)cycloalkyl or hydroxyphenyl, and where (1-4C) alkyl is unsubstituted or substituted by 1 or 2 substituents independently selected from amido, cyano, furyl, hydroxyl, and methylimidazolyl; the heterocyclyl contains 1 or 2 nitrogen atoms, and is unsubstituted or substituted by 1 or 2 substituents independently selected from hydroxyl, amido, (1-4C)alkoxy, oxo, —S(O)$_2$(1-4C)alkyl, —(CH$_2$)O(1-4C)alkyl, -(1-4C)alkyleneOH, —NR$^{7f}$R$^{7g}$ and —C(O)NR$^{7h}$R$^{7i}$, Ia wherein:
a is 0 or an integer of from 1 to 5;
each $R^1$ is independently selected from (1-4C)alkyl, (2-4C)alkenyl, (2-4C)alkynyl, (3-6C)cycloalkyl, cyano, halo, —OR$^{1a}$, —C(O)OR$^{1b}$, —SR$^{1c}$, —S(O)R$^{1d}$, —S(O)$_2$R$^{1e}$, —NR$^{1f}$R$^{1g}$, —NR$^{1h}$S(O)$_2$R$^{1i}$, and —NR$^{1j}$C(O)R$^{1k}$; where each of R$^{1a}$, R$^{1b}$, R$^{1c}$, R$^{1d}$, R$^{1e}$, R$^{1f}$, R$^{1g}$, R$^{1h}$, R$^{1i}$, R$^{1j}$, and R$^{1k}$ is independently hydrogen, (1-4C)alkyl or phenyl(1-4C)alkyl;

b is 0 or an integer of from 1 to 4;
each $R^2$ is independently selected from (1-4C)alkyl, (2-4C)alkenyl, (2-4C)alkynyl, (3-6C)cycloalkyl, cyano, halo, —OR$^{2a}$, —C(O)OR$^{2b}$, —SR$^{2c}$, —S(O)R$^{2d}$, —S(O)$_2$R$^{2e}$, —NR$^{2f}$R$^{2g}$, —NR$^{2h}$S(O)$_2$R$^{2i}$, and —NR$^{2j}$C(O)R$^{2k}$; where each of R$^{2a}$, R$^{2b}$, R$^{2c}$, R$^{2d}$, R$^{2e}$, R$^{2f}$, R$^{2g}$, R$^{2h}$, R$^{2i}$, R$^{2j}$, and R$^{2k}$ is independently hydrogen, (1-4C)alkyl or phenyl(1-4C)alkyl;

W represents O or NW$^a$, where W$^a$ is hydrogen or (1-4C)alkyl;
c is 0 or an integer from 1 to 5;
each $R^3$ independently represents (1-4C)alkyl or two $R^3$ groups are joined to form (1-3C)alkylene, (2-3C)alkenylene or oxiran-2,3-diyl;
m is 0 or 1;
$R^4$ is selected from hydrogen, (1-4C)alkyl, and (3-4C)cycloalkyl;
n is 0 or 1;

where each of R$^{7f}$, R$^{7g}$ R$^{7h}$ and R$^{7i}$ independently represents hydrogen or (1-4C)alkyl; and the heteroaryl contains 1 or 2 nitrogen atoms;

$X^1$ is selected from (1-3C)alkylene, —C(O)(1-3C)alkylene, (1-3C)alkyleneC(O)—, —SO$_2$—, —SO$_2$(1-3C)alkylene and (1-3C)alkyleneSO$_2$—; where the alkylene group in any $X^1$ is optionally substituted with 1 or 2 substituents independently selected from (1-4C)alkyl and —NR$^{Xa}$R$^{Xb}$; wherein R$^{Xa}$ and R$^{Xb}$ are independently selected from hydrogen and (1-4alkyl);

s is 0, 1 or 2;
each $R^8$ independently represents (1-4C)alkyl, (2-4C)alkenyl, (2-4C)alkynyl, (3-6C)cycloalkyl, cyano, nitro, halo, N,N-di(1-4C)alkylamino(2-4C)alkoxy, —OR$^{8a}$, —C(O)OR$^{8b}$, —SR$^{8c}$, —S(O)R$^{8d}$, —S(O)$_2$R$^{8e}$ or —NR$^{8f}$R$^{8g}$; each of R$^{8a}$, R$^{8b}$, R$^{8c}$, R$^{8d}$, R$^{8e}$, R$^{8f}$ and R$^{8g}$ is independently hydrogen, (1-4C)alkyl, (3-6C)cycloalkyl, phenyl or phenyl(1-4C)alkyl, wherein each phenyl group is unsubstituted or substituted by 1 or 2 substituents independently selected from halo, (1-4C)alkyl and (1-4C)alkoxy;

$R^9$ is selected from hydrogen, (1-4C)alkyl, (1-4C)alkyleneNR$^{9a}$R$^{9b}$, and phenyl, each of R$^{9a}$ and R$^{9b}$ is independently hydrogen or (1-4C)alkyl; or $R^9$ is taken together with $R^8$ to form a ring having 1 to 2 oxygen atoms, where said ring is unsubstituted or substituted by 1 or 2 (1-4C)alkyl substituents; and wherein each alkyl and alkoxy group in $R^1$, $R^{1a-1k}$, $R^2$, $R^{2a-2k}$, $R^3$, $R^5$, $R^8$, $R^{8a-8g}$, $R^9$, and $R^{9a-9b}$ is optionally substituted with 1 to 5 fluoro substituents;

or a pharmaceutically acceptable salt or solvate or stereoisomer thereof.

Exemplary a, b, c, m, n, q, r, and s values, and exemplary W, $Ar^1$, $X^1$, $R^{1-4}$, and $R^{6-9}$ substituents are as described below.

Another aspect of the invention relates to a compound of formula Ia':

an integer from 1 to 4 and each $R^5$ is independently selected from halo, hydroxy, (1-4C)alkyl or (1-4C)alkoxy;

q is 0 or 1;

$R^6$ is selected from hydrogen, (1-4C)alkyl, and (3-4C)cycloalkyl;

r is 0, 1 or 2;

wherein each alkyl and alkoxy group in $R^1$, $R^{1a-1k}$, $R^2$, $R^{2a-2k}$, $R^3$, and $R^5$ is optionally substituted with 1 to 5 fluoro substituents;

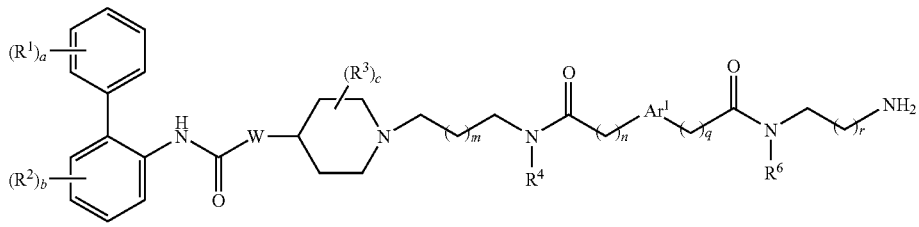

Ia' wherein:

a is 0 or an integer of from 1 to 5;

each $R^1$ is independently selected from (1-4C)alkyl, (2-4C)alkenyl, (2-4C)alkynyl, (3-6C)cycloalkyl, cyano, halo, —$OR^{1a}$, —$C(O)OR^{1b}$, —$SR^{1c}$, —$S(O)R^{1d}$, —$S(O)_2R^{1e}$, —$NR^{1f}R^{1g}$, —$NR^{1h}S(O)_2R^{1i}$, and —$NR^{1j}C(O)R^{1k}$; where each of $R^{1a}, R^{1b}, R^{1c}, R^{1d}, R^{1e}, R^{1f}, R^{1g}, R^{1h}, R^{1i}, R^{1j}$, and $R^{1k}$ is independently hydrogen, (1-4C)alkyl or phenyl(1-4C)alkyl;

b is 0 or an integer of from 1 to 4;

each $R^2$ is independently selected from (1-4C)alkyl, (2-4C)alkenyl, (2-4C)alkynyl, (3-6C)cycloalkyl, cyano, halo, —$OR^{2a}$, —$C(O)OR^{2b}$, —$SR^{2c}$, —$S(O)R^{2d}$, —$S(O)_2R^{2e}$, —$NR^{2f}R^{2g}$, —$NR^{2h}S(O)_2R^{2i}$, and —$NR^{2j}C(O)R^{2k}$; where each of $R^{2a}, R^{2b}, R^{2c}, R^{2d}, R^{2e}, R^{2f}, R^{2g}, R^{2h}, R^{2i}, R^{2j}$, and $R^{2k}$ is independently hydrogen, (1-4C)alkyl or phenyl(1-4C)alkyl;

W represents O or $NW^a$, where $W^a$ is hydrogen or (1-4C)alkyl;

c is 0 or an integer from 1 to 5;

each $R^3$ independently represents (1-4C)alkyl or two $R^3$ groups are joined to form (1-3C)alkylene, (2-3C)alkenylene or oxiran-2,3-diyl;

m is 0 or 1;

or a pharmaceutically acceptable salt or solvate or stereoisomer thereof.

Exemplary a, b, c, m, n, q, and r values, and exemplary W, $Ar^1$, $R^{1-4}$ and $R^6$ substituents are as described below.

Another embodiment of the invention pertains to compounds of formula I, where $Z^1$ is —C(O)N($R^4$)— and $Z^2$ is selected from —C(O)N($R^6$)— and —N($R^6$)C(O)—, or $Z^1$ is —N($R^4$)C(O)— and $Z^2$ is —N($R^6$)C(O)—; and Y is:

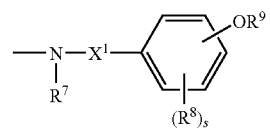

These compounds have the following formula Ib:

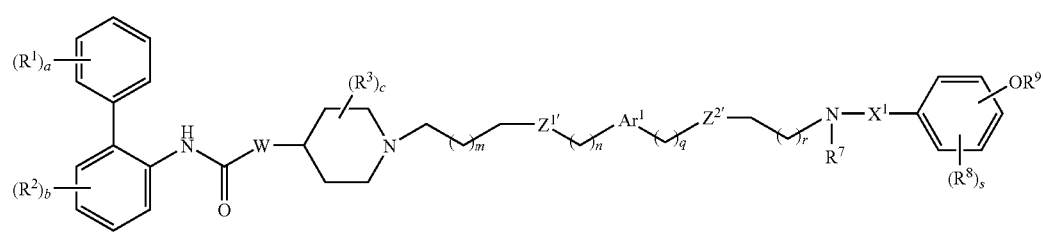

Ib $R^4$ is selected from hydrogen, (1-4C)alkyl, and (3-4C)cycloalkyl;

n is 0 or 1;

$Ar^1$ represents a phenylene group or a (3-5C)heteroarylene group containing 1 or 2 heteroatoms independently selected from oxygen, nitrogen or sulfur; wherein the phenylene or heteroarylene group is substituted with $(R^5)_p$ where p is 0 or wherein:

a is 0 or an integer of from 1 to 5;

each $R^1$ is independently selected from (1-4C)alkyl, (2-4C)alkenyl, (2-4C)alkynyl, (3-6C)cycloalkyl, cyano, halo, —$OR^{1a}$, —$C(O)OR^{1b}$, —$SR^{1c}$, —$S(O)R^{1d}$, —$S(O)_2R^{1e}$, —$NR^{1f}R^{1g}$, —$NR^{1h}S(O)_2R^{1i}$, and —$NR^{1j}C(O)R^{1k}$; where each of $R^{1a}, R^{1b}, R^{1c}, R^{1d}, R^{1e}, R^{1f}, R^{1g}, R^{1h}, R^{1i}, R^{1j}$, and $R^{1k}$ is independently hydrogen, (1-4C)alkyl or phenyl(1-4C)alkyl;

b is 0 or an integer of from 1 to 4;

each $R^2$ is independently selected from (1-4C)alkyl, (2-4C)alkenyl, (2-4C)alkynyl, (3-6C)cycloalkyl, cyano, halo, $-OR^{2a}$, $-C(O)OR^{2b}$, $-SR^{2c}$, $-S(O)R^{2d}$, $-S(O)_2R^{2e}$, $-NR^{2f}R^{2g}$, $-NR^{2h}S(O)_2R^{2i}$, and $-NR^{2j}C(O)R^{2k}$; where each of $R^{2a}$, $R^{2b}$, $R^{2c}$, $R^{2d}$, $R^{2e}$, $R^{2f}$, $R^{2g}$, $R^{2h}$, $R^{2i}$, $R^{2j}$, and $R^{2k}$ is independently hydrogen, (1-4C)alkyl or phenyl(1-4C)alkyl;

W represents O or $NW^a$, where $W^a$ is hydrogen or (1-4C)alkyl;

c is 0 or an integer from 1 to 5;

each $R^3$ independently represents (1-4C)alkyl or two $R^3$ groups are joined to form (1-3C)alkylene, (2-3C)alkenylene or oxiran-2,3-diyl;

m is 0 or 1;

$Z^{1'}$ is $-C(O)N(R^4)-$ and $Z^{2'}$ is selected from $-C(O)N(R^6)-$ and $-N(R^6)C(O)-$; or $Z^{1'}$ is $-N(R^4)C(O)-$ and $Z^{2'}$ is $-N(R^6)C(O)-$;

$R^4$ is selected from hydrogen, (1-4C)alkyl, and (3-4C)cycloalkyl;

$R^6$ is selected from hydrogen, (1-4C)alkyl, and (3-4C)cycloalkyl;

n is 0 or 1;

$Ar^1$ represents a phenylene group or a (3-5C)heteroarylene group containing 1 or 2 heteroatoms independently selected from oxygen, nitrogen or sulfur; wherein the phenylene or heteroarylene group is substituted with $(R^5)_p$ where p is 0 or an integer from 1 to 4 and each $R^5$ is independently selected from halo, hydroxy, (1-4C)alkyl or (1-4C)alkoxy;

q is 0 or 1;

r is 0, 1 or 2;

$R^7$ is selected from hydrogen, (1-4C)alkyl, (3-4C)cycloalkyl, $-C(O)(1-4C)$alkyl, $-(1-4C)$alkyleneC(O)OR$^{7a}$, $-C(O)$heterocyclyl, $-C(O)CH(NH_2)(1-4C)$alkyleneQ, $-(1-4C)$alkyleneC(O)Q', $-C(O)(1-4C)$alkyleneQ', and $-S(O)_2(1-4C)$alkyleneQ'; where Q is a nitrogen-containing substituent selected from $-NR^{7b}R^{7c}$ and heteroaryl; Q' is a nitrogen-containing substituent selected from $-NR^{7d}R^{7e}$ and heterocyclyl; $R^{7a}$ is hydrogen or (1-4C)alkyl; each of $R^{7b}$, $R^{7c}$, $R^{7d}$ and $R^{7e}$ independently represents hydrogen, (1-4C)alkyl, (3-6C)cycloalkyl or hydroxyphenyl, and where (1-4C)alkyl is unsubstituted or substituted by 1 or 2 substituents independently selected from amido, cyano, furyl, hydroxyl, and methylimidazolyl; the heterocyclyl contains 1 or 2 nitrogen atoms, and is unsubstituted or substituted by 1 or 2 substituents independently selected from hydroxyl, amido, (1-4C)alkoxy, oxo, $-S(O)_2(1-4C)$alkyl, $-(CH_2)O(1-4C)$alkyl, $-(1-4C)$alkyleneOH, $-NR^{7f}R^{7g}$ and $-C(O)NR^{7h}R^{7i}$, where each of $R^{7f}$, $R^{7g}$ $R^{7h}$ and $R^{7i}$ independently represents hydrogen or (1-4C)alkyl; and the heteroaryl contains 1 or 2 nitrogen atoms;

$X^1$ is selected from (1-3C)alkylene, $-C(O)(1-3C)$alkylene, (1-3C)alkyleneC(O)$-$, $-SO_2-$, $-SO_2(1-3C)$alkylene and (1-3C)alkyleneSO$_2-$; where the alkylene group in any $X^1$ is optionally substituted with 1 or 2 substituents independently selected from (1-4C)alkyl and $-NR^{Xa}R^{Xb}$; wherein $R^{Xa}$ and $R^{Xb}$ are independently selected from hydrogen and (1-4alkyl);

s is 0, 1 or 2;

each $R^8$ independently represents (1-4C)alkyl, (2-4C)alkenyl, (2-4C)alkynyl, (3-6C)cycloalkyl, cyano, nitro, halo, N,N-di(1-4C)alkylamino(2-4C)alkoxy, $-OR^{8a}$, $-C(O)OR^{8b}$, $-SR^{8c}$, $-S(O)R^{8d}$, $-S(O)_2R^{8e}$ or $-NR^{8f}R^8$; each of $R^{8a}$, $R^{8b}$, $R^{8c}$, $R^{8d}$, $R^{8e}$, $R^{8f}$ and $R^{8g}$ is independently hydrogen, (1-4C)alkyl, (3-6C)cycloalkyl, phenyl or phenyl(1-4C)alkyl, wherein each phenyl group is unsubstituted or substituted by 1 or 2 substituents independently selected from halo, (1-4C)alkyl and (1-4C)alkoxy;

$R^9$ is selected from hydrogen, (1-4C)alkyl, (1-4C)alkyleneNR$^{9a}$R$^{9b}$, and phenyl, each of $R^{9a}$ and $R^{9b}$ is independently hydrogen or (1-4C)alkyl; or $R^9$ is taken together with $R^8$ to form a ring having 1 to 2 oxygen atoms, where said ring is unsubstituted or substituted by 1 or 2 (1-4C)alkyl substituents; and wherein each alkyl and alkoxy group in $R^1$, $R^{1a-1k}$, $R^2$, $R^{2a-2k}$, $R^3$, $R^5$, $R^8$, $R^{8a-8g}$, $R^9$, and $R^{9a-9b}$ is optionally substituted with 1 to 5 fluoro substituents;

or a pharmaceutically acceptable salt or solvate or stereoisomer thereof.

Exemplary a, b, c, m, n, q, r and s values, and exemplary W, $Ar^1$, $X^1$, $R^{1-4}$, and $R^{6-9}$ substituents are as described below.

Yet another embodiment of the invention pertains to compounds of formula I, where Y selected from

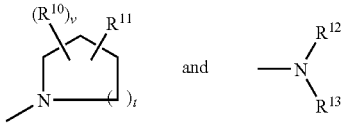

and

These compounds have the following formula Ic:

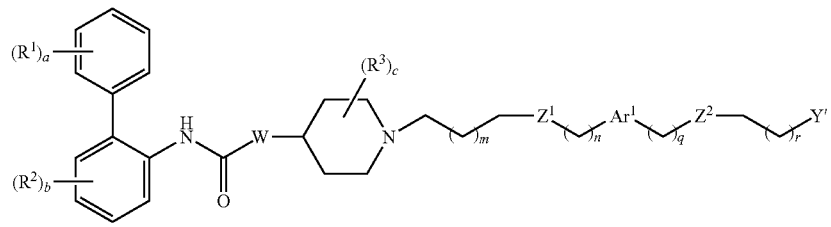

wherein:

a is 0 or an integer of from 1 to 5;

each $R^1$ is independently selected from (1-4C)alkyl, (2-4C)alkenyl, (2-4C)alkynyl, (3-6C)cycloalkyl, cyano, halo, $-OR^{1a}$, $-C(O)OR^{1b}$, $-SR^{1c}$, $-S(O)R^{1d}$, $-S(O)_2R^{1e}$, $-NR^{1f}R^{1g}$, $-NR^{1h}S(O)_2R^{1i}$, and $-NR^{1j}C(O)R^{1k}$; where each of $R^{1a}$, $R^{1b}$, $R^{1c}$, $R^{1d}$, $R^{1e}$, $R^{1f}$, $R^{1g}$, $R^{1h}$, $R^{1i}$, $R^{1j}$, and $R^{1k}$ is independently hydrogen, (1-4C)alkyl or phenyl(1-4C)alkyl;

b is 0 or an integer of from 1 to 4;

each $R^2$ is independently selected from (1-4C)alkyl, (2-4C)alkenyl, (2-4C)alkynyl, (3-6C)cycloalkyl, cyano, halo, $-OR^{2a}$, $-C(O)OR^{2b}$, $-SR^{2c}$, $-S(O)R^{2d}$, $-S(O)_2R^{2e}$, $-NR^{2f}R^{2g}$, $-NR^{2h}S(O)_2R^{2i}$, and $-NR^{2j}C(O)R^{2k}$; where each of $R^{2a}, R^{2b}, R^{2c}, R^{2d}, R^{2e}, R^{2f}, R^{2g}, R^{2h}, R^{2i}, R^{2j}$, and $R^{2k}$ is independently hydrogen, (1-4C)alkyl or phenyl(1-4C)alkyl;

W represents O or $NW^a$, where $W^a$ is hydrogen or (1-4C)alkyl;

c is 0 or an integer from 1 to 5;

each $R^3$ independently represents (1-4C)alkyl or two $R^3$ groups are joined to form (1-3C)alkylene, (2-3C)alkenylene or oxiran-2,3-diyl;

m is 0 or 1;

$Z^1$ is selected from —C(O)N($R^4$)— and —N($R^4$)C(O)—, where $R^4$ is selected from hydrogen, (1-4C)alkyl, and (3-4C)cycloalkyl;

n is 0 or 1;

$Ar^1$ represents a phenylene group or a (3-5C)heteroarylene group containing 1 or 2 heteroatoms independently selected from oxygen, nitrogen or sulfur; wherein the phenylene or heteroarylene group is substituted with $(R^5)_p$ where p is 0 or an integer from 1 to 4 and each $R^5$ is independently selected from halo, hydroxy, (1-4C)alkyl or (1-4C)alkoxy;

q is 0 or 1;

$Z^2$ is selected from —C(O)N($R^6$)— and —N($R^6$)C(O)—, where $R^6$ is selected from hydrogen, (1-4C)alkyl, and (3-4C)cycloalkyl;

r is 0, 1 or 2;

Y' is selected from

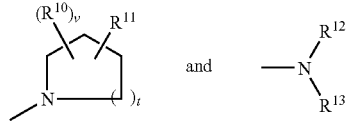 and where:

t is 0 or an integer from 1 to 3;

v is 0 or an integer from 1 to 4;

each $R^{10}$ independently represents fluoro or (1-4C)alkyl;

$R^{11}$ is selected from hydrogen, —OH, -(1-4C)alkyleneOH, —C(O)NR$^{11a}$R$^{11b}$, and —CH$_2$C(O)NR$^{11a}$R$^{11b}$, where $R^{11a}$ and $R^{11b}$ are independently selected from hydrogen, (1-4C)alkyl, hydroxy, (1-4C)alkoxy, (1-4C)alkyleneOR$^{11c}$, (3-6C)cycloalkyl, phenyl optionally substituted with hydroxy, and (1-4C)alkyleneC(O)NR$^{11d}$R$^{11e}$, where said (3-6C)cycloalkyl is unsubstituted or substituted with 1 or 2 (1-6C)alkyl or —NR$^{11d}$R$^{11e}$ groups, and where each of $R^{11c}$, $R^{11d}$ and $R^{11e}$ is independently hydrogen or (1-4C)alkyl; or $R^{11a}$ is taken together with $R^{11b}$ to form a 3-7 membered ring, optionally substituted with hydroxyl;

$R^{12}$ is selected from hydrogen, (1-4C)alkyl, -(1-4C)alkyleneOH, and -(1-4C)alkyleneheteroaryl; and $R^{13}$ is selected from (1-4C)alkyl, -(1-4C)alkyleneOH, -(1-4C)alkyleneheteroaryl, (3-6C)cycloalkyl, -(1-4C)alkylene (3-6C)cycloalkyl, and -(1-4C)alkyleneC(O)NR$^{13a}$R$^{13b}$, where $R^{13a}$ and $R^{13b}$ are independently hydrogen or (1-4C)alkyl; or $R^{12}$ and $R^{13}$ are taken together to form a ring selected from piperazinone, morpholine, and piperazine; and said piperazine is substituted with $(R^{13c})_w$ where w is 0 or an integer from 1 to 3 and each $R^{13c}$ is independently selected from (1-4C)alkyl, phenyl or benzyl, optionally substituted with 1 to 5 fluoro substituents, or two $R^{13c}$ groups are joined to form (1-3C)alkylene;

wherein each alkyl and alkoxy group in $R^1$, $R^{1a-1k}$, $R^2$, $R^{2a-2k}$, $R^3$, and $R^5$ is optionally substituted with 1 to 5 fluoro substituents;

or a pharmaceutically acceptable salt or solvate or stereoisomer thereof.

Exemplary a, b, c, m, n, q, r, t and v values, and exemplary W, $Z^1$, $Ar^1$, $Z^2$, Y, $R^{1-3}$, and $R^{10-13}$ substituents are as described below.

Unless specified otherwise, the following discussion relates to the integers and substituents present in compounds having formulas I, Ia, Ib, Ic, and Ia', as well as in the formulas of compounds discussed in the general synthetic procedures section.

The value for a is 0, 1, 2, 3, 4 or 5; particularly 0, 1 or 2, and even more particularly 0 or 1. The value for b is 0, 1, 2, 3 or 4; particularly 0, 1 or 2, and even more particularly 0 or 1. In one embodiment, a is 0. In another embodiment, b is zero. In yet another embodiment, both a and b are 0.

When present, each $R^1$ may be at the 2, 3, 4, 5 or 6-position of the phenyl ring to which it is attached. Each $R^1$ is independently selected from (1-4C)alkyl, (2-4C)alkenyl, (2-4C)alkynyl, (3-6C)cycloalkyl, cyano, halo, —OR$^{1a}$, —C(O)OR$^{1b}$, —SR$^{1c}$, —S(O)R$^{1d}$, —S(O)$_2$R$^{1e}$, —NR$^{1f}$R$^{1g}$, —NR$^{1h}$S(O)$_2$R$^{1i}$, and —NR$^{1j}$C(O)R$^{1k}$, examples of which include methyl, fluoro, chloro, bromo, hydroxy, methoxy, amino, methylamino, dimethylamino and the like. Particular values for $R^1$ are fluoro or chloro.

When present, each $R^2$ may be at the 3, 4, 5 or 6-position on the phenylene ring to which it is attached (where the carbon atom on the phenylene ring attached to the nitrogen atom is position 1). Each $R^2$ is independently selected from (1-4C)alkyl, (2-4C)alkenyl, (2-4C)alkynyl, (3-6C)cycloalkyl, cyano, halo, —OR$^{2a}$, —C(O)OR$^{2b}$, —SR$^{2c}$, —S(O)R$^{2d}$, —S(O)$_2$R$^{2e}$, —NR$^{2f}$R$^{2g}$, —NR$^{2h}$S(O)$_2$R$^{2i}$, and —NR$^{2j}$C(O)R$^{2k}$, examples of which include methyl, fluoro, chloro, bromo, hydroxy, methoxy, amino, methylamino, dimethylamino and the like. Particular values for $R^2$ are fluoro or chloro.

Each $R^{1a-1k}$ and $R^{2a-2k}$ group as used in $R^1$ and $R^2$, respectively, is independently hydrogen, (1-4C)alkyl or phenyl(1-4C)alkyl, examples of which include hydrogen, methyl, ethyl, n-propyl, isopropyl, n-butyl, sec-butyl, isobutyl, tert-butyl or benzyl. In one embodiment, these groups are independently hydrogen or (1-3C)alkyl. In another embodiment, these groups are independently hydrogen, methyl or ethyl. In addition, each alkyl and alkoxy group in $R^1$, $R^{1a-1k}$, $R^2$, and $R^{2a-2k}$ is optionally substituted with 1 to 5 fluoro substituents.

W can be O or $NW^a$. Generally, it has been found that compounds in which W represents O exhibit particularly high affinity for muscarinic receptors. Accordingly, in a particular embodiment of the invention, W represents O.

When W is $NW^a$, $W^a$ is hydrogen or (1-4C)alkyl, examples of which include hydrogen, methyl, ethyl, n-propyl, isopropyl, n-butyl, sec-butyl, isobutyl and tert-butyl. In one embodiment, $W^a$ is hydrogen or (1-3C)alkyl. In another embodiment, $W^a$ is hydrogen, methyl or ethyl, particularly hydrogen or methyl. In yet another embodiment, $W^a$ is hydrogen.

The value for c is 0, 1, 2, 3, 4, or 5; particularly 0, 1, or 2; and more particularly 0 or 1. In one particular embodiment, c is 0. In another embodiment, c is 2.

In one embodiment, each $R^3$ is at the 3, 4 or 5-position on the piperidine ring (where the nitrogen atom of the piperidine ring is position 1). In a particular embodiment, $R^3$ is at 4-position on the piperidine ring. In another embodiment, $R^3$ is at the 1-position of the piperidine ring, i.e., on the nitrogen atom of the piperidine ring thus forming a quaternary amine salt. Each $R^3$ is independently (1-4C)alkyl, or two $R^3$ groups are joined to form (1-3C)alkylene, (2-3C)alkenylene or oxiran-2,3-diyl. In one embodiment, each $R^3$ is independently (1-4C)alkyl such as methyl, ethyl, n-propyl, isopropyl, n-butyl, sec-butyl, isobutyl and tert-butyl. In addition, each alkyl group in $R^3$ is optionally substituted with 1 to 5 fluoro substituents. In one embodiment, each $R^3$ is independently (1-3C) alkyl, and in another embodiment, each $R^3$ is independently methyl or ethyl.

In yet another embodiment, two $R^3$ groups are joined to form a (1-3C)alkylene or (2-3C)alkenylene group. For example, two $R^3$ groups at the 2 and 6-positions on the piperidine ring can be joined to form an ethylene bridge (i.e., the piperidine ring and the $R^3$ groups form an 8-azabicyclo[3.2.1] octane ring); or two $R^3$ groups at the 1 and 4-positions on the piperidine ring can be joined to form an ethylene bridge (i.e., the piperidine ring and the $R^3$ groups form an 1-azabicyclo[2.2.2]octane ring). In this embodiment, other $R^3$ groups as defined herein may also be present.

In still another embodiment, two $R^3$ groups are joined to form a oxiran-2,3-diyl group. For example, two $R^3$ groups at the 2 and 6-positions on the piperidine ring can be joined to form a 3-oxatricyclo[3.3.1.0$^{2,4}$]nonane ring). In this embodiment, other $R^3$ groups as defined herein may also be present.

The value for m is 0 or 1. In one embodiment, m is 0.

In the compounds of formulas I and Ic, $Z^1$ is —C(O)N($R^4$)— or —N($R^4$)C(O)—, while in the compound of formula Ib, $Z^{1'}$ is —C(O)N($R^4$)— or —N($R^4$)C(O)—. $R^4$ in formulas I, Ia-c and Ia', represents hydrogen, (1-4C)alkyl, or (3-4C) cycloalkyl. Examples of (1-4C)alkyl include methyl, ethyl, n-propyl, isopropyl, n-butyl, sec-butyl, isobutyl and tert-butyl. Examples of (3-4C)cycloalkyl groups include cyclopropyl and cyclobutyl. In one embodiment $R^4$ represents hydrogen or (1-4C)alkyl, in particular hydrogen or methyl. In another embodiment, $R^4$ is hydrogen. In one particular embodiment, $Z^1$ is —N($R^4$)C(O)—.

The value for n is 0 or 1. A particular value for n is 0.

$Ar^1$ is a phenylene group or a (3-5C)heteroarylene group containing 1 or 2 heteroatoms independently selected from oxygen, nitrogen or sulfur. The value for p is 0, 1, 2, 3, or 4, particularly 0, 1, 2 or 3. In one embodiment, p is 0, 1 or 2. Thus, the phenylene or heteroarylene group may be unsubstituted (p is 0) or substituted with 1 to 4 $R^5$ substituents, which are independently selected from halo, hydroxy, (1-4C) alkyl or (1-4C)alkoxy. In addition, each alkyl and alkoxy group in $R^5$ is optionally substituted with 1 to 5 fluoro substituents. The point of attachment for $Ar^1$ is at any available carbon or heteroatom ring atom. In certain embodiments, $Ar^1$ is a phenylene group attached at the meta or para position.

In one embodiment $Ar^1$ is phen-1,3-ylene or phen-1,4-ylene wherein the phenylene group is unsubstituted or substituted with 1, 2 or 3 $R^5$ substituents. Representative $R^5$ substituents include fluoro, chloro, bromo, methyl, ethyl, n-propyl, isopropyl, n-butyl, isobutyl, sec-butyl, tert-butyl, methoxy, ethoxy, isopropoxy, difluoromethyl, trifluoromethyl, 2,2,2-trifluoroethyl and trifluoromethoxy. Particular examples of $Ar^1$ groups in this embodiment include 2-fluorophen-1,4-ylene, 3-fluorophen-1,4-ylene, 2-chlorophen-1,4-ylene, 3-chlorophen-1,4-ylene, 2-methylphen-1,4-ylene, 3-methylphen-1,4-ylene, 2-methoxyphen-1,4-ylene, 3-methoxyphen-1,4-ylene, 2-trifluoromethoxyphen-1,4-ylene, 3-trifluoromethoxyphen-1,4-ylene, 2,3-difluorophen-1,4-ylene, 2,5-difluorophen-1,4-ylene, 2,6-difluorophen-1,4-ylene, 2,3-dichlorophen-1,4-ylene, 2,5-dichlorophen-1,4-ylene, 2,6-dichlorophen-1,4-ylene, 2-chloro-5-methoxyphen-1,4-ylene, 2-chloro-6-methoxyphen-1,4-ylene, 2-chloro-5-trifluoromethoxyphen-1,4-ylene, 2-chloro-6-trifluoromethoxyphen-1,4-ylene, and 2,5-dibromophen-1,4-ylene.

In another embodiment, $Ar^1$ is a (3-5C)heteroarylene group containing 1 or 2 heteroatoms independently selected from oxygen, nitrogen and sulfur; wherein the heteroarylene group is unsubstituted or substituted with 1 or 2 $R^5$ substituents. Representative heteroarylene groups include divalent species of pyrrole, imidazole, thiazole, oxazole, furan, thiophene, pyrazole, isoxazole, isothiazole, pyridine, pyrazine, pyridazine and pyrimidine, where the point of attachment is at any available carbon or nitrogen ring atom. More specific examples of such $Ar^1$ groups include 2,5-furylene, 2,4-thienylene, 2,5-thienylene, 2,5-pyridylene, 2,6-pyridylene, 3,5-pyridylene and 2,5-pyrrolylene. Representative $R^5$ substituents include fluoro, chloro, methyl, ethyl, n-propyl, isopropyl, n-butyl, isobutyl, sec-butyl, tert-butyl, methoxy, ethoxy, isopropoxy, difluoromethyl, trifluoromethyl, 2,2,2-trifluoroethyl and trifluoromethoxy. Particular examples of substituted $Ar^1$ groups include 3-fluoro-2,5-thienylene, 3-chloro-2,5-thienylene, 3-methyl-2,5-thienylene, 3-methoxy-2,5-thienylene, and 3-methoxy-6-chloro-2,5-pyridylene.

In one particular embodiment, $Ar^1$ represents phen-1,3-ylene, phen-1,4-ylene, 2,4-thienylene or 2,5-thienylene; wherein the phenylene or thienylene group is optionally substituted with 1 or 2 $R^5$ substituents. In another particular embodiment, $Ar^1$ represents phen-1,3-ylene or 2,5-thienylene optionally substituted with 1 or 2 $R^5$ substituents.

The value for q is 0 or 1. A particular value for q is 0.

In the compounds of formulas I and Ic, $Z^2$ is —C(O)N($R^6$)— or —N($R^6$)C(O)—, while in the compound of formula Ib, $Z^{2'}$ is —C(O)N($R^6$)— or —N($R^6$)C(O)—. $R^6$ in formulas I, Ia-c and Ia', represents hydrogen, (1-4C)alkyl, or (3-4C) cycloalkyl. Examples of (1-4C)alkyl include methyl, ethyl, n-propyl, isopropyl, n-butyl, sec-butyl, isobutyl and tert-butyl. Examples of (3-4C)cycloalkyl groups include cyclopropyl and cyclobutyl. In one embodiment $R^6$ represents hydrogen or (1-4C)alkyl, in particular hydrogen or methyl. In another embodiment, $R^6$ is hydrogen. In one particular embodiment, $Z^2$ is —C(O)N($R^6$)—.

The value for r is 0, 1, or 2. In one embodiment, r is 0. In another embodiment, r is 1.

In compounds of formula I, Y is selected from

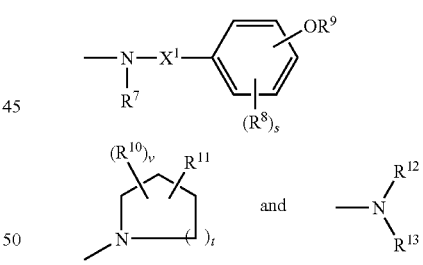

In one particular embodiment or formula I, and in the embodiment of formulas Ia and Ib, Y is

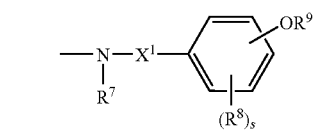

$R^7$ represents hydrogen, (1-4C)alkyl, (3-4C)cycloalkyl, —C(O)(1-4C)alkyl, (1-4C)alkyleneC(O)OR$^{7a}$, —C(O)heterocyclyl, —C(O)CH(NH$_2$)(1-4C)alkyleneQ, -(1-4C)alkyleneC(O)Q', —C(O)(1-4C)alkyleneQ', or —S(O)$_2$(1-4C)alkyleneQ'. Q is a nitrogen-containing substituent selected from —$NR^{7b}R^{7c}$ and heteroaryl. Q' is a nitrogen-containing substituent selected from —$NR^{7d}R^{7e}$ and heterocyclyl. $R^{7a}$ is hydrogen or (1-4C)alkyl. Each of $R^{7b}$, $R^{7c}$, $R^{7d}$ and $R^{7e}$ independently represents hydrogen, (1-4C)alkyl, (3-6C)cycloalkyl or hydroxyphenyl, and (1-4C)alkyl is unsubstituted or substituted by 1 or 2 substituents independently selected from amido, cyano, furyl, hydroxyl, and methylimidazolyl. The heterocyclyl contains 1 or 2 nitrogen atoms, and is unsubstituted or substituted by 1 or 2 substituents independently selected from hydroxyl, amido, (1-4C)alkoxy, oxo, —$S(O)_2$(1-4C)alkyl, —$(CH_2)O$(1-4C)alkyl, -(1-4C)alkyleneOH, —$NR^{7f}R^{7g}$ and —$C(O)NR^{7h}R^{7i}$, where each of $R^{7f}$, $R^{7g}$ $R^{7h}$ and $R^{7i}$ independently represents hydrogen or (1-4C)alkyl. The heteroaryl contains 1 or 2 nitrogen atoms. The heterocyclyl and heteroaryl groups may contain other heteroatoms, in addition to the 1 or 2 nitrogen atoms. For example the heterocyclyl can be a morpholinyl group.

In one embodiment, $R^7$ represents hydrogen, (1-4C)alkyl, or (3-4C)cycloalkyl, examples of which include methyl, ethyl, n-propyl, isopropyl, n-butyl, sec-butyl, isobutyl, tert-butyl, cyclopropyl and cyclobutyl. In another embodiment, $R^7$ represents hydrogen or (1-3C)alkyl, particularly methyl. In another particular embodiment, $R^7$ is methyl. In yet another embodiment, $R^7$ is hydrogen.

In one embodiment, $R^7$ is —$C(O)$(1-4C)alkyl. Particular embodiments include where $R^7$ is —$C(O)CH_3$ and —$C(O)CH_2CH_3$.

In another embodiment, $R^7$ is -(1-4C)alkyleneC(O)$OR^{7a}$. In particular embodiments, $R^7$ is —$(CH_2)_2C(O)OH$ or —$(CH_2)_2C(O)OCH_3$.

In yet another embodiment, $R^7$ is —$C(O)$heterocyclyl. In a particular embodiment, the heterocyclyl contains 1 nitrogen atom, and is unsubstituted or substituted with a hydroxyl. Particular embodiments include where the heterocyclyl is pyrrolidinyl, hydroxypyrrolidinyl or piperidyl.

In another embodiment, $R^7$ is —$C(O)CH(NH_2)$(1-4C)alkyleneQ. In one particular embodiment, Q is —$NR^{7b}R^{7c}$ such as —$NH_2$. In another embodiment, Q is a heteroaryl such as pyridyl or imidazolyl.

In a particular embodiment, $R^7$ is -(1-4C)alkyleneC(O)Q', where Q' is —$NR^{7d}R^{7e}$, for example —$(CH_2)_2C(O)NR^{7d}R^{7e}$. In one embodiment, $R^{7d}$ and $R^{7e}$ are both (1-4C)alkyl, and methyl in particular. In another embodiment, $R^{7d}$ is hydrogen and $R^{7e}$ is selected from (1-4C)alkyl (such as methyl and ethyl), (3-6C)cycloalkyl (such as cyclopropyl) and hydroxyphenyl. In one embodiment, the (1-4C)alkyl is unsubstituted or substituted with furyl, hydroxyl or methylimidazolyl.

In a particular embodiment, $R^7$ is -(1-4C)alkyleneC(O)Q', where Q' is a heterocyclyl, for example —$(CH_2)_2C(O)$heterocyclyl. In one embodiment, the heterocyclyl contains 1 nitrogen atom such as piperidyl, and is substituted with an amido.

In still another embodiment, $R^7$ is —$C(O)$(1-4C)alkyleneQ', where Q' is —$NR^{7d}R^{7e}$, for example —$C(O)CH_2NR^{7d}R^{7e}$, —$C(O)(CH_2)_2NR^{7d}R^{7e}$, and —$C(O)(CH_2)_3NR^{7d}R^{7e}$. In a particular embodiment, each of $R^{7d}$ and $R^{7e}$ independently represents hydrogen, or (1-4C)alkyl. In another embodiment, $R^{7d}$ is hydrogen or methyl and $R^{7e}$ is (1-4C)alkyl substituted with amido, cyano, furyl, or hydroxyl.

In still another embodiment, $R^7$ is —$C(O)$(1-4C)alkyleneQ', where Q' is a heterocyclyl such as —$C(O)(CH_2)$heterocyclyl, —$C(O)(CH_2)_2$heterocyclyl and —$C(O)(CH_2)_3$heterocyclyl. In one embodiment, the heterocyclyl contains 1 nitrogen atom such as pyrrolidinyl or piperidyl. In another embodiment, the heterocyclyl contains 2 nitrogen atoms such as piperazinyl, tetrahydropyrimidinyl and 1,4 diazepanyl. In a particular embodiment, the heterocyclyl is pyrrolidinyl, unsubstituted or substituted with amido or (1-4C)alkoxy such as methoxy. In a particular embodiment, the heterocyclyl is piperidyl unsubstituted or substituted by 1 or 2 substituents independently selected from hydroxyl, amido, and (1-4C)alkoxy such as methoxy. In a particular embodiment, the heterocyclyl is tetrahydropyrimidinyl substituted with oxo. In another particular embodiment, the heterocyclyl is piperazinyl substituted with —$S(O)_2$(1-4C)alkyl such as —$S(O)_2CH_2CH_3$. In yet another embodiment, the heterocyclyl is 1,4 diazepanyl substituted with oxo.

In yet another embodiment, $R^7$ is —$S(O)_2$(1-4C)alkyleneQ', where Q' is —$NR^{7d}R^{7e}$ such as —$S(O)_2(CH_2)_2NR^{7d}R^{7e}$. In a particular embodiment each of $R^{7d}$ and $R^{7e}$ independently represents (1-4C)alkyl, where (1-4C)alkyl is substituted with hydroxyl, for example —$N(CH_2CH_2OH)_2$.

In yet another embodiment, $R^7$ is —$S(O)_2$(1-4C)alkyleneQ', where Q' is a heterocyclyl such as —$S(O)_2(CH_2)_2$heterocyclyl. In a particular embodiment, the heterocyclyl is piperidyl substituted with hydroxyl, -(1-4C)alkyleneOH such as —$(CH_2)_2OH$, or —$C(O)NR^{7h}R^{7i}$ such as —$(CO)N(CH_2CH_3)_2$. In another embodiment, the heterocyclyl is piperazinyl, substituted with oxo.

$X^1$ is selected from (1-3C)alkylene, —$C(O)$(1-3C)alkylene, (1-3C)alkyleneC(O)—, —$SO_2$—, —$SO_2$(1-3C)alkylene and (1-3C)alkyleneSO$_2$—. The alkylene group in any $X^1$ is optionally substituted with 1 or 2 substituents independently selected from (1-4C)alkyl and —$NR^{Xa}R^{Xb}$, where $R^{Xa}$ and $R^{Xb}$ are independently selected from hydrogen and (1-4alkyl). In one embodiment, $X^1$ is selected from (1-3C)alkylene, —$C(O)$(1-3C)alkylene, (1-3C)alkyleneC(O)— or —$SO_2$—. Examples of particular values for $X^1$ are —$CH_2$—, —$CH_2CH_2$—, —$CH_2C(O)$—, —$C(O)CH(NH_2)CH_2$— and —$SO_2$—. In a particular embodiment, $X^1$ is —$CH_2$— or —$CH_2CH_2$—.

The value for s is 0, 1, or 2. Particular values for s are 0 or 1. In one embodiment, is 0. In another embodiment, s is 1.

Each $R^8$ is independently (1-4C)alkyl, (2-4C)alkenyl, (2-4C)alkynyl, (3-6C)cycloalkyl, cyano, nitro, halo, N,N-di(1-4C)alkylamino(2-4C)alkoxy, —$OR^{8a}$, —$C(O)OR^{8b}$, —$SR^{8c}$, —$S(O)R^{8d}$, —$S(O)_2R^{8e}$ or —$NR^{8f}R^{8g}$. Each $R^{8a}$, $R^{8b}$, $R^{8c}$, $R^{8d}$, $R^{8e}$, $R^{8d}$ and $R^{8g}$ as used in $R^8$ is independently hydrogen, (1-4C)alkyl, (3-6C)cycloalkyl, phenyl or phenyl (1-4C)alkyl, where each phenyl group is unsubstituted or substituted by 1 or 2 substituents independently selected from halo, (1-4C)alkyl and (1-4C)alkoxy. In addition, each alkyl and alkoxy group in $R^8$ and $R^{8a-8g}$ is optionally substituted with 1 to 5 fluoro substituents. In one embodiment, each $R^8$ independently represents halo, (1-3C)alkyl, or (1-3C)alkoxy, where the alkyl and alkoxy groups are optionally substituted with 1 to 3 fluoro substituents. In another embodiment, each $R^8$ is independently selected from fluoro, chloro, bromo, methyl, methoxy, trifluoromethyl or trifluoromethoxy. In a particular embodiment, $R^8$ is —$OR^{8a}$ where $R^{8a}$ is hydrogen or methyl.

$R^9$ is selected from hydrogen, (1-4C)alkyl, (1-4C)alkyleneNR$^{9a}$R$^{9b}$, and phenyl; or $R^9$ may be taken together with $R^8$ (and the carbon atom or atoms to which they are attached) to form a ring having 1 to 2 oxygen atoms, where the ring is unsubstituted or substituted by 1 or 2 (1-4C)alkyl substituents. Each of $R^{9a}$ and $R^{9b}$ is independently hydrogen or (1-4C)alkyl. In addition, each alkyl group in $R^9$ and $R^{9a-9b}$ is optionally substituted with 1 to 5 fluoro substituents. In one embodiment, $R^9$ is hydrogen. In one embodiment, $R^9$ is (1-4C)alkyl such as methyl or methyl substituted with 2 or 3 fluoro substituents. In another embodiment, $R^9$ is (1-4C)alkyleneNR$^{9a}$R$^{9b}$, where each of $R^{9a}$ and $R^{9b}$ is independently (1-4C)alkyl such as —(CH$_2$)$_3$N(CH$_3$)$_2$. In a particular embodiment, R$^9$ is phenyl. In one embodiment, R$^9$ is taken together with R$^8$ to form a ring having 1 to 2 oxygen atoms, and the ring is unsubstituted or substituted by 1 or 2 (1-4C) alkyl substituents. Exemplary R$^9$/R$^8$ chains include, -O(CH$_2$)—O—, —O—C(CH$_3$)$_2$—(CH$_2$)$_2$—, —O—(CH$_2$)$_2$—, and —O(CH$_2$)$_2$—O—.

The —OR$^9$ group can be located at the ortho, meta or para position. In one embodiment, the —OR$^9$ group is located at the meta position; in another embodiment, the —OR$^9$ group is located at the ortho position; and in yet another embodiment, the —OR$^9$ group is located at the para position.

In one particular embodiment of formulas I and Ic, Y is

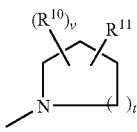

The value for t is 0, 1, 2, or 3. Particular values for t are 1 or 2. In one embodiment, t is 2.

The value for v is 0, 1, 2, 3, or 4. Particular values for v are 0, 1 or 2. In one embodiment, v is 0.

Each R$^{10}$ independently represents fluoro or (1-4C)alkyl, examples of which include methyl, ethyl, n-propyl, isopropyl, n-butyl, sec-butyl, isobutyl and tert-butyl. In addition, each alkyl and alkoxy group in R$^{10}$ is optionally substituted with 1 to 5 fluoro substituents. In one embodiment, each R$^{10}$ independently represents fluoro or (1-3C)alkyl, and in another embodiment, each R$^{10}$ is independently selected from fluoro, methyl, ethyl or trifluoromethyl.

R$^{11}$ is selected from hydrogen, —OH, -(1-4C)alkyleneOH, —C(O)NR$^{11a}$R$^{11b}$, and —CH$_2$C(O)NR$^{11a}$R$^{11b}$. R$^{11a}$ and R$^{11b}$ are independently selected from hydrogen, (1-4C)alkyl, hydroxy, (1-4C)alkoxy, (1-4C)alkyleneOR$^{11c}$, (3-6C)cycloalkyl, phenyl optionally substituted with hydroxy, and (1-4C)alkyleneC(O)NR$^{11d}$R$^{11e}$. The (3-6C)cycloalkyl is unsubstituted or substituted with 1 or 2 (1-6C)alkyl or —NR$^{11d}$R$^{11e}$ groups. Each of R$^{11c}$, R$^{11d}$ and R$^{11e}$ is independently hydrogen or (1-4C)alkyl. In addition, each alkyl and alkoxy group in R$^{11}$ and R$^{11a-e}$ is optionally substituted with 1 to 5 fluoro substituents. In another embodiment, R$^{11a}$ is taken together with R$^{11b}$ (and the nitrogen atom to which they are attached) to form a 3-7 membered ring, optionally substituted with hydroxyl. In one embodiment R$^{11}$ is selected from hydrogen, —OH, and —C(O)NR$^{11a}$R$^{11b}$, where R$^{11a}$ and R$^{11b}$ are hydrogen.

As noted in formula I, R$^{11}$ can be located at any carbon atom on the ring. For example, when t is 2, R$^{11}$ can be located at the ortho, meta or para position. In one embodiment, R$^{11}$ is located at the meta or para position; and in a particular embodiment, R$^{11}$ is located at the para position.

In yet another particular embodiment of formulas I and Ic, Y is —NR$^{12}$R$^{13}$. R$^{12}$ is selected from hydrogen, (1-4C)alkyl, -(1-4C)alkyleneOH, and -(1-4C)alkyleneheteroaryl. R$^{13}$ is selected from (1-4C)alkyl, -(1-4C)alkyleneOH, -(1-4C)alkyleneheteroaryl, (3-6C)cycloalkyl, -(1-4C)alkylene(3-6C)cycloalkyl, and -(1-4C)alkyleneC(O)NR$^{13a}$R$^{13b}$, where R$^{13a}$ and R$^{13b}$ are independently hydrogen or (1-4C)alkyl. In one embodiment, R$^{12}$ is hydrogen. In another embodiment, R$^{13}$ is (1-4C)alkyl, and in a particular embodiment, methyl or ethyl. In another embodiment, R$^{13}$ is -(1-4C)alkyleneOH such as —CH$_2$CH$_2$OH. In yet another embodiment, R$^{13}$ is (3-6C) cycloalkyl such as cyclopropyl or -(1-4C)alkylene(3-6C)cycloalkyl such as —CH$_2$-cyclopropyl. In another embodiment, R$^{13}$ is -(1-4C)alkyleneC(O)NR$^{13a}$R$^{13b}$ such as —CH$_2$C(O) NH$_2$. In another embodiment, R$^{12}$ is hydrogen and R$^{13}$ is a -(1-4C)alkyleneheteroaryl group such as pyridin-4-ylmethyl, thiophen-2-ylmethyl, furan-2-ylmethyl and 1H-imidazol-2-ylmethyl. In yet another embodiment, both R$^{12}$ and R$^{13}$ are -(1-4C)alkyleneheteroaryl groups such as 1H-imidazol-2-ylmethyl.

Alternately, R$^{12}$ and R$^{13}$ may be taken together (along with the nitrogen atom to which they are attached) to form a ring selected from piperazinone, morpholine, and piperazine. When a piperazine ring is formed, the piperazine ring may be substituted with (R$^{13c}$)$_w$ where w is 0 or an integer from 1 to 3. Each R$^{13c}$ is independently selected from (1-4C)alkyl, phenyl or benzyl, all of which may be optionally substituted with 1 to 5 fluoro substituents. In addition, two R$^{13c}$ groups may be joined to form (1-3C)alkylene. In one embodiment, R$^{12}$ and R$^{13}$ are taken together to form piperazin-2-one. In another embodiment, R$^{12}$ and R$^{13}$ are taken together to form piperazine having a 1 carbon bridge such as a 2,5-diaza-bicyclo [2.2.1]heptane ring. In yet another embodiment, R$^{12}$ and R$^{13}$ are taken together to form piperazine having a 1 carbon bridge, and the piperazine ring is further substituted with (1-4C)alkyl such as methyl, phenyl or phenyl substituted with fluoro, or benzyl.

A particular group of compounds of interest are compounds of formulas I, Ia-Ic, or Ia' where a, b, and c are 0. In another group of compounds of interest, W represents O. Another group of compounds of interest are compounds where m is 0. Other compounds of interest have Z$^1$ represented by —N(R$^4$)C(O)—. Another group of compounds of interest are compounds of where n is 0. In another group of compounds of interest, Ar$^1$ is phen-1,3-ylene or 2,5-thienylene. Another group of compounds of interest are compounds where q is 0. In another group of compounds of interest, Z$^2$ is —C(O)N(R$^6$)—. Another group of compounds of interest are compounds where r is 0 or 1. Combinations of the foregoing are also of interest. For example, in one group of compounds of interest, a, b, c, m, n, q are 0; W represents O; Z$^1$ is —N(R$^4$)C(O)—; Ar$^1$ represents phen-1,3-ylene or 2,5-thienylene; Z$^2$ is —C(O)N(R$^6$)—; r is 1; and Y is

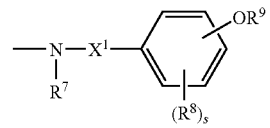

Another group of compounds of interest are compounds of formula I where Y is

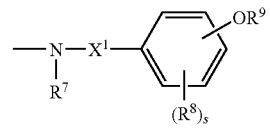

where R$^7$ is hydrogen; X$^1$ is selected from —CH$_2$— and —CH$_2$CH$_2$—; s is 0 or s is 1 and R$^8$ is —OR$^{8a}$ where R$^{8a}$ is hydrogen or methyl; and R$^9$ is hydrogen.

In another group of compounds of formula I and Ic of interest, Y is

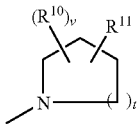

where t is 1 or 2; v is 0; and $R^{11}$ is selected from hydrogen, —OH, and —C(O)NR$^{11a}$R$^{11b}$, where $R^{11a}$ and $R^{11b}$ are hydrogen.

Another group of compounds of interest are compounds of formula I and Ic, where Y is —NR$^{12}$R$^{13}$, where $R^{12}$ is hydrogen; $R^{13}$ is selected from methyl, ethyl, —CH$_2$CH$_2$OH, cyclopropyl, —CH$_2$-cyclopropyl, and —CH$_2$C(O)NH$_2$; or $R^{12}$ and $R^{13}$ are taken together to form a piperazinone ring.

In addition, particular compounds of formula I that are of interest include:

biphenyl-2-ylcarbamic acid 1-[2-({3-[2-(4-hydroxybenzylamino)ethylcarbamoyl]benzoyl}methylamino)ethyl]piperidin-4-yl ester;
biphenyl-2-ylcarbamic acid 1-[2-({3-[2-(4-hydroxy-3-methoxybenzylamino)ethylcarbamoyl]benzoyl}methylamino)ethyl]piperidin-4-yl ester;
biphenyl-2-ylcarbamic acid 1-[2-({3-[2-(2-hydroxybenzylamino)ethylcarbamoyl]benzoyl}methylamino)ethyl]piperidin-4-yl ester;
biphenyl-2-ylcarbamic acid 1-[2-({3-[2-(4-methoxybenzylamino)ethylcarbamoyl]benzoyl}methylamino)ethyl]piperidin-4-yl ester;
biphenyl-2-ylcarbamic acid 1-(2-{3-[2-(4-hydroxy-2-methoxybenzylamino)ethylcarbamoyl]benzoylamino}ethyl)piperidin-4-yl ester;
biphenyl-2-ylcarbamic acid 1-(2-({3-[2-(2-hydroxybenzylamino)ethylcarbamoyl]benzoylamino}ethyl)piperidin-4-yl ester;
biphenyl-2-ylcarbamic acid 1-(2-{3-[2-(4-methoxybenzylamino)ethylcarbamoyl]benzoylamino}ethyl)piperidin-4-yl ester;
biphenyl-2-ylcarbamic acid 1-[2-({3-[2-(3-hydroxybenzylamino)ethylcarbamoyl]benzoyl}methylamino)ethyl]piperidin-4-yl ester;
biphenyl-2-ylcarbamic acid 1-[2-({3-[2-(3-hydroxy-4-methoxybenzylamino)ethylcarbamoyl]benzoyl}methylamino)ethyl]piperidin-4-yl ester;
biphenyl-2-ylcarbamic acid 1-[2-({3-[2-(3,4-dihydroxybenzylamino)ethylcarbamoyl]benzoyl}methylamino)ethyl]piperidin-4-yl ester;
biphenyl-2-ylcarbamic acid 1-{2-[methyl(3-{2-[(thiophen-2-ylmethyl)amino]ethylcarbamoyl}benzoyl)amino]ethyl}piperidin-4-yl ester;
biphenyl-2-ylcarbamic acid 1-{2-[(3-{2-[(furan-2-ylmethyl)amino]ethylcarbamoyl}benzoyl)methylamino]ethyl}piperidin-4-yl ester;
biphenyl-2-ylcarbamic acid 1-{2-[(3-{2-[(1H-imidazol-2-ylmethyl)amino]ethylcarbamoyl}benzoyl)methylamino]ethyl}piperidin-4-yl ester;
biphenyl-2-ylcarbamic acid 1-{2-[(3-{2-[bis-(1H-imidazol-2-ylmethyl)amino]ethylcarbamoyl}benzoyl)methylamino]ethyl}piperidin-4-yl ester;
biphenyl-2-ylcarbamic acid 1-[2-({5-[2-(4-hydroxybenzylamino)ethylcarbamoyl]thiophene-2-carbonyl}methylamino)ethyl]piperidin-4-yl ester;
biphenyl-2-ylcarbamic acid 1-{2-[methyl-(5-{2-[(pyridin-4-ylmethyl)amino]ethylcarbamoyl}thiophene-2-carbonyl)amino]ethyl}piperidin-4-yl ester;
biphenyl-2-ylcarbamic acid 1-(2-{3-[3-(4-hydroxybenzylamino)propionylamino]benzoylamino}ethyl)piperidin-4-yl ester;
biphenyl-2-ylcarbamic acid 1-[2-(3-{3-[2-(4-hydroxyphenyl)ethylamino]propionylamino}benzoylamino)ethyl]piperidin-4-yl ester;
biphenyl-2-ylcarbamic acid 1-[2-({3-[3-(4-hydroxybenzylamino)propionylamino]benzoyl}methylamino)ethyl]piperidin-4-yl ester;
biphenyl-2-ylcarbamic acid 1-{2-[(3-{3-[2-(4-hydroxyphenyl)ethylamino]propionylamino}benzoyl)methylamino]ethyl}piperidin-4-yl ester;
biphenyl-2-ylcarbamic acid 1-[2-({3-[2-(4-hydroxybenzylamino)acetylamino]benzoyl}methylamino)ethyl]piperidin-4-yl ester;
biphenyl-2-ylcarbamic acid 1-{2-[(3-{2-[2-(4-hydroxyphenyl)ethylamino]acetylamino}benzoyl)methylamino]ethyl}piperidin-4-yl ester;
biphenyl-2-ylcarbamic acid 1-[2-(3-{2-[2-(4-hydroxyphenyl)ethylamino]acetylamino}benzoylamino)ethyl]piperidin-4-yl ester;
biphenyl-2-ylcarbamic acid 1-(2-{3-[2-(4-hydroxybenzylamino)ethylcarbamoyl]phenylcarbamoyl}ethyl)piperidin-4-yl ester;
biphenyl-2-ylcarbamic acid 1-(2-{3-[2-(4-hydroxy-3-methoxybenzylamino)ethylcarbamoyl]phenylcarbamoyl}ethyl)piperidin-4-yl ester;
biphenyl-2-ylcarbamic acid 1-(2-{3-[2-(2-hydroxybenzylamino)ethylcarbamoyl]phenylcarbamoyl}ethyl)piperidin-4-yl ester;
biphenyl-2-ylcarbamic acid 1-(2-{3-[3-(4-hydroxybenzylamino)propionylamino]phenylcarbamoyl}ethyl)piperidin-4-yl ester;
biphenyl-2-ylcarbamic acid 1-(2-{3-[3-(4-hydroxy-3-methoxybenzylamino)propionylamino]phenylcarbamoyl}ethyl)piperidin-4-yl ester;
biphenyl-2-ylcarbamic acid 1-(2-{3-[3-(2-hydroxybenzylamino)propionylamino]phenylcarbamoyl}ethyl)piperidin-4-yl ester;
biphenyl-2-ylcarbamic acid 1-(2-{methyl-[3-(3-pyrrolidin-1-ylpropionylamino)benzoyl]amino}ethyl)piperidin-4-yl ester;
biphenyl-2-ylcarbamic acid 1-{2-[3-(3-pyrrolidin-1-ylpropionylamino)benzoylamino]ethyl}piperidin-4-yl ester;
biphenyl-2-ylcarbamic acid 1-[2-({3-[3-(4-carbamoylpiperidin-1-yl)propionylamino]benzoyl}methylamino)ethyl]piperidin-4-yl ester;
biphenyl-2-ylcarbamic acid 1-(2-{3-[3-(4-carbamoylpiperidin-1-yl)propionylamino]benzoylamino}ethyl)piperidin-4-yl ester;
biphenyl-2-ylcarbamic acid 1-(2-{methyl[3-(2-pyrrolidin-1-yl-acetylamino)benzoyl]amino}ethyl)piperidin-4-yl ester;
biphenyl-2-ylcarbamic acid 1-[2-({3-[2-(4-hydroxypiperidin-1-yl)acetylamino]benzoyl}methylamino)ethyl]piperidin-4-yl ester;
biphenyl-2-ylcarbamic acid 1-{2-[3-(2-pyrrolidin-1-ylacetylamino)benzoylamino]ethyl}piperidin-4-yl ester;
biphenyl-2-ylcarbamic acid 1-(2-{3-[2-(4-hydroxypiperidin-1-yl)acetylamino]benzoylamino}ethyl)piperidin-4-yl ester;
biphenyl-2-ylcarbamic acid 1-(2-{3-[2-(4-carbamoylpiperidin-1-yl)acetylamino]benzoylamino}ethyl)piperidin-4-yl ester;

biphenyl-2-ylcarbamic acid 1-(2-{3-[2-(cyclopropylmethylamino)ethylcarbamoyl]phenylcarbamoyl}ethyl)piperidin-4-yl ester;

biphenyl-2-ylcarbamic acid 1-[2-(3-{3-(cyclopropylmethylamino)propionylamino]phenylcarbamoyl}ethyl)piperidin-4-yl ester;

biphenyl-2-ylcarbamic acid 1-[2-(3-{2-[(1H-imidazol-2-ylmethyl)amino]ethylcarbamoyl}phenylcarbamoyl)ethyl]piperidin-4-yl ester;

biphenyl-2-ylcarbamic acid 1-[2-(3-{3-[(1H-imidazol-2-ylmethyl)amino]propionylamino}phenylcarbamoyl)ethyl]piperidin-4-yl ester;

biphenyl-2-ylcarbamic acid 1-[2-(3-{2-[(furan-2-ylmethyl)amino]ethylcarbamoyl}phenylcarbamoyl)ethyl]piperidin-4-yl ester;

biphenyl-2-ylcarbamic acid 1-[2-(3-{3-[(furan-2-ylmethyl)amino]propionylamino}phenylcarbamoyl)ethyl]piperidin-4-yl ester;

biphenyl-2-ylcarbamic acid 1-(2-{-[3-(3-cyclopropylaminopropionylamino)benzoyl]methylamino}ethyl)piperidin-4-yl ester;

biphenyl-2-ylcarbamic acid 1-{2-[3-(3-cyclopropylaminopropionylamino)benzoylamino]ethyl}piperidin-4-yl ester;

biphenyl-2-ylcarbamic acid 1-(2-{methyl-[3-(3-methylaminopropionylamino)benzoyl]amino}ethyl)piperidin-4-yl ester;

biphenyl-2-ylcarbamic acid 1-{2-[3-(3-methylaminopropionylamino)benzoylamino]ethyl}piperidin-4-yl ester;

biphenyl-2-ylcarbamic acid 1-(2-{3-[2-(2-hydroxyethylamino)acetylamino]benzoylamino}ethyl)piperidin-4-yl ester;

biphenyl-2-ylcarbamic acid 1-(2-{3-[2-(carbamoylmethylamino)acetylamino]benzoylamino}ethyl)piperidin-4-yl ester;

biphenyl-2-ylcarbamic acid 1-[2-(methyl-{3-[2-(3-oxopiperazin-1-yl)acetylamino]benzoyl}amino)ethyl]piperidin-4-yl ester;

biphenyl-2-ylcarbamic acid 1-[2-({3-[2-(cyclopropylmethylamino)acetylamino]benzoyl}methylamino)ethyl]piperidin-4-yl ester;

biphenyl-2-ylcarbamic acid 1-(2-{methyl-[3-(2-methylaminoacetylamino)benzoyl]amino}ethyl)piperidin-4-yl ester;

biphenyl-2-ylcarbamic acid 1-(2-{-[3-(2-ethylaminoacetylamino)benzoyl]methylamino}ethyl)piperidin-4-yl ester;

biphenyl-2-ylcarbamic acid 1-(2-{-[3-(2-cyclopropylaminoacetylamino)benzoyl]methylamino}ethyl)piperidin-4-yl ester;

biphenyl-2-ylcarbamic acid 1-[2-({3-[2-(2-hydroxyethylamino)acetylamino]benzoyl}methylamino)ethyl]piperidin-4-yl ester;

biphenyl-2-ylcarbamic acid 1-(2-{3-[2-(cyclopropylmethylamino)acetylamino]benzoylamino}ethyl)piperidin-4-yl ester;

biphenyl-2-ylcarbamic acid 1-[2-({3-[2-(cyclopropylmethylamino)ethylcarbamoyl]benzoyl}methylamino)ethyl]piperidin-4-yl ester;

biphenyl-2-ylcarbamic acid 1-{2-[3-(2-methylaminoacetylamino)benzoylamino]ethyl}piperidin-4-yl ester;

biphenyl-2-ylcarbamic acid 1-{2-[3-(2-ethylaminoacetylamino)benzoylamino]ethyl}piperidin-4-yl ester;

biphenyl-2-ylcarbamic acid 1-{2-[3-(2-cyclopropylaminoacetylamino)benzoylamino]ethyl}piperidin-4-yl ester;

biphenyl-2-ylcarbamic acid 1-(2-{methyl-[3-(2-methylaminoethylcarbamoyl)benzoyl]amino}ethyl)piperidin-4-yl ester;

biphenyl-2-ylcarbamic acid 1-[2-({3-[2-(2-hydroxyethylamino)ethylcarbamoyl]benzoyl}methylamino)ethyl]piperidin-4-yl ester; and biphenyl-2-ylcarbamic acid 1-{2-[(3-{2-[2-(4-hydroxyphenyl)ethylamino]ethylcarbamoyl}benzoyl)methylamino]ethyl}piperidin-4-yl ester;

or a pharmaceutically acceptable salt or solvate thereof.

Of particular interest are the following compounds having formula Ia:

biphenyl-2-ylcarbamic acid 1-[2-({3-[2-(4-hydroxybenzylamino)ethylcarbamoyl]benzoyl}methylamino)ethyl]piperidin-4-yl ester;

biphenyl-2-ylcarbamic acid 1-[2-({3-[2-(4-hydroxy-3-methoxybenzylamino)ethylcarbamoyl]benzoyl}methylamino)ethyl]piperidin-4-yl ester;

biphenyl-2-ylcarbamic acid 1-[2-({3-[2-(2-hydroxybenzylamino)ethylcarbamoyl]benzoyl}methylamino)ethyl]piperidin-4-yl ester;

biphenyl-2-ylcarbamic acid 1-[2-({3-[2-(4-methoxybenzylamino)ethylcarbamoyl]benzoyl}methylamino)ethyl]piperidin-4-yl ester;

biphenyl-2-ylcarbamic acid 1-(2-{3-[2-(4-hydroxy-2-methoxybenzylamino)ethylcarbamoyl]benzoylamino}ethyl)piperidin-4-yl ester;

biphenyl-2-ylcarbamic acid 1-(2-{3-[2-(2-hydroxybenzylamino)ethylcarbamoyl]benzoylamino}ethyl)piperidin-4-yl ester;

biphenyl-2-ylcarbamic acid 1-(2-{3-[2-(4-methoxybenzylamino)ethylcarbamoyl]benzoylamino}ethyl)piperidin-4-yl ester;

biphenyl-2-ylcarbamic acid 1-[2-({3-[2-(3-hydroxybenzylamino)ethylcarbamoyl]benzoyl}methylamino)ethyl]piperidin-4-yl ester;

biphenyl-2-ylcarbamic acid 1-[2-({3-[2-(3-hydroxy-4-methoxybenzylamino)ethylcarbamoyl]benzoyl}methylamino)ethyl]piperidin-4-yl ester;

biphenyl-2-ylcarbamic acid 1-[2-({3-[2-(3,4-dihydroxybenzylamino)ethylcarbamoyl]benzoyl}methylamino)ethyl]piperidin-4-yl ester;

biphenyl-2-ylcarbamic acid 1-[2-({5-[2-(4-hydroxybenzylamino)ethylcarbamoyl]thiophene-2-carbonyl}methylamino)ethyl]piperidin-4-yl ester; and biphenyl-2-ylcarbamic acid 1-{2-[(3-{2-[2-(4-hydroxyphenyl)ethylamino]ethylcarbamoyl}benzoyl)methylamino]ethyl}piperidin-4-yl ester;

or a pharmaceutically acceptable salt or solvate thereof.

Of particular interest are the following compounds having formula Ib:

biphenyl-2-ylcarbamic acid 1-(2-{3-[3-(4-hydroxybenzylamino)propionylamino]benzoylamino}ethyl)piperidin-4-yl ester;

biphenyl-2-ylcarbamic acid 1-[2-(3-{3-[2-(4-hydroxyphenyl)ethylamino]propionylamino}benzoylamino)ethyl]piperidin-4-yl ester;

biphenyl-2-ylcarbamic acid 1-[2-({3-[3-(4-hydroxybenzylamino)propionylamino]benzoyl}methylamino)ethyl]piperidin-4-yl ester;

biphenyl-2-ylcarbamic acid 1-{2-[(3-{3-[2-(4-hydroxyphenyl)ethylamino]propionylamino}benzoyl)methylamino]ethyl}piperidin-4-yl ester;

biphenyl-2-ylcarbamic acid 1-[2-({3-[2-(4-hydroxybenzylamino)acetylamino]benzoyl}methylamino)ethyl]piperidin-4-yl ester;

biphenyl-2-ylcarbamic acid 1-{2-[(3-{2-[2-(4-hydroxyphenyl)ethylamino]acetylamino}benzoyl)methylamino]ethyl}piperidin-4-yl ester;

biphenyl-2-ylcarbamic acid 1-[2-(3-{2-[2-(4-hydroxyphenyl)ethylamino]acetylamino}benzoylamino)ethyl]piperidin-4-yl ester;
biphenyl-2-ylcarbamic acid 1-(2-{3-[2-(4-hydroxybenzylamino)ethylcarbamoyl]phenylcarbamoyl}ethyl)piperidin-4-yl ester;
biphenyl-2-ylcarbamic acid 1-(2-{3-[2-(4-hydroxy-3-methoxybenzylamino)ethylcarbamoyl]phenylcarbamoyl}ethyl)piperidin-4-yl ester;
biphenyl-2-ylcarbamic acid 1-(2-{3-[2-(2-hydroxybenzylamino)ethylcarbamoyl]phenylcarbamoyl}ethyl)piperidin-4-yl ester;
biphenyl-2-ylcarbamic acid 1-(2-{3-[3-(4-hydroxybenzylamino)propionylamino]phenylcarbamoyl}ethyl)piperidin-4-yl ester;
biphenyl-2-ylcarbamic acid 1-(2-{3-[3-(4-hydroxy-3-methoxybenzylamino)propionylamino]phenylcarbamoyl}ethyl)piperidin-4-yl ester; and
biphenyl-2-ylcarbamic acid 1-(2-{3-[3-(2-hydroxybenzylamino)propionylamino]phenylcarbamoyl}ethyl)piperidin-4-yl ester;
or a pharmaceutically acceptable salt or solvate thereof.

Of particular interest are the following compounds having formula Ic:

biphenyl-2-ylcarbamic acid 1-{2-[methyl(3-{2-[(thiophen-2-ylmethyl)amino]ethylcarbamoyl}benzoyl)amino]ethyl}piperidin-4-yl ester;
biphenyl-2-ylcarbamic acid 1-{2-[(3-{2-[(furan-2-ylmethyl)amino]ethylcarbamoyl}benzoyl)methylamino]ethyl}piperidin-4-yl ester;
biphenyl-2-ylcarbamic acid 1-{2-[(3-{2-[(1H-imidazol-2-ylmethyl)amino]ethylcarbamoyl}benzoyl)methylamino]ethyl}piperidin-4-yl ester;
biphenyl-2-ylcarbamic acid 1-{2-[(3-{2-[bis-(1H-imidazol-2-ylmethyl)amino]ethylcarbamoyl}benzoyl)methylamino]ethyl}piperidin-4-yl ester;
biphenyl-2-ylcarbamic acid 1-{2-[methyl-(5-{2-[(pyridin-4-ylmethyl)amino]ethylcarbamoyl}thiophene-2-carbonyl)amino]ethyl}piperidin-4-yl ester;
biphenyl-2-ylcarbamic acid 1-(2-{methyl-[3-(3-pyrrolidin-1-ylpropionylamino)benzoyl]amino}ethyl)piperidin-4-yl ester;
biphenyl-2-ylcarbamic acid 1-{2-[3-(3-pyrrolidin-1-ylpropionylamino)benzoylamino]ethyl}piperidin-4-yl ester;
biphenyl-2-ylcarbamic acid 1-[2-({3-[3-(4-carbamoylpiperidin-1-yl)propionylamino]benzoyl}methylamino)ethyl]piperidin-4-yl ester;
biphenyl-2-ylcarbamic acid 1-(2-{3-[3-(4-carbamoylpiperidin-1-yl)propionylamino]benzoylamino}ethyl)piperidin-4-yl ester;
biphenyl-2-ylcarbamic acid 1-(2-{methyl[3-(2-pyrrolidin-1-yl-acetylamino)benzoyl]amino}ethyl)piperidin-4-yl ester;
biphenyl-2-ylcarbamic acid 1-[2-({3-[2-(4-hydroxypiperidin-1-yl)acetylamino]benzoyl}methylamino)ethyl]piperidin-4-yl ester;
biphenyl-2-ylcarbamic acid 1-{2-[3-(2-pyrrolidin-1-ylacetylamino)benzoylamino]ethyl}piperidin-4-yl ester;
biphenyl-2-ylcarbamic acid 1-(2-{3-[2-(4-hydroxypiperidin-1-yl)acetylamino]benzoylamino}ethyl)piperidin-4-yl ester;
biphenyl-2-ylcarbamic acid 1-(2-{3-[2-(4-carbamoylpiperidin-1-yl)acetylamino]benzoylamino}ethyl)piperidin-4-yl ester;
biphenyl-2-ylcarbamic acid 1-(2-{3-[2-(cyclopropylmethylamino)ethylcarbamoyl]phenylcarbamoyl}ethyl)piperidin-4-yl ester;
biphenyl-2-ylcarbamic acid 1-(2-{3-[3-(cyclopropylmethylamino)propionylamino]phenylcarbamoyl}ethyl)piperidin-4-yl ester;
biphenyl-2-ylcarbamic acid 1-[2-(3-{2-[(1H-imidazol-2-ylmethyl)amino]ethylcarbamoyl}phenylcarbamoyl)ethyl]piperidin-4-yl ester;
biphenyl-2-ylcarbamic acid 1-[2-(3-{3-[(1H-imidazol-2-ylmethyl)amino]propionylamino}phenylcarbamoyl)ethyl]piperidin-4-yl ester;
biphenyl-2-ylcarbamic acid 1-[2-(3-{2-[(furan-2-ylmethyl)amino]ethylcarbamoyl}phenylcarbamoyl)ethyl]piperidin-4-yl ester;
biphenyl-2-ylcarbamic acid 1-[2-(3-{3-[(furan-2-ylmethyl)amino]propionylamino}phenylcarbamoyl)ethyl]piperidin-4-yl ester;
biphenyl-2-ylcarbamic acid 1-(2-{-[3-(3-cyclopropylaminopropionylamino)benzoyl]methylamino}ethyl)piperidin-4-yl ester;
biphenyl-2-ylcarbamic acid 1-{2-[3-(3-cyclopropylaminopropionylamino)benzoylamino]ethyl}piperidin-4-yl ester;
biphenyl-2-ylcarbamic acid 1-(2-{methyl-[3-(3-methylaminopropionylamino)benzoyl]amino}ethyl)piperidin-4-yl ester;
biphenyl-2-ylcarbamic acid 1-{2-[3-(3-methylaminopropionylamino)benzoylamino]ethyl}piperidin-4-yl ester;
biphenyl-2-ylcarbamic acid 1-(2-{3-[2-(2-hydroxyethylamino)acetylamino]benzoylamino}ethyl)piperidin-4-yl ester;
biphenyl-2-ylcarbamic acid 1-(2-{3-[2-(carbamoylmethylamino)acetylamino]benzoylamino}ethyl)piperidin-4-yl ester;
biphenyl-2-ylcarbamic acid 1-[2-(methyl-{3-[2-(3-oxopiperazin-1-yl)acetylamino]benzoyl}amino)ethyl]piperidin-4-yl ester;
biphenyl-2-ylcarbamic acid 1-[2-({3-[2-(cyclopropylmethylamino)acetylamino]benzoyl}methylamino)ethyl]piperidin-4-yl ester;
biphenyl-2-ylcarbamic acid 1-(2-{methyl-[3-(2-methylaminoacetylamino)benzoyl]amino}ethyl)piperidin-4-yl ester;
biphenyl-2-ylcarbamic acid 1-(2-{-[3-(2-ethylaminoacetylamino)benzoyl]methylamino}ethyl)piperidin-4-yl ester;
biphenyl-2-ylcarbamic acid 1-(2-{-[3-(2-cyclopropylaminoacetylamino)benzoyl]methylamino}ethyl)piperidin-4-yl ester;
biphenyl-2-ylcarbamic acid 1-[2-({3-[2-(2-hydroxyethylamino)acetylamino]benzoyl}methylamino)ethyl]piperidin-4-yl ester;
biphenyl-2-ylcarbamic acid 1-(2-{3-[2-(cyclopropylmethylamino)acetylamino]benzoylamino}ethyl)piperidin-4-yl ester;
biphenyl-2-ylcarbamic acid 1-[2-({3-[2-(cyclopropylmethylamino)ethylcarbamoyl]benzoyl}methylamino)ethyl]piperidin-4-yl ester;
biphenyl-2-ylcarbamic acid 1-{2-[3-(2-methylaminoacetylamino)benzoylamino]ethyl}piperidin-4-yl ester;
biphenyl-2-ylcarbamic acid 1-{2-[3-(2-ethylaminoacetylamino)benzoylamino]ethyl}piperidin-4-yl ester;
biphenyl-2-ylcarbamic acid 1-{2-[3-(2-cyclopropylaminoacetylamino)benzoylamino]ethyl}piperidin-4-yl ester;
biphenyl-2-ylcarbamic acid 1-(2-{methyl-[3-(2-methylaminoethylcarbamoyl)benzoyl]amino}ethyl)piperidin-4-yl ester; and
biphenyl-2-ylcarbamic acid 1-[2-({3-[2-(2-hydroxyethylamino)ethylcarbamoyl]benzoyl}methylamino)ethyl]piperidin-4-yl ester;
or a pharmaceutically acceptable salt or solvate thereof.

Particular compounds of formula Ia' that are of interest include:

biphenyl-2-ylcarbamic acid 1-(2-{-[3-(2-aminoethylcarbamoyl)benzoyl]methylamino}ethyl)piperidin-4-yl ester;

biphenyl-2-ylcarbamic acid 1-(2-{[6-(2-aminoethylcarbamoyl)pyridine-2-carbonyl]methylamino}ethyl)piperidin-4-yl ester;

biphenyl-2-ylcarbamic acid 1-(2-{[5-(2-aminoethylcarbamoyl)pyridine-3-carbonyl]methylamino}ethyl)piperidin-4-yl ester;

biphenyl-2-ylcarbamic acid 1-(2-{[6-(2-aminoethylcarbamoyl)pyridine-3-carbonyl]methylamino}ethyl)piperidin-4-yl ester;

biphenyl-2-ylcarbamic acid 1-(2-{[5-(2-aminoethylcarbamoyl)thiophene-2-carbonyl]methylamino}ethyl)piperidin-4-yl ester;

biphenyl-2-ylcarbamic acid 1-(2-{[5-(2-aminoethylcarbamoyl)furan-2-carbonyl]methylamino}ethyl)piperidin-4-yl ester;

biphenyl-2-ylcarbamic acid 1-(2-{[4-(2-aminoethylcarbamoyl)benzoyl]methylamino}ethyl)piperidin-4-yl ester;

biphenyl-2-ylcarbamic acid 1-{2-[3-(2-aminoethylcarbamoyl)benzoylamino]ethyl}piperidin-4-yl ester; and biphenyl-2-ylcarbamic acid 1-(2-{[5-(3-aminopropylcarbamoyl)thiophene-2-carbonyl]methylamino}ethyl)piperidin-4-yl ester;

or a pharmaceutically acceptable salt or solvate thereof.

Definitions

When describing the compounds, compositions, methods and processes of the invention, the following terms have the following meanings unless otherwise indicated.

The term "alkyl" means a monovalent saturated hydrocarbon group which may be linear or branched. Unless otherwise defined, such alkyl groups typically contain from 1 to 10 carbon atoms. Representative alkyl groups include, by way of example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "alkylene" means a divalent saturated hydrocarbon group which may be linear or branched. Unless otherwise defined, such alkylene groups typically contain from 1 to 10 carbon atoms. Representative alkylene groups include, by way of example, methylene, ethane-1,2-diyl ("ethylene"), propane-1,2-diyl, propane-1,3-diyl, butane-1,4-diyl, pentane-1,5-diyl and the like.

The term "alkoxy" means a monovalent group of the formula (alkyl)-O—, where alkyl is as defined herein. Representative alkoxy groups include, by way of example, methoxy, ethoxy, n-propoxy, isopropoxy, n-butoxy, sec-butoxy, isobutoxy, tert-butoxy and the like.

The term "alkenyl" means a monovalent unsaturated hydrocarbon group which may be linear or branched and which has at least one, and typically 1, 2 or 3, carbon-carbon double bonds. Unless otherwise defined, such alkenyl groups typically contain from 2 to 10 carbon atoms. Representative alkenyl groups include, by way of example, ethenyl, n-propenyl, isopropenyl, n-but-2-enyl, n-hex-3-enyl and the like. The term "alkenylene" means a divalent alkenyl group.

The term "alkynyl" means a monovalent unsaturated hydrocarbon group which may be linear or branched and which has at least one, and typically 1, 2 or 3, carbon-carbon triple bonds. Unless otherwise defined, such alkynyl groups typically contain from 2 to 10 carbon atoms. Representative alkynyl groups include, by way of example, ethynyl, n-propynyl, n-but-2-ynyl, n-hex-3-ynyl and the like. The term "alkynylene" means a divalent alkynyl group.

The term "aryl" means a monovalent aromatic hydrocarbon having a single ring (i.e., phenyl) or fused rings (i.e., naphthalene). Unless otherwise defined, such aryl groups typically contain from 6 to 10 carbon ring atoms. Representative aryl groups include, by way of example, phenyl and naphthalene-1-yl, naphthalene-2-yl, and the like. The term "arylene" means a divalent aryl group.

The term "azacycloalkyl" means a monovalent heterocyclic ring containing one nitrogen atom, i.e., a cycloalkyl group in which one carbon atom has been replaced with a nitrogen atom. Unless otherwise defined, such azacycloalkyl groups typically contain from 2 to 9 carbon atoms. Representative examples of an azacycloalkyl group are pyrrolidinyl and piperidinyl groups. The term "azacycloalkylene" means a divalent azacycloakyl group. Representative examples of an azacycloalkylene group are pyrrolidinylene and piperidinylene groups.

The term "cycloalkyl" means a monovalent saturated carbocyclic hydrocarbon group. Unless otherwise defined, such cycloalkyl groups typically contain from 3 to 10 carbon ring atoms. Representative cycloalkyl groups include, by way of example, cyclopropyl, cyclobutyl, cyclopentyl, cyclohexyl and the like. The term "cycloalkylene" means a divalent cycloalkyl group.

The term "halo" means fluoro, chloro, bromo and iodo.

The term "heteroaryl" means a monovalent aromatic group having a single ring or two fused rings and containing in the ring at least one heteroatom (typically 1 to 3 heteroatoms) selected from nitrogen, oxygen and sulfur. Unless otherwise defined, such heteroaryl groups typically contain from 5 to 10 total ring atoms. Representative heteroaryl groups include, by way of example, monovalent species of pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like, where the point of attachment is at any available carbon or nitrogen ring atom. The term "heteroarylene" means a divalent heteroaryl group.

The term "heterocyclyl" or "heterocyclic" means a monovalent saturated or unsaturated (non-aromatic) group having a single ring or multiple condensed rings and containing in the ring at least one heteroatom (typically 1 to 3 heteroatoms) selected from nitrogen, oxygen and sulfur. Unless otherwise defined, such heterocyclic groups typically contain from 2 to 9 total ring carbon atoms. Representative heterocyclic groups include, by way of example, monovalent species of pyrrolidine, imidazolidine, pyrazolidine, piperidine, 1,4-dioxane, morpholine, thiomorpholine, piperazine, 3-pyrroline and the like, where the point of attachment is at any available carbon or nitrogen ring atom. The term "heterocyclene" means a divalent heterocyclyl or heterocyclic group.

When a specific number of carbon atoms is intended for a particular term used herein, the number of carbon atoms is shown in parentheses preceding the term. For example, the term "(1-4C)alkyl" means an alkyl group having from 1 to 4 carbon atoms.

The term "pharmaceutically acceptable salt" means a salt which is acceptable for administration to a patient such as a mammal (e.g., salts having acceptable mammalian safety for a given dosage regime). Such salts can be derived from pharmaceutically acceptable inorganic or organic bases and from pharmaceutically acceptable inorganic or organic acids. Salts derived from pharmaceutically acceptable inorganic bases include ammonium, calcium, copper, ferric, ferrous, lithium, magnesium, manganic, manganous, potassium, sodium, zinc and the like. Particularly preferred are ammonium, calcium, magnesium, potassium and sodium salts. Salts derived from pharmaceutically acceptable organic bases include salts of primary, secondary and tertiary amines, including substituted amines, cyclic amines, naturally-occurring amines and the like such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. Salts derived from pharmaceutically acceptable acids include acetic, ascorbic, benzenesulfonic, benzoic, camphosulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic, xinafoic and the like. Particularly preferred are citric, hydrobromic, hydrochloric, isethionic, maleic, naphthalene-1,5-disulfonic, phosphoric, sulfuric and tartaric acids.

The term "salt thereof" means a compound formed when the hydrogen of an acid is replaced by a cation such as a metal cation or an organic cation and the like. Preferably, the salt is a pharmaceutically acceptable salt. This is not required however, since some salts (e.g., salts of intermediate compounds) are not intended to be administered to patients.

The term "solvate" means a complex or aggregate formed by one or more molecules of a solute, i.e. a compound of formula I or a pharmaceutically acceptable salt thereof, and one or more molecules of a solvent. Such solvates are typically crystalline solids having a substantially fixed molar ratio of solute and solvent. Representative solvents include, by way of example, water, methanol, ethanol, isopropanol, acetic acid and the like. When the solvent is water, the solvate formed is a hydrate.

It will be appreciated that the term "or a pharmaceutically acceptable salt or solvate or stereoisomer thereof" is intended to include all permutations of salts, solvates and stereoisomers such as a solvate of a pharmaceutically acceptable salt of a stereoisomer of a compound of formula I.

The term "therapeutically effective amount" means an amount sufficient to effect treatment when administered to a patient in need of treatment. For example, a therapeutically effective amount for antagonizing a muscarinic receptor is that amount which will achieve the desired antagonizing effect. Similarly, a therapeutically effective amount for treating a pulmonary disorder is that amount that will achieve the desired therapeutic result, which may be disease prevention, amelioration, suppression or alleviation, as described below.

The term "treating" or "treatment" as used herein means the treating or treatment of a disease or medical condition (such as COPD) in a patient such as a mammal (particularly a human) that includes:
  (a) preventing the disease or medical condition from occurring, i.e., prophylactic treatment of a patient believed to be at risk of contracting or being pre-disposed to such disease or medical condition;
  (b) ameliorating the disease or medical condition, i.e., eliminating or causing regression of the disease or medical condition in a patient having such disease or medical condition;
  (c) suppressing the disease or medical condition, i.e., slowing or arresting the development of the disease or medical condition in a patient having such disease or medical condition; or
  (d) alleviating the symptoms of the disease or medical condition in a patient having such disease or medical condition.

The term "unit dosage form" refers to a physically discrete unit suitable for dosing a patient, i.e., each unit containing a predetermined quantity of a compound of the invention calculated to produce the desired therapeutic effect either alone or in combination with one or more additional units. For example, such unit dosage forms may be capsules, tablets, pills, and the like.

The term "pharmaceutically acceptable" refers to a material that is not biologically or otherwise undesirable. For example, the term "pharmaceutically acceptable carrier" refers to a material that can be incorporated into a composition and administered to a patient without causing undesirable biological effects or interacting in a deleterious manner with other components of the composition. Such pharmaceutically acceptable materials typically have met the required standards of toxicological and manufacturing testing, and include those materials identified as suitable inactive ingredients by the U.S. Food and Drug administration.

The term "leaving group" means a functional group or atom which can be displaced by another functional group or atom in a substitution reaction such as a nucleophilic substitution reaction. By way of example, representative leaving groups include chloro, bromo and iodo groups; sulfonic ester groups such as mesylate, tosylate, brosylate, nosylate and the like; and acyloxy groups such as acetoxy, trifluoroacetoxy and the like.

The term "protected derivatives thereof" means a derivative of the specified compound in which one or more functional groups of the compound are protected from undesired reactions with a protecting or blocking group. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

The term "amino-protecting group" means a protecting group suitable for preventing undesired reactions at an amino group. Representative amino-protecting groups include, but are not limited to, tert-butoxycarbonyl (BOC), trityl (Tr), benzyloxycarbonyl (Cbz), 9-fluorenylmethoxycarbonyl (Fmoc), formyl, trimethylsilyl (TMS), tert-butyldimethylsilyl (TBS), and the like.

The term "carboxy-protecting group" means a protecting group suitable for preventing undesired reactions at a carboxy group. Representative carboxy-protecting groups include, but are not limited to, esters such as methyl, ethyl, tert-butyl, benzyl (Bn), p-methoxybenzyl (PMB), 9-fluoroenylmethyl (Fm), trimethylsilyl (TMS), tert-butyldimethylsilyl (TBS), diphenylmethyl (benzhydryl, DPM) and the like.

The term "hydroxyl-protecting group" means a protecting group suitable for preventing undesirable reactions at a hydroxyl group. Representative hydroxyl-protecting groups include, but are not limited to, silyl groups including tri(1-6C)alkylsilyl groups such as trimethylsilyl (TMS), triethylsilyl (TES), tert-butyldimethylsilyl (TBS) and the like; esters (acyl groups) including (1-6C)alkanoyl groups such as formyl, acetyl and the like; arylmethyl groups such as benzyl (Bn), p-methoxybenzyl (PMB), 9-fluorenylmethyl (Fm), diphenylmethyl (benzhydryl, DPM) and the like. Additionally, two hydroxyl groups can also be protected as an alkylidene group such as prop-2-ylidine, formed, for example, by reaction with a ketone such as acetone.

General Synthetic Procedures

The biphenyl compounds of the invention can be prepared from readily available starting materials using the following general methods, the procedures set forth in the Examples, or by using other methods, reagents, and starting materials that are readily available to those of ordinary skill in the art. Although a particular embodiment of the present invention may be shown or described herein, those skilled in the art will recognize that all embodiments or aspects of the present invention can be readily prepared. It will also be appreciated that where typical or preferred process conditions (i.e., reaction temperatures, times, mole ratios of reactants, solvents, pressures, etc.) are given, other process conditions can also be used unless otherwise stated. While the optimum reaction conditions may vary depending on the particular reactants or solvent used, such conditions can be readily determined by one skilled in the art by routine optimization procedures.

Additionally, as will be apparent to those skilled in the art, conventional protecting groups may be necessary or desired to prevent certain functional groups from undergoing undesired reactions. The choice of a suitable protecting group for a particular functional group as well as suitable conditions for protection and deprotection of such functional groups are well-known in the art. Protecting groups other than those illustrated in the procedures described herein may be used, if desired. For example, numerous protecting groups, and their introduction and removal, are described in T. W. Greene and G. M. Wuts, *Protecting Groups in Organic Synthesis*, Third Edition, Wiley, New York, 1999, and references cited therein.

By way of illustration, the compounds of the invention can be prepared by one or more of the following exemplary processes. Compounds of formulas I, Ia-c and Ia' can be prepared by (a) reacting a compound of formula II:

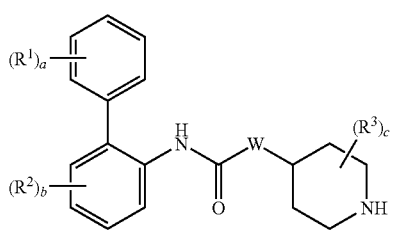

II or a salt thereof, with a compound of formula III:

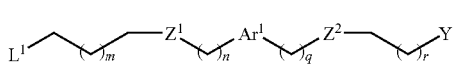

III wherein $L^1$ represents a leaving group.

Compounds of formulas I and Ib-c can also be prepared by (b) coupling a compound of formula IVa:

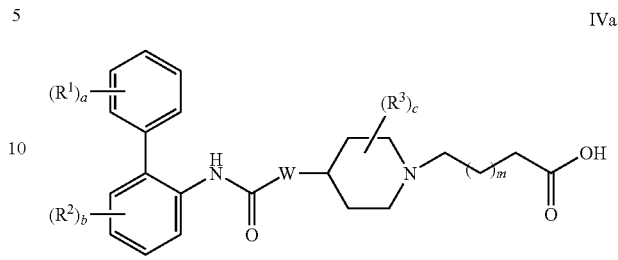

IVa or a reactive derivative thereof, with a compound of formula Va:

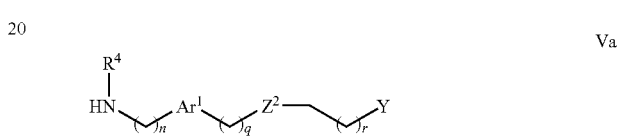

Va or (b') coupling a compound of formula IVb:

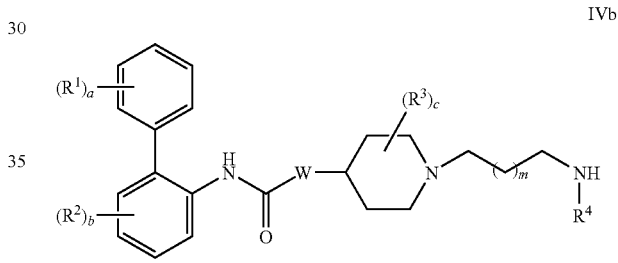

IVb with a compound of formula Vb:

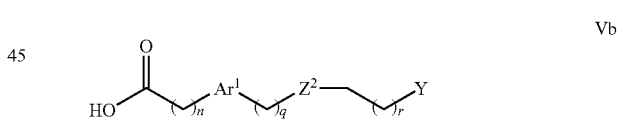

Vb or a reactive derivative thereof. Compounds of formula Ia and Ia' can be prepared by coupling a compound of formula IVb with a compound of formula Vb or a reactive derivative thereof.

Compounds of formulas I, Ia-c and Ia' can also be prepared by (c) coupling a compound of formula VIa:

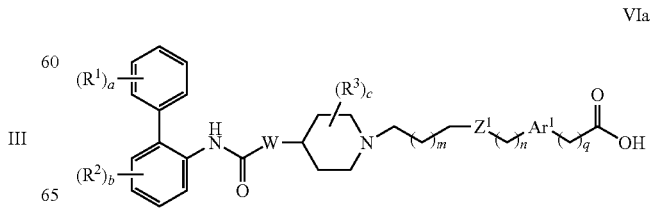

VIa or a reactive derivative thereof, with a compound of formula VIIa:

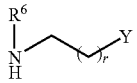
VIIa

Compounds of formulas I and Ib-c can also be prepared by (c') coupling a compound of formula VIb:

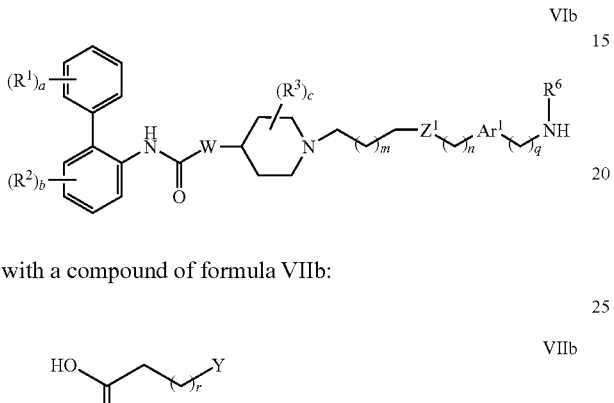
VIb with a compound of formula VIIb:

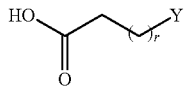
VIIb or a reactive derivative thereof.

Compounds of formulas I, Ia-c and Ia' can be prepared by (d) reacting a compound of formula VIII:

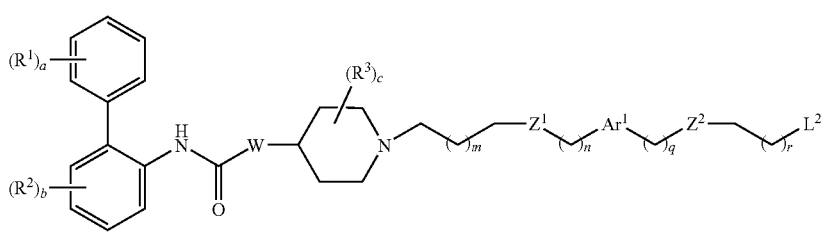
VIII wherein $L^2$ represents a leaving group, with a compound of formula IX:

H—Y  IX where H—Y is:

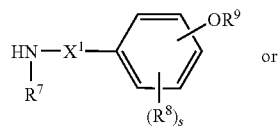

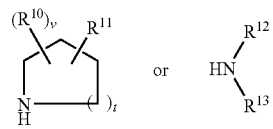

depending upon which compound is being prepared, i.e., a compound of formula I, formula Ia, formula Ib or formula Ic.

For preparing compound of formula Ia', H—Y is —$NH_2$ or a protected form thereof.

Compounds of formulas I, Ia-c and Ia' can also be prepared by (e) reacting a compound of formula II with a compound of formula X:

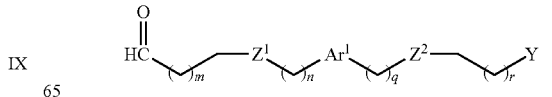
X in the presence of a reducing agent; or

Compounds of formulas I, Ia-c and Ia' can also be prepared by (f) reacting a compound of formula XI:

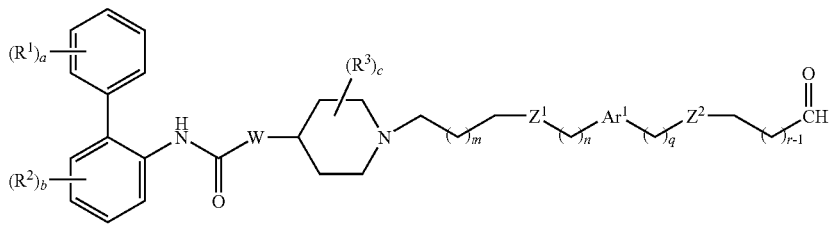

XI with a compound of formula IX in the presence of a reducing agent.

Any of the aforementioned processes may also involve a step of (g) removing any protecting groups that may be present to provide a compound of the invention (formulas I, Ia, Ib, Ic, or Ia'), and optionally forming a pharmaceutically acceptable salt thereof.

Generally, if a salt of one of the starting materials is used in the processes described above, such as an acid addition salt, the salt is typically neutralized before or during the reaction process. This neutralization reaction is typically accomplished by contacting the salt with one molar equivalent of a base for each molar equivalent of acid addition salt.

The $Z^1$, $Z^2$ and Y substituents in the intermediates described in the above processes, will vary depending upon whether compounds of formula I, formula Ia, formula Ib, formula Ic, or formula Ia' are being prepared. For use in preparing compounds of formulas I, Ib, and Ic, the $Z^1$ substituent in any intermediate will be —C(O)N($R^4$)— or —N($R^4$)C(O)— and $Z^2$ will be —C(O)N($R^6$)— or —N($R^6$)C(O)—. For preparing compounds of formula Ia or Ia', the $Z^1$ substituent in any intermediate will be —N($R^4$)C(O)—, and the $Z^2$ substituent will be —C(O)N($R^6$)—. For use in preparing compounds of formula I, the Y substituent in any intermediate will be:

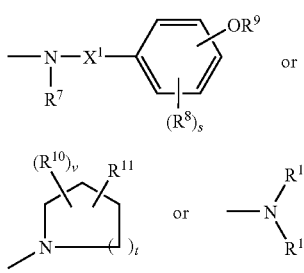

For use in preparing compounds of formula Ia, and Ib, the Y substituent in any intermediate will be:

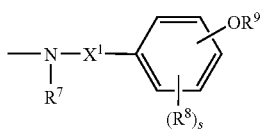

For use in preparing compounds of formula Ic, the Y substituent in any intermediate will be

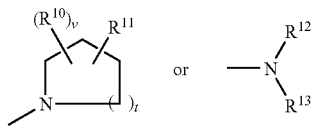

For use in preparing compounds of formula Ia', the Y substituent in any intermediate will be —$NH_2$, or a protected form thereof.

In process (a), the reaction between the compounds of formula II and III, the leaving represented by $L^1$ can be, for example, a halo group such as chloro, bromo or iodo, or a sulfonic ester group such as mesylate or tosylate. The reaction is conveniently performed in the presence of a base, for example, a tertiary amine such as diisopropylethylamine. Convenient solvents include nitriles such as acetonitrile. The reaction is conveniently conducted at a temperature in the range of from 0 to 100° C.

Compounds of formula II are generally known in the art, or can be prepared by deprotecting a compound of formula XII:

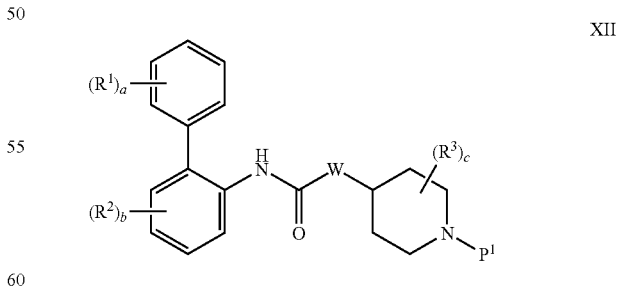

XII where $P^1$ represents an amino-protecting group such as a benzyl group. Benzyl groups are conveniently removed by reduction, using a hydrogen or ammonium formate and a Group VIII metal catalyst such as palladium. When W represents $NW^a$, the hydrogenation reaction is conveniently performed using Pearlman's catalyst (Pd(OH)$_2$).

Compounds of formula XII can be prepared by reacting an isocyanate compound of formula XIII:

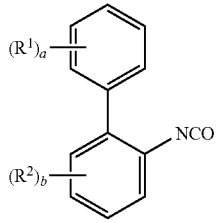

XIII with a compound of formula XIV:

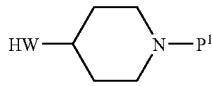

XIV

Compounds of formula III can be prepared starting from a corresponding compound in which $L^1$ represents a hydroxyl group, for example, by reaction of a halogenating agent, such as thionyl chloride, to afford a compound of formula III in which $L^1$ represents halo such as chloro. Compounds in which $L^1$ represents a hydroxyl group may be prepared, for example, by reacting a compound of formula Vb with an appropriate amino-substituted alcohol such as 2-aminoethanol or 3-aminopropan-1-ol.

In process (b), the term "reactive derivative" of compound IVa or Vb is intended to mean that the carboxylic acid is activated, for example, by forming an anhydride or carboxylic acid halide such as a carboxylic acid chloride. Alternatively, the carboxylic acid can be activated using conventional carboxylic acid/amine coupling reagents, such as carbodiimides, O-(7-azabenzotriazol-1-yl-N,N,N',N' tetramethyluronium hexafluorophosphate (HATU) and the like. This reaction is conveniently performed under conventional amide bond-forming conditions. The process is conveniently conducted at a temperature in the range of from −10 to 100° C.

Compounds of formula IVa can be prepared by reacting a compound of formula II with a compound of formula XV:

$L^3$-$CH_2(CH_2)_mCH_2COOP^2$      XV where $L^3$ represents a leaving group including, for example, a halo group such as chloro, bromo or iodo, or a sulfonic ester group such as mesylate or tosylate; and $P^2$ represents a hydrogen atom or a carboxyl-protecting group such as a (1-4C) alkyl group. If necessary, the carboxyl-protecting group $P^2$, is then removed, for example, by hydrolysis under conventional conditions such as by using lithium hydroxide.

Compounds of formula Va can be prepared by reacting a compound of formula IX with a compound of formula XVI:

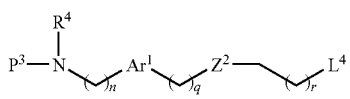

XVI where $P^3$ represents hydrogen or an amino-protecting group, such as tert-butoxycarbonyl, and $L^4$ represents a leaving group including, for example, a halo group such as chloro, bromo or iodo, or a sulfonic ester group such as mesylate or tosylate; followed if necessary, by removing an amino-protecting group $P^3$. Alternatively, such compounds can be prepared by reductive amination of a compound of formula XVII:

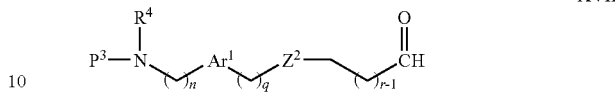

XVII using a compound of formula IX. The reducing agent may be, for example, hydrogen in the presence of a Group VIII metal catalyst such as palladium, or a metal hydride reducing agent such as a borohydride, including sodium triacetoxyborohydride. Convenient solvents include alcohols such as methanol. The reaction is conveniently performed at a temperature in the range of from 0 to 100° C.

Compounds of formula IVb can be prepared by reacting a compound of formula II with a compound of formula XVIII:

$C(O)H(CH_2)_mCH_2NR^4P^4$      XVIII where $P^4$ represents hydrogen or an amino-protecting group, such as benzyl, in the presence of a reducing agent, such as sodium triacetoxyborohydride, followed if necessary by removing the amino-protecting group $P^4$ by, for example, hydrogenation in the presence of palladium.

Compounds of formula Vb can be prepared by reacting a compound of formula IX with a compound of formula XIX:

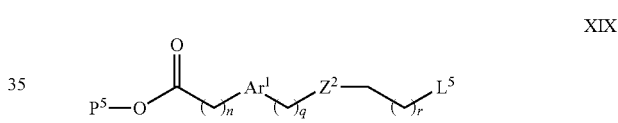

XIX where $P^5$ represents hydrogen or a carboxyl-protecting group such as methyl or ethyl, and $L^5$ represents a leaving group, followed if necessary by removing the carboxyl protecting group $P^5$. Alternatively, such compounds can be prepared by reductive amination of a compound of formula XX with a compound of formula IX:

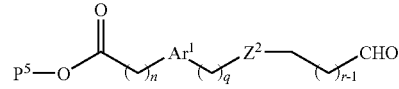

XX

The reducing agent may be, for example, hydrogen in the presence of a Group VIII metal catalyst such as palladium, or a metal hydride reducing agent such as a borohydride, including sodium triacetoxyborohydride. Convenient solvents include alcohols such as methanol. The reaction is conveniently performed at a temperature in the range of from 0 to 100° C.

Process (c) is conducted in a similar matter to that described in process (b), and the compounds of formula VIIa, VIIa, VIIb, and VII b are prepared in a similar manner as that described for the compounds of formula IVa, Va, Vb, Vb.

Referring to process (d), the leaving group represented by $L^2$ can be, for example, a halo group such as chloro, bromo or iodo, or a sulfonic ester group such as mesylate or tosylate. This reaction is conveniently performed in the presence of a base, for example, a tertiary amine such as diisopropylethylamine. Convenient solvents include nitriles such as acetonitrile. The reaction is conveniently conducted at a temperature in the range of from 0 to 100° C. The compounds of formula VIII can be prepared by reacting a compound of formula VIa with a compound of formula XXI:

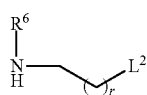

XXI or by reacting a compound of formula VIb with a compound of formula XXII:

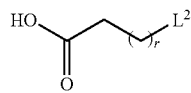

XXII

The reaction is conveniently performed following, for example, the method of process (b) described herein. Compounds of formula IX are generally known or can be prepared from readily available starting materials using well-known synthetic methods.

In process (e), the reducing agent may be, for example, hydrogen in the presence of a Group VIII metal catalyst such as palladium, or a metal hydride reducing agent such as a borohydride, including sodium triacetoxyborohydride, optionally used in combination with a titanium tetraalkoxide such as titanium tetraisopropoxide. Convenient solvents include alcohols such as methanol and halogenated hydrocarbons such as dichloromethane. The reaction is conveniently performed at a temperature in the range of from 0 to 100° C.

The compound of formula X may be prepared by oxidizing a compound corresponding to formula III in which $L^1$ represents a hydroxyl group. Such oxidation reactions can be conducted, for example, using sulfur dioxide pyridine complex in dimethylsulfoxide in the presence of a tertiary amine such as diisopropylethylamine.

In process (f), the reduction is preformed as described for process (e).

Compounds of formula XI may be prepared by reacting a compound of formula IVb with a compound of formula XXIII:

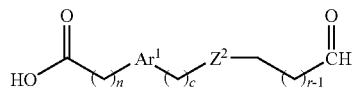

XXIII or a compound of formula VIb with a compound of formula XXIV:

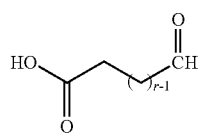

XXIV in the presence of a carboxylic acid/amine coupling agent such as 1-(3-dimethylaminopropyl)-3-ethylcarbodiimide (EDC) and 1-hydroxybenzotriazole hydrate (HOBT) and the like.

As will be apparent to those skilled in the art, compounds of the invention prepared by any of the aforementioned steps may be further derivatized to form other compounds of formula I using methods and reagents well-known in the art. By way of illustration, a compound of formula I may be reacted with bromine to afford a corresponding compound of formula I in which $R^2$, for example, represents a bromo group.

Further details regarding specific reaction conditions and other procedures for preparing representative compounds of the invention or intermediates thereof are described in the Examples set forth below.

Pharmaceutical Compositions and Formulations

The biphenyl compounds of the invention are typically administered to a patient in the form of a pharmaceutical composition or formulation. Such pharmaceutical compositions may be administered to the patient by any acceptable route of administration including, but not limited to, inhaled, oral, nasal, topical (including transdermal) and parenteral modes of administration.

It will be understood that any form of the compounds of the invention, (i.e., free base, pharmaceutically acceptable salt, solvate, etc.) that is suitable for the particular mode of administration can be used in the pharmaceutical compositions discussed herein.

Accordingly, one embodiment of the invention is directed to a pharmaceutical composition comprising a pharmaceutically acceptable carrier or excipient and a therapeutically effective amount of a compound of formula I, or a pharmaceutically acceptable salt or solvate or stereoisomer thereof. The pharmaceutical composition may contain other therapeutic and/or formulating agents if desired.

The pharmaceutical compositions of the invention typically contain a therapeutically effective amount of a compound of the invention or a pharmaceutically acceptable salt or solvate or stereoisomer thereof, as the active agent. Typically, such pharmaceutical compositions will contain from about 0.01 to 95% by weight of the active agent; including, from about 0.01 to 30%, such as from about 0.01 to 10%.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the ingredients for such compositions are commercially available from, for example, Sigma, P.O. Box 14508, St. Louis, Mo. 63178. By way of further illustration, conventional formulation techniques are described in *Remington: The Science and Practice of Pharmacy*, 20th Edition, Lippincott Williams & White, Baltimore, Md. (2000); and H. C. Ansel et al., *Pharmaceutical Dosage Forms and Drug Delivery Systems*, 7th Edition, Lippincott Williams & White, Baltimore, Md. (1999).

Representative examples of materials that can serve as pharmaceutically acceptable carriers include, but are not limited to, the following: sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; phosphate buffer solutions; compressed propellant gases such as chlorofluorocarbons and hydrofluorocarbons; and other non-toxic compatible substances employed in pharmaceutical compositions.

The pharmaceutical compositions of the invention are typically prepared by thoroughly and intimately mixing or blending a compound of the invention with a pharmaceutically acceptable carrier and one or more optional ingredients. If necessary or desired, the resulting uniformly blended mixture can then be shaped or loaded into tablets, capsules, pills, canisters, cartridges, dispensers and the like using conventional procedures and equipment.

In one embodiment, the pharmaceutical compositions of the invention are suitable for inhaled administration. Suitable pharmaceutical compositions for inhaled administration will typically be in the form of an aerosol or a powder. Such compositions are generally administered using well-known delivery devices such as a nebulizer inhaler, a metered-dose inhaler (MDI), a dry powder inhaler (DPI) or a similar delivery device.

In a specific embodiment of the invention, the pharmaceutical composition comprising the active agent is administered by inhalation using a nebulizer inhaler. Such nebulizer devices typically produce a stream of high velocity air that causes the pharmaceutical composition comprising the active agent to spray as a mist that is carried into the patient's respiratory tract. Accordingly, when formulated for use in a nebulizer inhaler, the active agent is typically dissolved in a suitable carrier to form a solution. Alternatively, the active agent can be micronized and combined with a suitable carrier to form a suspension of micronized particles of respirable size, where micronized is typically defined as having about 90% or more of the particles with a diameter of less than about 10 μm. Suitable nebulizer devices are commercially available, for example, by PARI GmbH (Starnberg, German). Other nebulizer devices include Respimat (Boehringer Ingelheim) and those described, for example, in U.S. Pat. No. 6,123,068 to Lloyd et al. and WO 97/12687 (Eicher et al.), the disclosures of which are incorporated herein by reference in their entirety.

A representative pharmaceutical composition for use in a nebulizer inhaler comprises an isotonic aqueous solution comprising from about 0.05 μg/mL to about 10 mg/mL of a compound of formula I or a pharmaceutically acceptable salt or solvate or stereoisomer thereof.

In another specific embodiment of the invention, the pharmaceutical composition comprising the active agent is administered by inhalation using a DPI. Such DPIs typically administer the active agent as a free-flowing powder that is dispersed in a patient's air-stream during inspiration. In order to achieve a free flowing powder, the active agent is typically formulated with a suitable excipient such as lactose or starch. Micronization is a common method of reducing crystal size to that suitable for pulmonary delivery. Typically, the active agent is micronized and combined with a suitable carrier to form a suspension of micronized particles of respirable size, where "micronized particles" or "micronized form" means at least about 90% of the particles have a diameter of less than about 10 μm. Other methods of reducing particle size may also be used such as fine milling, chopping, crushing, grinding, milling, screening, trituration, pulverization, and so forth, as long as the desired particle size can be obtained.

A representative pharmaceutical composition for use in a DPI comprises dry lactose having a particle size between about 1 μm and about 100 μm and micronized particles of a compound of formula I, or a pharmaceutically acceptable salt or solvate or stereoisomer thereof. Such a dry powder formulation can be made, for example, by combining the lactose with the active agent and then dry blending the components. Alternatively, if desired, the active agent can be formulated without an excipient. The pharmaceutical composition is then typically loaded into a dry powder dispenser, or into inhalation cartridges or capsules for use with a dry powder delivery device.

Examples of DPI delivery devices include Diskhaler (GlaxoSmithKline, Research Triangle Park, NC; see, e.g., U.S. Pat. No. 5,035,237 to Newell et al.); Diskus (GlaxoSmithKline; see, e.g., U.S. Pat. No. 6,378,519 to Davies et al.); Turbuhaler (AstraZeneca, Wilmington, Del.; see, e.g., U.S. Pat. No. 4,524,769 to Wetterlin); Rotahaler (GlaxoSmithKline; see, e.g., U.S. Pat. No. 4,353,365 to Hallworth et al.) and Handihaler (Boehringer Ingelheim). Further examples of suitable DPI devices are described in U.S. Pat. No. 5,415,162 to Casper et al., U.S, Pat, No. 5,239,993 to Evans, and U.S. Pat. No. 5,715,810 to Armstrong et al., and references cited therein. The disclosures of the aforementioned patents are incorporated herein by reference in their entirety.

In yet another specific embodiment of the invention, the pharmaceutical composition comprising the active agent is administered by inhalation using an MDI, which typically discharges a measured amount of the active agent or a pharmaceutically acceptable salt or solvate or stereoisomer thereof using compressed propellant gas. Accordingly, pharmaceutical compositions administered using an MDI typically comprise a solution or suspension of the active agent in a liquefied propellant. Any suitable liquefied propellant may be employed including chlorofluorocarbons such as $CCl_3F$, and hydrofluoroalkanes (HFAs) such as 1,1,1,2-tetrafluoroethane (HFA 134a) and 1,1,1,2,3,3,3-heptafluoro-n-propane, (HFA 227). Due to concerns about chlorofluorocarbons affecting the ozone layer, formulations containing HFAs are generally preferred. Additional optional components of HFA formulations include co-solvents such as ethanol or pentane, and surfactants such as sorbitan trioleate, oleic acid, lecithin, and glycerin. See, for example, U.S. Pat. No. 5,225,183 to Purewal et al., EP 0717987 A2 (Minnesota Mining and Manufacturing Company), and WO 92/22286 (Minnesota Mining and Manufacturing Company), the disclosures of which are incorporated herein by reference in their entirety.

A representative pharmaceutical composition for use in a metered-dose inhaler comprises from about 0.01 to 5% by weight of a compound of formula I, or a pharmaceutically acceptable salt or solvate or stereoisomer thereof; from about 0 to 20% by weight ethanol; and from about 0 to 5% by weight surfactant; with the remainder being an HFA propellant.

Such compositions are typically prepared by adding chilled or pressurized hydrofluoroalkane to a suitable container containing the active agent, ethanol (if present) and the surfactant (if present). To prepare a suspension, the active agent is micronized and then combined with the propellant. The formulation is then loaded into an aerosol canister, which forms a portion of a metered-dose inhaler device. Examples of metered-dose inhaler devices developed specifically for use with HFA propellants are described in U.S. Pat. No. 6,006,745 to Marecki and U.S. Pat. No. 6,143,277 to Ashurst et al. Alternatively, a suspension formulation can be prepared by spray drying a coating of surfactant on micronized particles of the active agent. See, for example, WO 99/53901 (Glaxo Group Ltd.) and WO 00/61108 (Glaxo Group Ltd.). The disclosures of the aforementioned patents and publications are incorporated herein by reference in their entirety.

For additional examples of processes of preparing respirable particles, and formulations and devices suitable for inhalation dosing see U.S. Pat. No. 6,268,533 to Gao et al., U.S. Pat. No. 5,983,956 to Trofast; U.S. Pat. No. 5,874,063 to Briggner et al.; and U.S. Pat. No. 6,221,398 to Jakupovic et al.; and WO 99/55319 (Glaxo Group Ltd.) and WO 00/30614 (AstraZeneca AB); the disclosures of which are incorporated herein by reference in their entirety.

In another embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the invention as an active ingredient. The pharmaceutical composition may be packaged in a unit dosage form.

When intended for oral administration in a solid dosage form (i.e., as capsules, tablets, pills and the like), the pharmaceutical compositions of the invention will typically comprise a compound of the present invention as the active ingredient and one or more pharmaceutically acceptable carriers such as sodium citrate or dicalcium phosphate. Optionally or alternatively, such solid dosage forms may also comprise: fillers or extenders such as starches, lactose, sucrose, glucose, mannitol, and/or silicic acid; binders such as carboxymethylcellulose, alginates, gelatin, polyvinyl pyrrolidone, sucrose and/or acacia; humectants such as glycerol; disintegrating agents such as agar-agar, calcium carbonate, potato or tapioca starch, alginic acid, certain silicates, and/or sodium carbonate; solution retarding agents such as paraffin; absorption accelerators such as quaternary ammonium compounds; wetting agents such as cetyl alcohol and/or glycerol monostearate; absorbents such as kaolin and/or bentonite clay; lubricants such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically acceptable antioxidants include: water-soluble antioxidants such as ascorbic acid, cysteine hydrochloride, sodium bisulfate, sodium metabisulfate sodium sulfite and the like; oil-soluble antioxidants such as ascorbyl palmitate, butylated hydroxyanisole (BHA), butylated hydroxytoluene (BHT), lecithin, propyl gallate, alpha-tocopherol, and the like; and metal-chelating agents such as citric acid, ethylenediamine tetraacetic acid (EDTA), sorbitol, tartaric acid, phosphoric acid, and the like. Coating agents for tablets, capsules, pills and like, include those used for enteric coatings such as cellulose acetate phthalate (CAP), polyvinyl acetate phthalate (PVAP), hydroxypropyl methylcellulose phthalate, methacrylic acid-methacrylic acid ester copolymers, cellulose acetate trimellitate (CAT), carboxymethyl ethyl cellulose (CMEC), hydroxypropyl methyl cellulose acetate succinate (HPMCAS), and the like.

If desired, the pharmaceutical compositions of the invention may also be formulated to provide slow or controlled release of the active ingredient using, by way of example, hydroxypropyl methyl cellulose in varying proportions; or other polymer matrices, liposomes and/or microspheres.

In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form, if appropriate, with one or more of the above-described excipients.

Suitable liquid dosage forms for oral administration include, by way of illustration, pharmaceutically acceptable emulsions, microemulsions, solutions, suspensions, syrups and elixirs. Such liquid dosage forms typically comprise the active ingredient and an inert diluent such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, oils (e.g., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminium metahydroxide, bentonite, agar-agar and tragacanth, and mixtures thereof.

The compounds of the invention can also be administered transdermally using known transdermal delivery systems and excipients. For example, a compound of the invention can be admixed with permeation enhancers such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The compounds of the invention can also be co-administered with other therapeutic agents. This combination therapy involves using a compound of the invention combined with one or more of these secondary agents, either formulated together (e.g., packaged together in a single formulation) or formulated separately (e.g., packaged as separate unit dosage forms). Methods of formulating multiple agents together in the same formulation or in separate unit dosage forms, are well known in the art.

The additional therapeutic agent(s) can be selected from other bronchodilators (e.g., $PDE_3$ inhibitors, adenosine 2b modulators and ($\beta_2$ adrenergic receptor agonists); anti-inflammatory agents (e.g., steroidal anti-inflammatory agents such as corticosteroids; non-steroidal anti-inflammatory agents (NSAIDs), and $PDE_4$ inhibitors); other muscarinic receptor antagonists (i.e., antichlolinergic agents); antiinfective agents (e.g., Gram positive and Gram negative antibiotics or antivirals); antihistamines; protease inhibitors; and afferent blockers (e.g., $D_2$ agonists and neurokinin modulators).

One particular embodiment of the invention is directed to a composition comprising (a) a pharmaceutically acceptable carrier and a therapeutically effective amount of a compound of formula I or a pharmaceutically acceptable salt or solvate or stereoisomer thereof; and (b) a pharmaceutically acceptable carrier and a therapeutically effective amount of an agent selected from a steroidal anti-inflammatory agent such as a corticosteroid; a $\beta_2$ adrenergic receptor agonist; a phosphodiesterase-4 inhibitor; or a combination thereof; wherein the compound of formula I and the agent are formulated together or separately. In another embodiment, (b) is a pharmaceutically acceptable carrier and a therapeutically effective amount of a $\beta_2$ adrenergic receptor agonist and a steroidal anti-inflammatory agent. The secondary agents can be used in the form of pharmaceutically acceptable salts or solvates, and if appropriate, as optically pure stereoisomers.

Representative $\beta_2$ adrenergic receptor agonists that can be used in combination with compounds of the invention include, but are not limited to, salmeterol, salbutamol, formoterol, salmefamol, fenoterol, terbutaline, albuterol, isoetharine, metaproterenol, bitolterol, pirbuterol, levalbuterol and the like, or pharmaceutically acceptable salts thereof. Other $\beta_2$ adrenergic receptor agonists that can be used include, but are not limited to, 3-(4-{[6-({(2R)-2-hydroxy-2-[4-hydroxy-3-(hydroxymethyl)-phenyl]ethyl}amino)-hexyl]oxy}butyl)benzenesulfonamide and 3-(−3-{[7-({(2R)-2-hydroxy-2-[4-hydroxy-3-(hydroxymethyl)phenyl]ethyl}-amino)heptyl]oxy}propyl)benzenesulfonamide and related compounds described in WO 02/066422 (Glaxo Group Ltd.); 3-[3-(4-{[6-(2R)-2-hydroxy-2-[4-hydroxy-3-(hydroxymethyl)phenyl]ethyl}amino)hexyl]oxy}butyl)-phenyl]imidazolidine-2,4-dione and related compounds described in WO 02/070490 (Glaxo Group Ltd.); 3-(4-{[6-({(2R)-2-[3-(formylamino)-4-hydroxyphenyl]-2-hydroxyethyl}amino) hexyl]oxy}butyl)-benzenesulfonamide, 3-(4-{[6-({(2S)-2-[3-(formylamino)-4-hydroxyphenyl]-2-hydroxyethyl}amino)hexyl]oxy}butyl)-benzenesulfonamide, 3-(4-{[6-({(2R/S)-2-[3-(formylamino)-4-hydroxyphenyl]-2-hydroxyethyl}amino) hexyl]oxy}butyl)-benzenesulfonamide, N-(tert-butyl)-3-(4-{[6-({(2R)-2-[3-(formylamino)-4-hydroxyphenyl]-2-hydroxyethyl}amino)hexyl]-oxy} butyl) benzenesulfonamide, N-(tert-butyl)-3-(4-{[6-({(2S)-2-[3-(formylamino)-4-hydroxyphenyl]-2-hydroxyethyl}amino)-hexyl]oxy}butyl)-benzenesulfonamide, N-(tert-butyl)-3-(4-{[6-({(2R/S)-2-[3-(formylamino)-4-hydroxyphenyl]-2-hydroxyethyl}amino) hexyl]-oxy}butyl) benzenesulfonamide and related compounds described in WO 02/076933 (Glaxo Group Ltd.); 4-{(1R)-2-[(6-{2-[(2,6-dichlorobenzyl)oxy]ethoxy} hexyl)amino]-1-hydroxyethyl}-2-(hydroxymethyl)phenol and related compounds described in WO 03/024439 (Glaxo Group Ltd.); N-{2-[4-((R)-2-hydroxy-2-phenylethylamino)phenyl]ethyl}-(R)-2-hydroxy-2-(3-formamido-4-hydroxyphenyl)ethylamine and related compounds described in U.S. Pat. No. 6,576,793 to Moran et al.; N-{2-[4-(3-phenyl-4-methoxyphenyl)amino phenyl]ethyl}-(R)-2-hydroxy-2-(8-hydroxy-2(1H)-quinolinon-5-yl)ethylamine and related compounds described in U.S. Pat. No. 6,653,323 to Moran et al.; and pharmaceutically acceptable salts thereof. In a particular embodiment, the $\beta_2$-adrenoreceptor agonist is a crystalline monohydrochloride salt of N-{2-[4-((R)-2-hydroxy-2-phenylethylamino) phenyl]ethyl}-(R)-2-hydroxy-2-(3-formamido-4-hydroxyphenyl)ethylamine. When employed, the $\beta_2$-adrenoreceptor agonist will be present in the pharmaceutical composition in a therapeutically effective amount. Typically, the $\beta_2$-adrenoreceptor agonist will be present in an amount sufficient to provide from about 0.05 µg to 500 µg per dose. The disclosures of the aforementioned patents and publications are incorporated herein by reference in their entirety.

Representative steroidal anti-inflammatory agents that can be used in combination with compounds of the invention include, but are not limited to, methyl prednisolone, prednisolone, dexamethasone, fluticasone propionate, 6α,9α-difluoro-17α-[(2-furanylcarbonyl)oxy]-11β-hydroxy-16α-methyl-3-oxoandrosta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydrofuran-3S-yl) ester, beclomethasone esters (e.g., the 17-propionate ester or the 17,21-dipropionate ester), budesonide, flunisolide, mometasone esters (e.g., the furoate ester), triamcinolone acetonide, rofleponide, ciclesonide, butixocort propionate, RPR-106541, ST-126 and the like, or pharmaceutically-acceptable salts thereof. When employed, the steroidal anti-inflammatory agent will be present in the composition in a therapeutically effective amount. Typically, the steroidal anti-inflammatory agent will be present in an amount sufficient to provide from about 0.05 µg to 500 µg per dose.

An exemplary combination is a compound of formula I, or pharmaceutically acceptable salt or solvate or stereoisomer thereof, co-administered with salmeterol as the $\beta_2$ adrenergic receptor agonist, and fluticasone propionate as the steroidal anti-inflammatory agent. Another exemplary combination is a compound of formula I, or pharmaceutically acceptable salt or solvate or stereoisomer thereof, co-administered with a crystalline monohydrochloride salt of N-{2-[4-((R)-2-hydroxy-2-phenylethylamino)phenyl]ethyl}-(R)-2-hydroxy-2-(3-formamido-4-hydroxyphenyl)ethylamine as the $\beta_2$-adrenoreceptor agonist, and 6α,9α-difluoro-17α-[(2-furanylcarbonyl)oxy]-11β-hydroxy-16α-methyl-3-oxoandrosta-1,4-diene-17β-carbothioic acid S-fluoromethyl ester as the steroidal anti-inflammatory agent. As noted above, these agents can be formulated together or separately.

Other suitable combinations include, for example, other anti-inflammatory agents, e.g., NSAIDs (e.g., sodium cromoglycate, nedocromil sodium, and phosphodiesterase (PDE) inhibitors such as theophylline, PDE4 inhibitors and mixed PDE3/PDE4 inhibitors); leukotriene antagonists (e.g., monteleukast); inhibitors of leukotriene synthesis; iNOS inhibitors; protease inhibitors such as tryptase and elastase inhibitors; beta-2 integrin antagonists and adenosine receptor agonists or antagonists (e.g., adenosine 2a agonists); cytokine antagonists (e.g., chemokine antagonists such as, an interleukin antibody (αIL antibody), specifically, an αIL-4 therapy, an αIL-13 therapy, or a combination thereof); or inhibitors of cytokine synthesis.

Representative phosphodiesterase-4 (PDE4) inhibitors or mixed PDE3/PDE4 inhibitors that can be used in combination with the compounds of the invention include, but are not limited to cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl) cyclohexan-1-one; cis-[4-cyano-4-(3-cyclopropylmethoxy-4-difluoromethoxyphenyl)cyclohexan-1-ol]; cis-4-cyano-4-[3-(cyclopentyloxy)-4-methoxyphenyl]cyclohexane-1-carboxylic acid and the like, or pharmaceutically acceptable salts thereof. Other representative PDE4 or mixed PDE4/PDE3 inhibitors include AWD-12-281 (elbion); NCS-613 (INSERM); D-4418 (Chiroscience and Schering-Plough); CI-1018 or PD-168787 (Pfizer); benzodioxole compounds described in WO99/16766 (Kyowa Hakko); K-34 (Kyowa Hakko); V-11294A (Napp); roflumilast (Byk-Gulden); pthalazinone compounds described in WO99/47505 (Byk-Gulden); Pumafentrine (Byk-Gulden, now Altana); arofylline (Almirall-Prodesfarma); VM554/UM565 (Vernalis); T-440 (Tanabe Seiyaku); and T2585 (Tanabe Seiyaku).

Representative muscarinic antagonists (i.e., anticholinergic agents) that can be used in combination with the compounds of the invention include, but are not limited to, atropine, atropine sulfate, atropine oxide, methylatropine nitrate, homatropine hydrobromide, hyoscyamine (d,l) hydrobromide, scopolamine hydrobromide, ipratropium bromide, oxitropium bromide, tiotropium bromide, methantheline, propantheline bromide, anisotropine methyl bromide, clidinium bromide, copyrrolate (Robinul), isopropamide iodide, mepenzolate bromide, tridihexethyl chloride (Pathilone), hexocyclium methylsulfate, cyclopentolate hydrochloride, tropicamide, trihexyphenidyl hydrochloride, pirenzepine, telenzepine, AF-DX 116 and methoctramine and the like, or a pharmaceutically acceptable salt thereof; or, for those compounds listed as a salt, alternate pharmaceutically acceptable salt thereof.

Representative antihistamines (i.e., $H_1$-receptor antagonists) that can be used in combination with the compounds of the invention include, but are not limited to, ethanolamines such as carbinoxamine maleate, clemastine fumarate, diphenylhydramine hydrochloride and dimenhydrinate; ethylenediamines such as pyrilamine amleate, tripelennamine hydrochloride and tripelennamine citrate; alkylamines such as chlorpheniramine and acrivastine; piperazines such as hydroxyzine hydrochloride, hydroxyzine pamoate, cyclizine hydrochloride, cyclizine lactate, meclizine hydrochloride and cetirizine hydrochloride; piperidines such as astemizole, levocabastine hydrochloride, loratadine or its descarboethoxy analogue, terfenadine and fexofenadine hydrochloride; azelastine hydrochloride; and the like, or a pharmaceutically acceptable salt thereof; or, for those compounds listed as a salt, alternate pharmaceutically acceptable salt thereof.

Unless otherwise indicated, exemplary suitable doses for the other therapeutic agents administered in combination with a compound of the invention are in the range of about 0.05 μg/day to 100 mg/day.

The following formulations illustrate representative pharmaceutical compositions of the invention, as well as exemplary methods of preparation. One or more secondary agents can optionally be formulated with the compound of the invention (primary active agent). Alternately, the secondary agents(s) can be formulated separately and co-administered with the primary active agent, either simultaneously or sequentially. For example, in one embodiment, a single dry powder formulation can be manufactured to include both the compound of the invention and one or more secondary agents. In another embodiment, one formulation is manufactured to contain the compound of the invention and separate formulation(s) are manufactured to contain the secondary agent(s). Such dry powder formulations can then be packaged in separate blister packs and administered with a single DPI device.

Exemplary Dry Powder Formulation For Administration By Inhalation 0.2 mg of a compound of the invention is micronized and then blended with 25 mg of lactose. The blended mixture is then loaded into a gelatin inhalation cartridge. The contents of the cartridge are administered using a powder inhaler.

Exemplary Dry Powder Formulation for Administration by a Dry Powder Inhaler

A dry powder is prepared having a bulk formulation ratio of micronized compound of the invention (active agent) to lactose of 1:200. The powder is packed into a dry powder inhalation device capable of delivering between about 10 μg and 100 μg of active agent per dose.

Exemplary Formulations for Administration by a Metered Dose Inhaler

A suspension containing 5 wt % of a compound of the invention (active agent) and 0.1 wt % lecithin is prepared by dispersing 10 g of the active agent as micronized particles with a mean size less than 10 μm in a solution formed from 0.2 g of lecithin dissolved in 200 ml, of demineralized water. The suspension is spray dried and the resulting material is micronized to particles having a mean diameter less than 1.5 μm. The particles are loaded into cartridges with pressurized 1,1,1,2-tetrafluoroethane.

Alternately, a suspension containing 5 wt % of the active agent, 0.5 wt % lecithin, and 0.5 wt % trehalose is prepared by dispersing 5 g of the active agent as micronized particles with a mean size less than 10 μm in a colloidal solution formed from 0.5 g of trehalose and 0.5 g of lecithin dissolved in 100 mL of demineralized water. The suspension is spray dried and the resulting material is micronized to particles having a mean diameter less than 1.5 μm. The particles are loaded into canisters with pressurized 1,1,1,2-tetrafluoroethane.

Exemplary Aqueous Aerosol Formulation for Administration by Nebulizer

A pharmaceutical composition is prepared by dissolving 0.5 mg of a compound of the invention (active agent) in 1 mL of a 0.9% sodium chloride solution acidified with citric acid. The mixture is stirred and sonicated until the active agent is dissolved. The pH of the solution is adjusted to a value in the range of from 3 to 8 (typically about 5) by the slow addition of NaOH.

Exemplary Hard Gelatin Capsule Formulation for Oral Administration

The following ingredients are thoroughly blended and then loaded into a hard gelatin capsule: 250 mg of a compound of the invention, 200 mg of lactose (spray-dried), and 10 mg of magnesium stearate, for a total of 460 mg of composition per capsule.

Exemplary Suspension Formulation for Oral Administration

The following ingredients are mixed to form a suspension containing 100 mg of active ingredient per 10 mL of suspension.

| Ingredients | Amount |
| --- | --- |
| Compound of the invention | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Exemplary Injectable Formulation

The following ingredients are blended and the pH is adjusted to 4±0.5 using 0.5 N HCl or 0.5 N NaOH.

| Ingredients | Amount |
| --- | --- |
| Compound of the invention | 0.2 g |
| Sodium acetate buffer solution (0.4 M) | 2.0 mL |
| HCl (0.5 N) or NaOH (0.5 N) | q.s. to pH 4 |
| Water (distilled, sterile) | q.s. to 20 mL |

Utility

The biphenyl compounds of the invention are expected to be useful as muscarinic receptor antagonists and therefore, such compounds are expected to be useful for treating medical conditions mediated by muscarinic receptors, i.e., medical conditions which are ameliorated by treatment with a muscarinic receptor antagonist. Such medical conditions include, by way of example, pulmonary disorders or diseases including those associated with reversible airway obstruction such as chronic obstructive pulmonary disease (e.g., chronic and wheezy bronchitis and emphysema), asthma, pulmonary fibrosis, allergic rhinitis, rhinorrhea, and the like. Other medical conditions that can be treated with muscarinic receptor antagonists are genitourinary tract disorders such as overactive bladder or detrusor hyperactivity and their symptoms; gastrointestinal tract disorders such as irritable bowel syndrome, diverticular disease, achalasia, gastrointestinal hypermotility disorders and diarrhea; cardiac arrhythmias such as sinus bradycardia; Parkinson's disease; cognitive disorders such as Alzheimer's disease; dismenorrhea; and the like.

In one embodiment, compounds of the invention are useful for treating smooth muscle disorders in mammals, including humans and their companion animals (e.g., dogs, cats etc.). Such smooth muscle disorders include, by way of illustration, overactive bladder, chronic obstructive pulmonary disease and irritable bowel syndrome.

When used to treat smooth muscle disorders or other conditions mediated by muscarinic receptors, compounds of the invention will typically be administered orally, rectally, parenterally or by inhalation in a single daily dose or in multiple doses per day. The amount of active agent administered per dose or the total amount administered per day will typically be determined by the patient's physician and will depend on such factors as the nature and severity of the patients condition, the condition being treated, the age and general health of the patient, the tolerance of the patient to the active agent, the route of administration and the like.

Typically, suitable doses for treating smooth muscle disorders or other disorders mediated by muscarinic receptors will range from about 0.14 µg/kg/day to 7 mg/kg/day of active agent; including from about 0.15 µg/kg/day to 5 mg/kg/day. For an average 70 kg human, this would amount to about 10 µg to 500 mg per day of active agent.

In a specific embodiment, the compounds of the invention are useful for treating pulmonary or respiratory disorders, such as COPD or asthma, in mammals including humans. When used to treat such disorders, the compounds of the invention will typically be administered by inhalation in multiple doses per day, in a single daily dose or a single weekly dose. Generally, the dose for treating a pulmonary disorder will range from about 10 µg/day to 200 µg/day. As used herein, COPD includes chronic obstructive bronchitis and emphysema (see, for example, Barnes, Chronic Obstructive Pulmonary Disease, *N Engl J Med* 343:269-78 (2000)).

When used to treat a pulmonary disorder, compounds of the invention are optionally administered in combination with other therapeutic agents such as a $\beta_2$-adrenoreceptor agonist; a corticosteroid, a non-steroidal anti-inflammatory agent, or combinations thereof.

When administered by inhalation, compounds of the invention typically have the effect of producing bronchodilation. Accordingly, one embodiment of the invention is directed to a method of producing bronchodilation in a patient, comprising administering to a patient a bronchodilation-producing amount of a compound of the invention. Generally, the therapeutically effective dose for producing bronchodilation will range from about 10 µg/day to 200 µg/day.

In another embodiment, compounds of the invention are used to treat overactive bladder. When used to treat overactive bladder, the compounds of the invention will typically be administered orally in a single daily dose or in multiple doses per day; preferably in a single daily dose. In one embodiment, the dose for treating overactive bladder will range from about 1.0 to 500 mg/day.

In yet another embodiment, compounds of the invention are used to treat irritable bowel syndrome. When used to treat irritable bowel syndrome, the compounds of the invention will typically be administered orally or rectally in a single daily dose or in multiple doses per day. In one embodiment, the dose for treating irritable bowel syndrome will range from about 1.0 to 500 mg/day.

Since compounds of the invention are muscarinic receptor antagonists, such compounds are also useful as research tools for investigating or studying biological systems or samples having muscarinic receptors. Such biological systems or samples may comprise $M_1$, $M_2$, $M_3$, $M_4$ and/or $M_5$ muscarinic receptors. Any suitable biological system or sample having muscarinic receptors may be employed in such studies, which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.), and the like.

In this embodiment, a biological system or sample comprising a muscarinic receptor is contacted with a muscarinic receptor-antagonizing amount of a compound of the invention. The effects of antagonizing the muscarinic receptor are then determined using conventional procedures and equipment such as radioligand binding assays and functional assays. Such functional assays include ligand-mediated changes in intracellular cyclic adenosine monophosphate (cAMP), ligand-mediated changes in activity of the enzyme adenylyl cyclase (which synthesizes cAMP), ligand-mediated changes in incorporation of guanosine 5'-O-(γ-thio) triphosphate ([$^{35}$S]GTPγS) into isolated membranes via receptor catalyzed exchange of [$^{35}$S]GTPγS for guanosine 5'-diphosphate (GDP), ligand-mediated changes in free intracellular calcium ions (measured, for example, with a fluorescence-linked imaging plate reader or FLIPR® from Molecular Devices, Inc.). Compounds of the invention will antagonize or decrease the activation of muscarinic receptors in any of the functional assays listed above, or assays of a similar nature. A muscarinic receptor-antagonizing amount of a compound of the invention will typically range from about 0.1 to 100 nanomolar.

Additionally, compounds of the invention can be used as research tools for discovering new compounds that have muscarinic receptor antagonist activity. In this embodiment, muscarinic receptor binding data (e.g., as determined by in vitro radioligand displacement assays) for a test compound or a group of test compounds is compared to the muscarinic receptor binding data for a compound of the invention to identify those test compounds that have about equal or superior muscarinic receptor binding, if any. This aspect of the invention includes, as separate embodiments, both the generation of comparison data (using the appropriate assays) and the analysis of the test data to identify test compounds of interest.

In another embodiment, compounds of the invention are used to antagonize a muscarinic receptor in a biological system, and a mammal in particular such as mice, rats, guinea pigs, rabbits, dogs, pigs, humans and so forth. In this embodiment, a therapeutically effective amount of a compound of formula I is administered to the mammal. The effects of antagonizing the muscarinic receptor can then determined using conventional procedures and equipment, examples of which are described above.

Among other properties, compounds of the invention have been found to be potent inhibitors of $M_3$ muscarinic receptor activity. Accordingly, in a specific embodiment, the invention is directed to compounds of formula I having an inhibition dissociation constant ($K_i$) for the $M_3$ receptor subtype of less than or equal to 10 nM, as determined, for example, by an in vitro radioligand displacement assay. In one embodiment, compounds of the invention have a Ic value for the $M_3$ receptor subtype of less than or equal to 5 nM.

Additionally, compounds of the invention are expected to possess a desirable duration of action. Accordingly, in another specific embodiment, the invention is directed to compounds of formula I having a duration of action greater than or equal to about 24 hours. Moreover, compounds of the invention are also expected to possess reduced side effects, such as dry mouth, at efficacious doses when administered by inhalation compared to other known muscarinic receptor antagonists administered by inhalation (such as tiotropium).

These and other properties, as well as the utility of the compounds, can be demonstrated using various in vitro and in vivo assays that are well-known to those skilled in the art. For example, representative assays are described in further detail in the following Examples.

EXAMPLES

The Preparations and Examples illustrate specific embodiments of the invention. The following abbreviations have the following meanings unless otherwise indicated and any other abbreviations used herein and not defined have their standard meaning:

AC adenylyl cyclase
ACh acetylcholine
ACN acetonitrile
BSA bovine serum albumin
cAMP 3'-5' cyclic adenosine monophosphate
CHO Chinese hamster ovary
$cM_5$ cloned chimpanzee $M_5$ receptor
DCM dichloromethane (i.e., methylene chloride)
DIPEA N,N-diisopropylethylamine
DMF N,N-dimethylformamide
DMSO dimethyl sulfoxide
dPBS Dulbecco's phosphate buffered saline
EDCI 1-(3-dimethylaminopropyl)-3-ethylcarbodiimide hydrochloride
EDTA ethylenediaminetetraacetic acid
EtOAc ethyl acetate
EtOH ethanol
FBS fetal bovine serum
FLIPR fluorometric imaging plate reader
HATU O-(7-azabenzotriazol-1-yl-N,N,N',N'-tetramethyluronium hexafluorophosphate
HBSS Hank's buffered salt solution
HEPES 4-(2-hydroxyethyl)-1-piperazineethanesulfonic acid
$hM_1$ cloned human $M_1$ receptor
$hM_2$ cloned human $M_2$ receptor
$hM_3$ cloned human $M_3$ receptor
$hM_4$ cloned human $M_4$ receptor
$hM_5$ cloned human $M_5$ receptor
HOAc acetic acid
HOBT 1-hydroxybenzotriazole hydrate
HPLC high-performance liquid chromatography
IPA isopropanol
LCMS liquid chromatography mass spectrometry
MCh methylcholine
MeOH methanol
MTBE methyl t-butyl ether
$Na(OAc)_3BH$ sodium triacetoxyborohydride
TFA trifluoroacetic acid
THF tetrahydrofuran Any other abbreviations used herein but not defined have their standard, generally accepted meaning. Unless noted otherwise, all materials, such as reagents, starting materials and solvents, were purchased from commercial suppliers (such as Sigma-Aldrich, Fluka, and the like) and were used without further purification.

Unless otherwise indicated, HPLC analysis was conducted using an Agilent (Palo Alto, Calif.) Series 1100 instrument equipped with Zorbax Bonus RP 2.1×50 mm columns (Agilent) having a 3.5 micron particle size. Detection was by UV absorbance at 214 nm. The mobile phases employed were as follows (by volume): A is ACN (2%), water (98%) and TFA (0.1%); and B is ACN (90%), water (10%) and TFA (0.1%). HPLC 10-70 data was obtained using a flow rate of 0.5 mL/minute of 10 to 70% B over a 6 minute gradient (with the remainder being A). Similarly, HPLC 5-35 data and HPLC 10-90 data were obtained using 5 to 35% B; or 10 to 90% B over a 5 minute gradient.

LCMS data were obtained with an Applied Biosystems (Foster City, Calif.) Model API-150EX instrument. LCMS 10-90 data was obtained using 10 to 90% Mobile Phase B over a 5 minute gradient.

Small-scale purification was conducted using an API-150EX Prep Workstation system from Applied Biosystems. The mobile phases employed were as follows (by volume): A is water and 0.05% TFA; and B is ACN and 0.05% TFA. For arrays (typically about 3 to 50 mg recovered sample size) the following conditions were used: 20 mL/min flow rate; 15 minute gradients and a 20 mm×50 mm Prism RP column with 5 micron particles (Thermo Hypersil-Keystone, Bellefonte, Pa.). For larger scale purifications (typically greater than 100 mg crude sample), the following conditions were used: 60 mL/min flow rate; 30 minute gradients and a 41.4 mm×250 mm Microsorb BDS column with 10 micron particles (Varian, Palo Alto, Calif.).

Preparation 1

N-(2-tert-Butoxycarbonylaminoethyl)isophthalamic Acid Methyl Ester

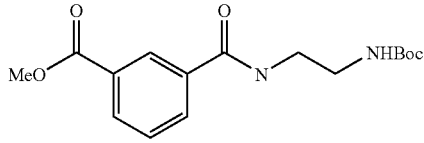

Mono-methyl isophthalate (10.0 g, 55.5 mmol), t-butyl n-(2-aminoethyl) carbamate (8.89 g, 55.5 mmol, 1.0 eq) and EDCI (12.2 g, 63.8 mmol, 1.15 eq) were dissolved in 270 mL DCM, followed by the addition of DIPEA (29.0 mL, 166 mmol, 3.0 eq). The reaction was allowed to stir at room temperature overnight. It was then taken up in 100 mL of DCM, washed with a 1:1 solution of 1.0 N HCl in brine, water, and a 1:1 solution of brine in saturated $NaHCO_3$. The organic layer was dried over $Na_2SO_4$, filtered and concentrated to afford the product as a light yellow solid (12.81 g, 72%).

Preparation 2

N-(2-tert-Butoxycarbonylaminoethyl)isophthalamic Acid

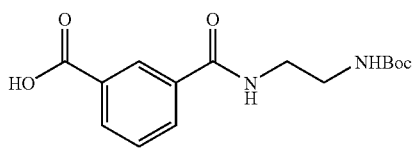

38.8 g of N-(2-tert-butoxycarbonylaminoethyl)isophthalamic acid methyl ester (prepared as described in Preparation 1) was dissolved in a solution of THF/DMF (1:1, 740 mL), and NaOH (111 mL of 10 N solution, 1.11 mol, 10.0 eq) was added. The reaction was stirred at room temperature overnight. The pH was then adjusted to pH 9 using 1.0 N HCl and concentrated to ~250 mL volume under vacuum. The mixture was filtered to remove impurities. The filtrate was further acidified to pH 5 by slow addition of 1.0 N HCl, and concentrated to ~200 mL volume. The precipitate was collected by filtration, rinsed with water and EtOAc, and dried under vacuum to give the product as a white solid (17.75 g, 52%).

For large scale synthesis, the reaction was carried out in MTBE using 2N NaOH (3 eq). The title compound was further purified via crystallization in MeOH.

Preparation 3

Biphenyl-2-ylcarbamic Acid Piperidin-4-yl Ester

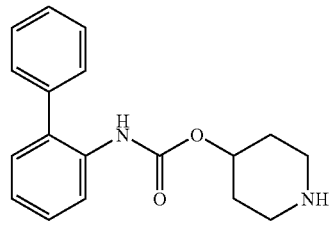

Biphenyl-2-isocyanate (97.5 g, 521 mmol) and 4-hydroxy-N-benzylpiperidine (105 g, 549 mmol) were heated together at 70° C. for 12 hours. The reaction mixture was then cooled to 50° C., EtOH (1 L) was added and then 6M HCl (191 mL) was added slowly. The resulting mixture was then cooled to ambient temperature, ammonium formate (98.5 g, 1.56 mol) was added, and then nitrogen gas was bubbled through the solution vigorously for 20 minutes. Palladium on activated carbon (20 g, 10 wt % dry basis) was added and the reaction mixture was heated at 40° C. for 12 hours, and then filtered through a pad of Celite. The solvent was then removed under reduced pressure and 1M HCl (40 mL) was added to the crude residue. The pH of the mixture was then adjusted with 10 N NaOH to pH 12. The aqueous layer was extracted with EtOAc (2×150 mL) and the organic layer was dried (magnesium sulfate), filtered and the solvent removed under reduced pressure to give 155 g of the title intermediate (100% yield). HPLC (10-70) $R_t$=2.52; m/z: [M+H$^+$] calcd for $C_{18}H_{20}N_2O_2$, 297.15; found, 297.3.

Preparation 4

N-Benzyl-N-methylaminoacetaldehyde

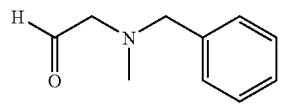

To a 3-necked 2-L flask was added N-benzyl-N-methylethanolamine (30.5 g, 0.182 mol), DCM (0.5 L), DIPEA (95 mL, 0.546 mol) and DMSO (41 mL, 0.728 mol). Using an ice bath, the mixture was cooled to about −10° C. and sulfur trioxide pyridine-complex (87 g, 0.546 mol) was added in 4 portions over 5 minute intervals. The reaction was stirred at −10° C. for 2 hours. Before removing the ice-bath, the reaction was quenched by adding water (0.5 L). The aqueous layer was separated and the organic layer was washed with water (0.5 L) and brine (0.5 L) and then dried over magnesium sulfate and filtered to provide the title compound which was used without further purification.

Preparation 5

Biphenyl-2-ylcarbamic Acid 1-[2-(Benzylmethylamino)ethyl]piperidin-4-yl Ester

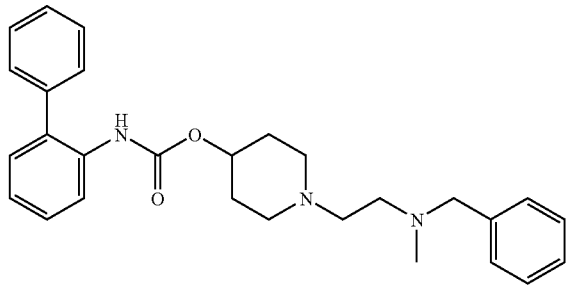

To a 2-L flask, containing N-benzyl-N-methylaminoacetaldehyde in DCM (0.5 L; prepared as described in Preparation 4) was added biphenyl-2-ylcarbamic acid piperidin-4-yl ester (30 g, 0.101 mol; prepared as described in Preparation 3) followed by Na(OAc)$_3$BH (45 g, 0.202 mol). The reaction mixture was stirred overnight and then quenched by the addition of 1 N HCl (0.5 L) with vigorous stirring. Three layers were observed and the aqueous layer was removed. After washing with 1N NaOH (0.5 L), a homogenous organic layer was obtained which was then washed with a saturated solution of aqueous NaCl (0.5 L), dried over magnesium sulfate, filtered and the solvent removed under reduced pressure. The residue was purified by dissolving it in a minimal amount of isopropanol and cooling this solution to 0° C. to form a solid which was collected and washed with cool isopropanol to provide 42.6 g of the title compound (95% yield). MS m/z: [M+H$^+$] calcd for $C_{28}H_{33}N_3O_2$, 444.3; found, 444.6. $R_f$=3.51 min (10-70 ACN:H$_2$O, reverse phase HPLC).

Preparation 5A

Alternately, the title compound was prepared by mesylation of N-benzyl-N-methyl ethanolamine, which was then reacted with biphenyl-2-ylcarbamic acid piperidin-4-yl ester in an alkylation reaction.

A 500 mL flask (reactor flask) was charged with N-benzyl-N-methylethanolamine (24.5 mL), DCM (120 mL), NaOH (80 mL; 30 wt %) and tetrabutylammonium chloride. Mixing at low speed throughout the reaction, the mixture was cooled to –10° C. (cooling bath), and the addition funnel charged with DCM (30 mL) and mesyl chloride (15.85 mL), which was added drop wise at a constant rate over 30 minutes. The addition was exothermic, and stirring was continued for 15 minutes while the temperature equilibrated back to –10° C. The reaction was held for at least 10 minutes to ensure full hydrolysis of the excess mesyl chloride.

A 250 mL flask was charged with biphenyl-2-ylcarbamic acid piperidin-4-yl ester (26 g; prepared as described in Preparation 3) and DCM (125 mL), stirred for 15 minutes at room temperature, and the mixture chilled briefly to 10° C. to form a slurry. The slurry was then charged into the reactor flask via the addition funnel. The cooling bath was removed and the reaction mixture was warmed to 5° C. The mixture was transferred to a separatory funnel, the layers allowed to settle, and the aqueous layer removed. The organic layer was transferred back to the reactor flask, stirring resumed, the mixture held to room temperature, and the reaction monitored by HPLC for a total of 3.5 hours.

The reactor flask was charged with NaOH (1M solution; 100 mL), stirred, and the layers allowed to settle. The organic layer was separated, washed (NaCl satd. solution), its volume partially reduced under vacuum, and subjected to repeated IPA washings. The solids were collected and allowed to air-dry (25.85 g, 98% purity). Additional solids were obtained from further processing of the mother liquor (volume reduction, IPA, cooling).

Preparation 6

Biphenyl-2-ylcarbamic Acid 1-(2-Methylaminoethyl)piperidin-4-yl Ester

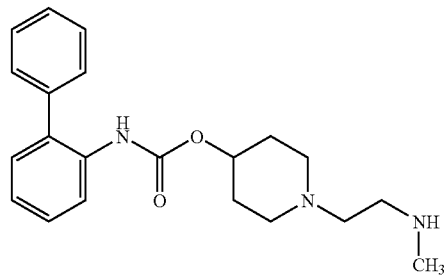

To a Parr hydrogenation flask was added biphenyl-2-ylcarbamic acid 1-[2-(benzylmethylamino)ethyl]piperidin-4-yl ester (40 g, 0.09 mol; prepared as described in Preparation 5) and EtOH (0.5 L). The flask was flushed with nitrogen gas and palladium on activated carbon (15 g, 10 wt % dry basis, 37% wt/wt) was added along with HOAc (20 mL). The mixture was kept on the Parr hydrogenator under a hydrogen atmosphere (~50 psi) for 3 hours. The mixture was then filtered and washed with EtOH. The filtrate was condensed and the residue was dissolved in a minimal amount of DCM. Isopropyl acetate (10 volumes) was added slowly to form a solid which was collected to provide 22.0 g of the title compound (70% yield). MS m/z: [M+H$^+$] calcd for $C_{21}H_{27}N_3O_2$, 354.2; found, 354.3. $R_f$=2.96 min (10-70 ACN:H$_2$O, reverse phase HPLC).

Preparation 7

Biphenyl-2-ylcarbamic acid 1-(2-{-[3-(2-tert-butoxy-carbonylaminoethylcarbamoyl)benzoyl]methylamino}ethyl)piperidin-4-yl ester

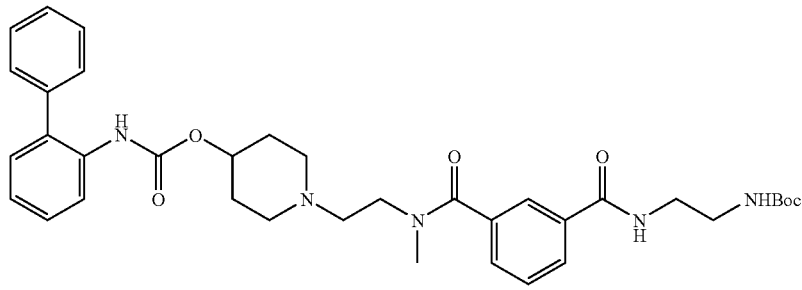

To a solution of N-(2-tert-butoxycarbonylaminoethyl) isophthalamic acid (9.35 g, 30.3 mmol; prepared as described in Preparation 2) and biphenyl-2-ylcarbamic acid 1-(2-methylaminoethyl)piperidin-4-yl ester (9.64 g, 27.3 mmol, 0.9 eq; prepared as described in Preparation 6) in 150 mL of DCM was added EDCI (6.98 g, 36.4 mmol, 1.2 eq) followed by 15.8 mL of DIPEA (91.0 mmol, 3.0 eq). At this point, HPLC analysis was conducted to ascertain the extent of reaction. Following overnight stirring, the reaction was concentrated under vacuum and taken up in 200 mL DCM. The mixture was then washed twice with 150 mL aqueous saturated NaHCO$_3$, once with 150 mL brine and 5 times with 200 ml, of a 1:1 solution of 1.0 N HCl in brine to remove any residual ester. The organic phase was then dried over Na$_2$SO$_4$, filtered and concentrated. 20.15 g of crude product was obtained as a white foam solid and used in the next step without further purification.

For large scale synthesis, the reaction was carried out in DCM in the presence of EDCI (1.2 eq), HOBT (1.2 eq) and DIPEA (3 eq) for 16 hours at room temperature and 5 hours at reflux.

Preparation 7A

Alternately, the title compound was prepared by acylation of 3-acetylbenzoic acid with biphenyl-2-ylcarbamic acid 1-(2-methylaminoethyl)piperidin-4-yl ester, which then underwent oxidation, followed by an N-acylation step.

3-carboxybenzaldehyde (4.07 g, 27.11 mmol, 1 eq), HATU (10.307 g, 27.11 mmol, 1 eq) and biphenyl-2-ylcarbamic acid 1-(2-methylaminoethyl)piperidin-4-yl ester (9.58 g, 27.11 mmol, 1 eq; prepared as described in Preparation 6) were dissolved in a solution of DCM (100 mL) and DMF (10 mL). DIPEA (14 mL, 81.33 mmol, 3 eq) was added portionwise and the solution was allowed to stir at room temperature. The reaction mixture was concentrated under vacuum, yielding a yellow oil (34.1 g). The crude oil was dissolved in DCM and washed with H$_2$O:brine (3×, 200 mL) and with brine (1×). The organic layer was concentrated under vacuum to afford biphenyl-2-ylcarbamic acid 1-{2-[(3-formylbenzoyl)methylamino]ethyl}piperidin-4-yl ester as a yellow foam (13.165 g, 98%):

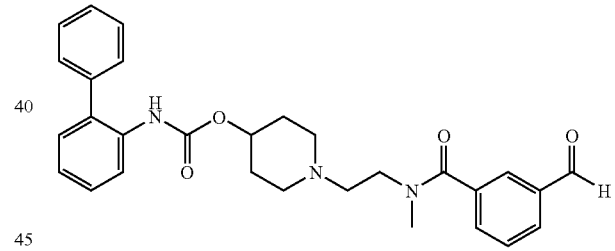

This aldehyde was oxidized to N-{2-[4-(biphenyl-2-ylcarbamoyloxy)piperidin-1-yl]ethyl}-N-methylisophthalamic acid using sulfamic acid (3.95 g, 40.65 mmol, 1.5 eq) and NaClO$_2$ (4.6 g, 40.65 mmol, 1.5 eq, dissolved in 20 mL of H$_2$O) in glacial acetic acid (35 mL) at 0° C. for 40 minutes and at room temperature for 1 hour. After workup, the crude acid was obtained as an orange semi-solid (18.51 g):

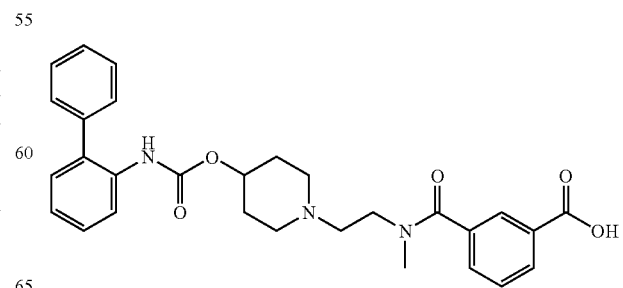

This acid was then coupled with t-butyl n-(2-aminoethyl) carbamate to yield the title compound.

Preparation 8

Biphenyl-2-ylcarbamic Acid 1-(2-{-[3-(2-Aminoethylcarbamoyl)benzoyl]methylamino}ethyl)piperidin-4-yl Ester

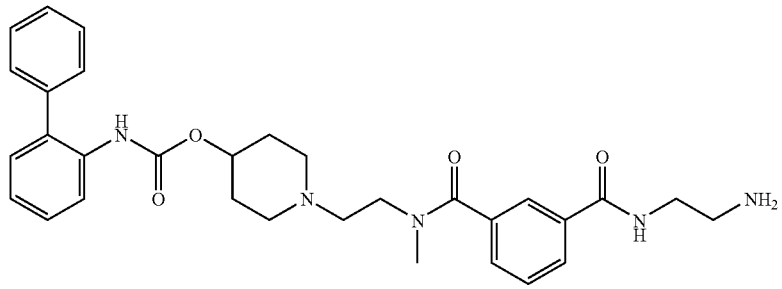

To a solution of the product of Preparation 7 (20.15 g) in 20 mL DCM was added 30 mL TFA in 40 mL DCM. The reaction was stirred at room temperature for 1 hour, followed by concentration under high vacuum using toluene for azeotroph. The crude product was taken up in 200 mL DCM and washed twice with 200 mL solutions of 1:1 brine and 1.0 N NaOH. Additional 1.0 N NaOH was added to achieve a pH of 10. The organic phase was lastly washed with 200 mL brine, dried over $Na_2SO_4$, filtered and concentrated. 16.8 g of the title compound was obtained as an off-white solid in 98% yield. MS m/z: $[M+H^+]$ calcd for $C_{31}H_{37}N_5O_4$, 544.28; found 544.2.

Example 1

Biphenyl-2-ylcarbamic Acid 1-[2-({3-[2-(4-Hydroxybenzylamino) ethylcarbamoyl]benzoyl}methylamino)ethyl]piperidin-4-yl Ester

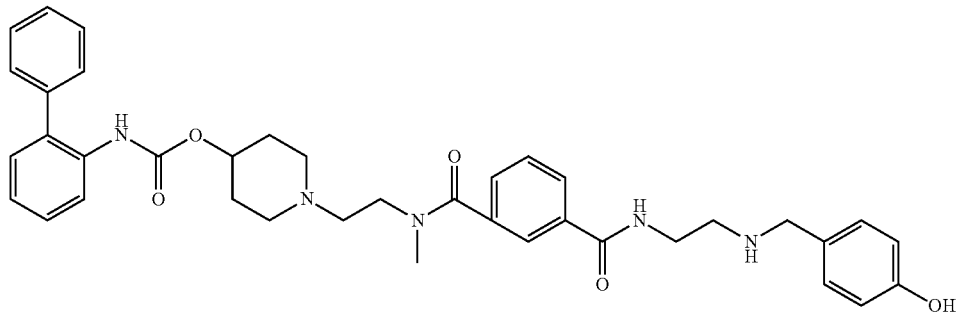

A solution of biphenyl-2-ylcarbamic acid 1-(2-{-[3-(2-aminoethylcarbamoyl)benzoyl]methylamino}ethyl)piperidin-4-yl ester (9.31 g, 17.1 mmol; prepared as described in Preparation 8) and 4-hydroxybenzaldehyde (2.30 g, 18.8 mmol, 1.1 eq) in 125 mL MeOH was stirred at room temperature for 2 hours. $Na(OAc)_3BH$ (7.26 g, 34.2 mmol, 2.0 eq) was added to the reaction at room temperature in two portions separated in one hour interval. The reaction was stirred for an additional hour before being concentrated under vacuum. The residue was taken up in 100 mL DCM and stirred with 100 mL of 1.0 N HCl for 1 hour. The aqueous phase was adjusted to pH 9 using 10.0 N NaOH. The mixture was stirred for an additional 10 minutes. The organic phase was separated, dried over $Na_2SO_4$, filtered and concentrated under vacuum.

The crude material was purified using silica gel chromatography (7% MeOH in $CH_2Cl_2$ with 1% $NH_4OH$ as eluent). The title compound was obtained as an off-white solid (8.08 g, 73%). MS m/z: $[M+H^+]$ calcd for $C_{38}H_{43}N_5O_5$, 650.34; found, 650.2.

Diacetate Salt Crystal

The ester (1.004 g, 1.538 mmol; prepared as described above) was dissolved in 2 mL of MeOH/ACN (1:1). The solution was sonicated and heated until completely clear. To the clear solution was added HOAc (174 μL, 3.06 mmol) and mixed thoroughly with vortex action. Additional ACN (~10 mL) was added drop-wise until the solution turned cloudy. The resulting solution was heated until clear and allowed to sit at room temperature overnight to form white crystalline material. The solid was filtered, washed with ACN (3×10 mL) and dried under vacuum to give the diacetate salt as a white crystalline solid (900 mg, 76%). The diacetate salt can then be used to provide a further purified freebase by a two-step reaction with saturated $NH_4HCO_3$ and MeOH. Crude free base having 91% purity was treated with HOAc and MeOH/ACN to yield a diacetate salt having approximately 97% purity, which was then treated with saturated $NH_4HCO_3$ and MeOH to yield a pure free base having 98+% purity.

A PXRD patterns was obtained with a Rigaku diffractometer using Cu Kα (30.0 kV, 15.0 mA) radiation, and the analysis performed with the goniometer running in continuous-scan mode of 3° per minute with a step size of 0.03° over a range of 2 to 45°. Samples were prepared on quartz specimen holders as a thin layer of powdered material. The instrument was calibrated with a silicon metal standard. The crystalline diacetate salt is characterized by a PXRD pattern in which the peak positions are substantially in accordance with those shown in FIG. 1. Those peaks are listed below, in order of descending relative intensity.

| I % | 2-Theta |
| --- | --- |
| 100 | 9.771 |
| 73.4 | 17.874 |
| 71.9 | 19.522 |
| 30.3 | 23.723 |
| 26.4 | 23.150 |
| 23.2 | 22.191 |
| 22 | 7.372 |
| 21.4 | 26.600 |
| 12.5 | 14.454 |
| 11.1 | 25.939 |
| 10.4 | 24.708 |
| 9.9 | 10.910 |
| 9.5 | 29.001 |
| 8.5 | 4.969 |
| 7.6 | 18.745 |
| 6.7 | 11.658 |
| 6.1 | 21.291 |
| 5.5 | 30.793 |
| 5.2 | 27.296 |
| 4.8 | 20.610 |
| 4.8 | 34.850 |
| 4.1 | 31.642 |
| 3.9 | 13.491 |
| 3.8 | 15.893 |
| 3.3 | 33.026 |
| 2.4 | 37.583 |

Thus, in one embodiment, the crystalline diacetate salt of the present invention is characterized by a powder x-ray diffraction (PXRD) pattern having two or more diffraction peaks at 2θ values selected from 4.97±0.20, 7.37±0.20, 9.77±0.20, 10.91±0.20, 11.66±0.20, 13.49±0.20, 14.45±0.20, 15.89±0.20, 17.87±0.20, 18.75±0.20, 19.52±0.20, 20.61±0.20, 21.29±0.20, 22.19±0.20, 23.15±0.20, 23.72±0.20, 24.71±0.20, 25.94±0.20, 26.60±0.20, 27.30±0.20, 29.00±0.20, 30.79±0.20, 31.64±0.20, 33.03±0.20, 34.85±0.20, and 37.58±0.20; and in a specific embodiment, this crystalline form is characterized by a powder x-ray diffraction pattern comprising diffraction peaks at 2θ values of 4.97±0.20, 7.37±0.20, 9.77±0.20, 10.91±0.20, 14.45±0.20, 17.87±0.20, 18.75±0.20, 19.52±0.20, 22.19±0.20, 23.15±0.20, 23.72±0.20, 24.71±0.20, 25.94±0.20, 26.60±0.20, and 29.00±0.20.

Figure 2:
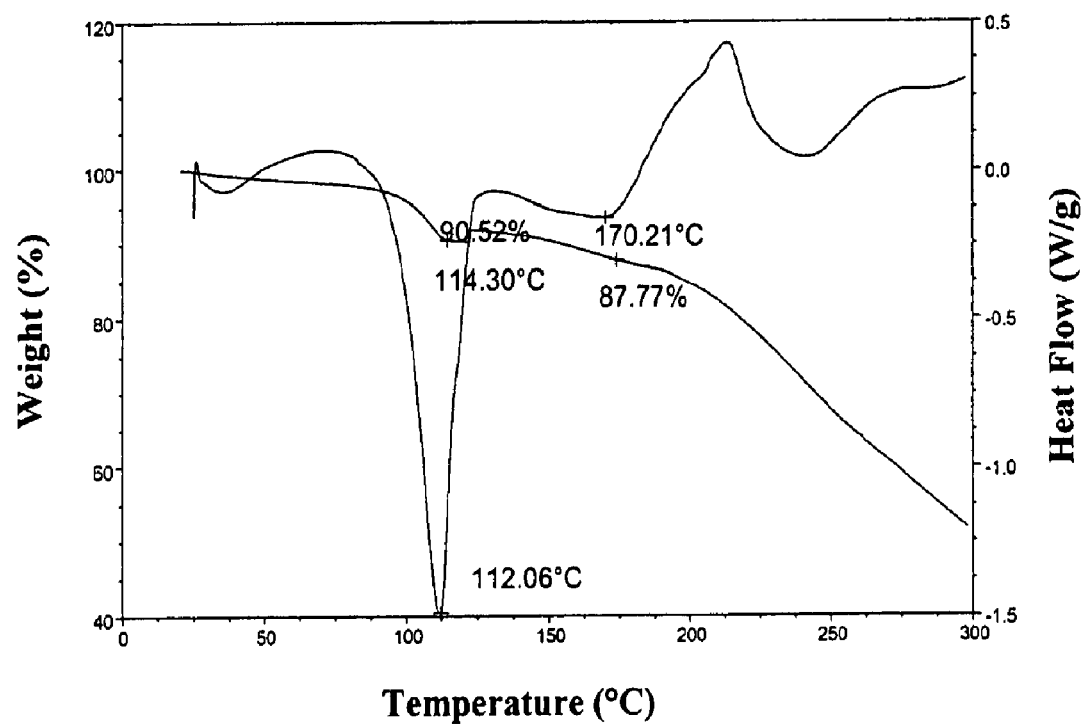
FIG. 2 shows a differential scanning calorimetry (DSC) trace and a thermal gravimetric analysis (TGA) trace for this crystalline salt.

DSC was performed using a TA Instruments Model Q-10 module with a Thermal Analyst controller, and data were collected and analyzed using TA Instruments Thermal Solutions software. A sample of about 1 mg of the crystalline diacetate salt was accurately weighed into an aluminum pan with lid, and evaluated using a linear heating ramp of 10° C./min from ambient temperature to approximately 300° C. The DSC cell was purged with dry nitrogen during use. A representative DSC trace for this salt is shown in FIG. 2 and depicts one transition at about 114° C., no thermal decomposition below about 160° C., and maximum endothermic heat flow at about 112° C. This diacetate salt had a melting point of about 114° C.

TGA was performed using a TA Instruments Model Q-50 module equipped with high resolution capability, and data were collected and analyzed using TA Instruments Thermal Solutions software. A sample of the crystalline diacetate salt weighing about 2 mg was placed onto a platinum pan and scanned with a high resolution-heating rate from ambient temperature to 300° C. The balance and furnace chambers were purged with nitrogen flows during use. A representative TGA trace for this salt is shown in FIG. 2 and shows a loss of solvents and/or water (9%) at temperatures below about 115° C.

Ion analysis of the crystalline diacetate salt determined 15.3% w/w acetate (calculated value: 15.6% w/w).

A dynamic moisture sorption (DMS) assessment (also known as a moisture sorption-desorption profile) was performed for samples of the crystalline diacetate salt using a VTI atmospheric microbalance, SGA-100 system (VTI Corp., Hialeah, Fla. 33016). A sample size of approximately 10 mg was used and the humidity was set at the ambient value at the start of the analysis. A typical DMS analysis consisted of three scans: ambient to 2% relative humidity (RH), 2% RH to 90% RH, 90% RH to 5% RH at a scan rate of 5% RH/step. The mass was measured every two minutes and the RH was changed to the next value (+/−5% RH) when the mass of the sample was stable to within 0.01% for 5 consecutive points. A representative DMS trace for a sample of this crystalline salt showed a reversible sorption/desorption profile with less than about 18% weight gain when exposed to up to 90% RH.

Monooxalate Salt Crystal

The ester (1 g, 1.54 mmol; prepared as described above) was dissolved in 1 mL of MeOH/ACN (1:1). The solution was sonicated until completely clear. To the solution was added oxalic acid in EtOH (1M, 1.54 mL, 1 eq) followed by ACN until the solution became cloudy (~8 mL). The cloudy solution was stirred at 50° C. for 1.5 hours and slowly cooled to room temperature under stirring. The solid was filtered, washed with ACN (5 mL×3) and dried under high vacuum to give the monooxalate salt as a white crystalline solid (0.8 g, 70%).

Figure 3:
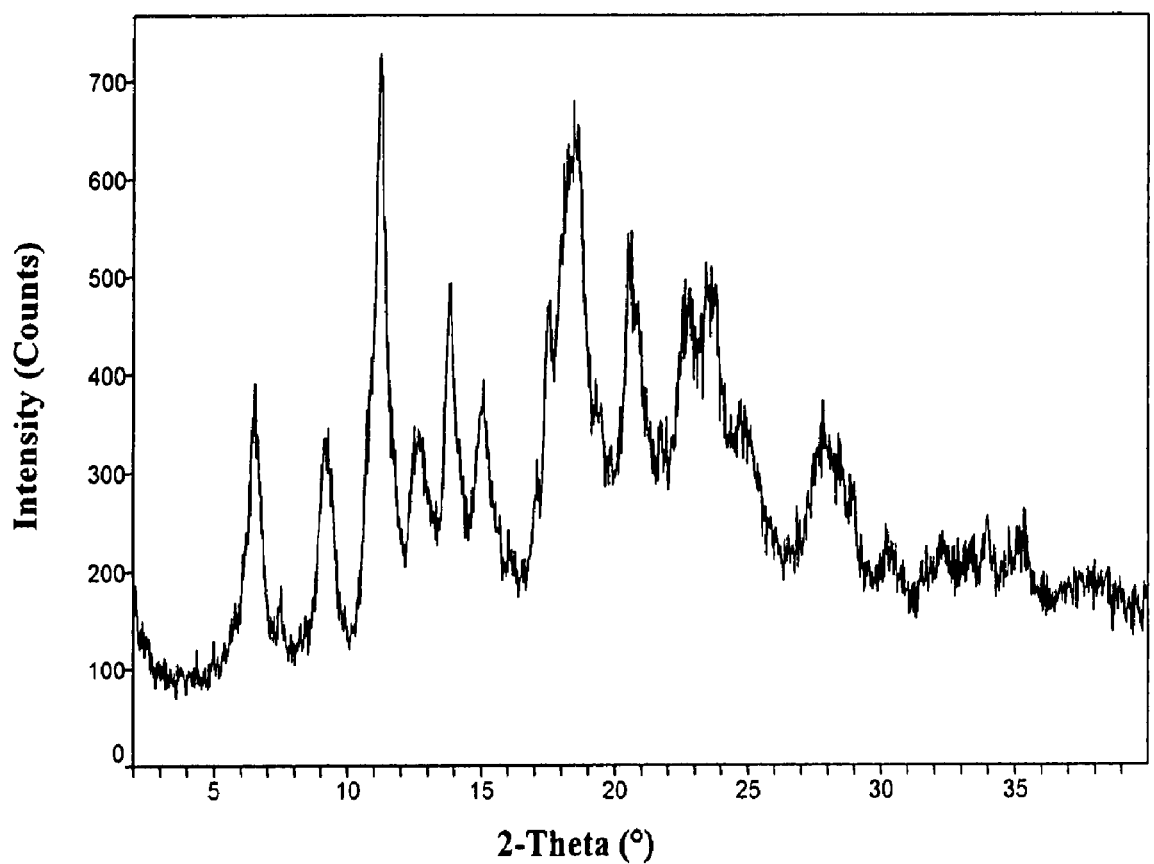
FIG. 3 shows a PXRD pattern of a crystalline monooxalate salt of the compound of Example 1. DSC and TGA traces for this crystalline salt are shown in FIG. 4.

The crystalline monooxalate salt is characterized by a PXRD pattern in which the peak positions are substantially in accordance with those shown in FIG. 3. Those peaks are listed below, in order of descending relative intensity.

| I % | 2-Theta |
| --- | --- |
| 100 | 6.448 |
| 86.1 | 20.582 |
| 78.9 | 11.039 |
| 74 | 27.571 |
| 67.8 | 18.120 |
| 62.1 | 23.042 |
| 53.7 | 25.620 |
| 46.3 | 24.032 |
| 36.7 | 12.866 |
| 36.3 | 15.420 |
| 32.3 | 14.760 |
| 24.5 | 19.379 |
| 24.1 | 21.721 |
| 23.1 | 34.324 |
| 21.1 | 13.683 |
| 20 | 12.390 |
| 19 | 9.121 |
| 16.8 | 32.274 |
| 13.7 | 35.546 |
| 11.3 | 37.855 |
| 9.9 | 32.632 |
| 8.7 | 36.739 |

Figure 4:
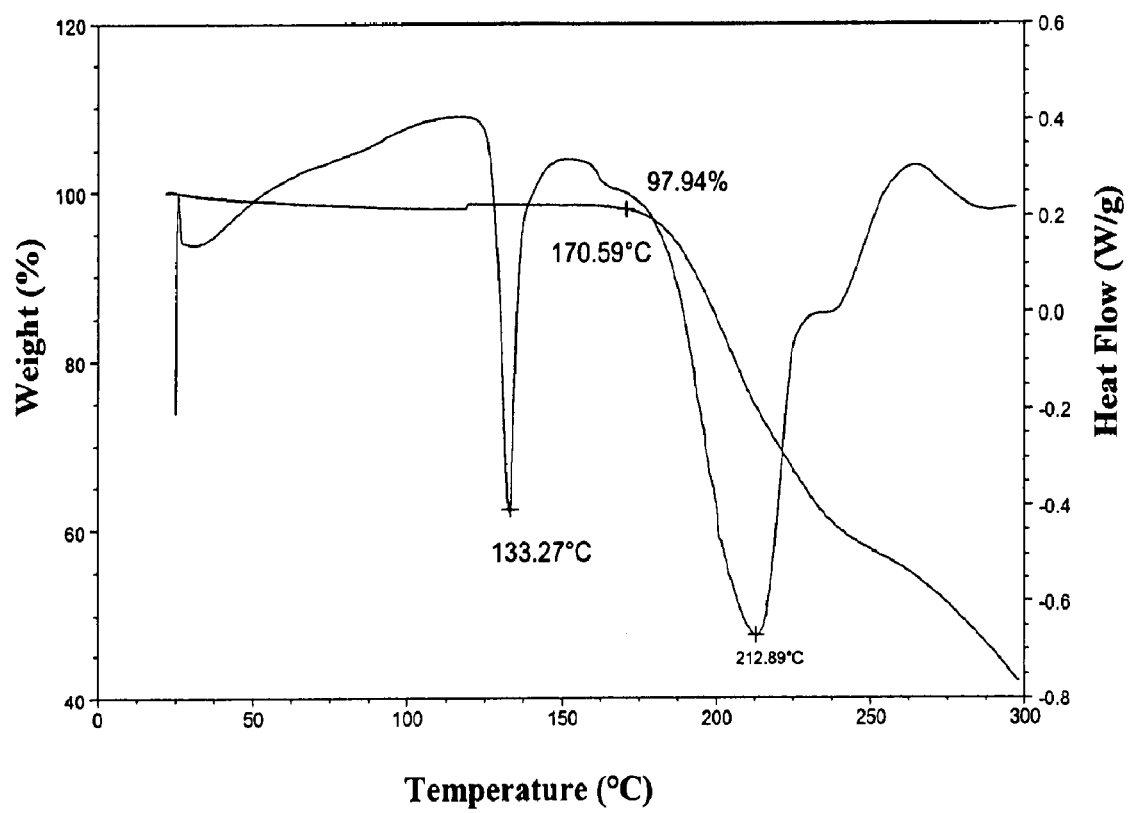

Thus, in one embodiment, the crystalline monooxalate salt of the present invention is characterized by a powder x-ray diffraction (PXRD) pattern having two or more diffraction peaks at 2θ values selected from 6.45±0.20, 9.121±0.20, 11.04±0.20, 12.39±0.20, 12.87±0.20, 13.68±0.20, 14.76±0.20, 15.42±0.20, 18.12±0.20, 19.38±0.20, 20.58±0.20, 21.72±0.20, 23.04±0.20, 24.03±0.20, 25.62±0.20, 27.57±0.20, 32.27±0.20, 32.63±0.20, 34.32±0.20, 35.55±0.20, 36.74±0.20, and 37.86±0.20; and in a specific embodiment, this crystalline form is characterized by a powder x-ray diffraction pattern comprising diffraction peaks at 2θ values of 6.45±0.20, 11.04±0.20, 12.87±0.20, 13.68±0.20, 14.76±0.20, 15.42±0.20, 18.12±0.20, 19.38±0.20, 20.58±0.20, 21.72±0.20, 23.04±0.20, 24.03±0.20, 25.62±0.20, 27.57±0.20 and 34.32±0.20. A representative DSC trace of the crystalline monooxalate salt is shown in FIG. 4 and depicts one transition at about 133° C., and no thermal decomposition below about 150° C. FIG. 4 also depicts a representative TGA trace of this salt, which shows a loss of solvents and/or water (2%) at temperatures below about 170° C. Ion analysis of this crystalline salt determined 11.86% w/w oxalate (calculated value: 12.16% w/w). A representative DMS trace for a sample of this crystalline salt showed a reversible sorption/desorption profile with less than about 14% weight gain when exposed to up to 90% RH. This monooxalate salt had a melting point of about 134° C.

Dipropionate Salt Crystal

The ester (107 mg, 0.165 mmol; prepared as described above) was dissolved in 4 mL of ACN. The solution was sonicated and heated until completely clear. Propionic acid (25 mL, 0.33 mmol) was added to the solution and the solution turned to cloudy. MeOH (50 mL) was added in and the solution was stirred at 50° C. until it was completely clear. The solution was slowly cooled down to room temperature and stirred overnight to form a white crystalline material. The solid was filtered, washed with ACN (0.5 mL×3) and dried under vacuum to give the dipropionate salt as a white crystalline solid (82.3 mg, 63%).

Figure 5:
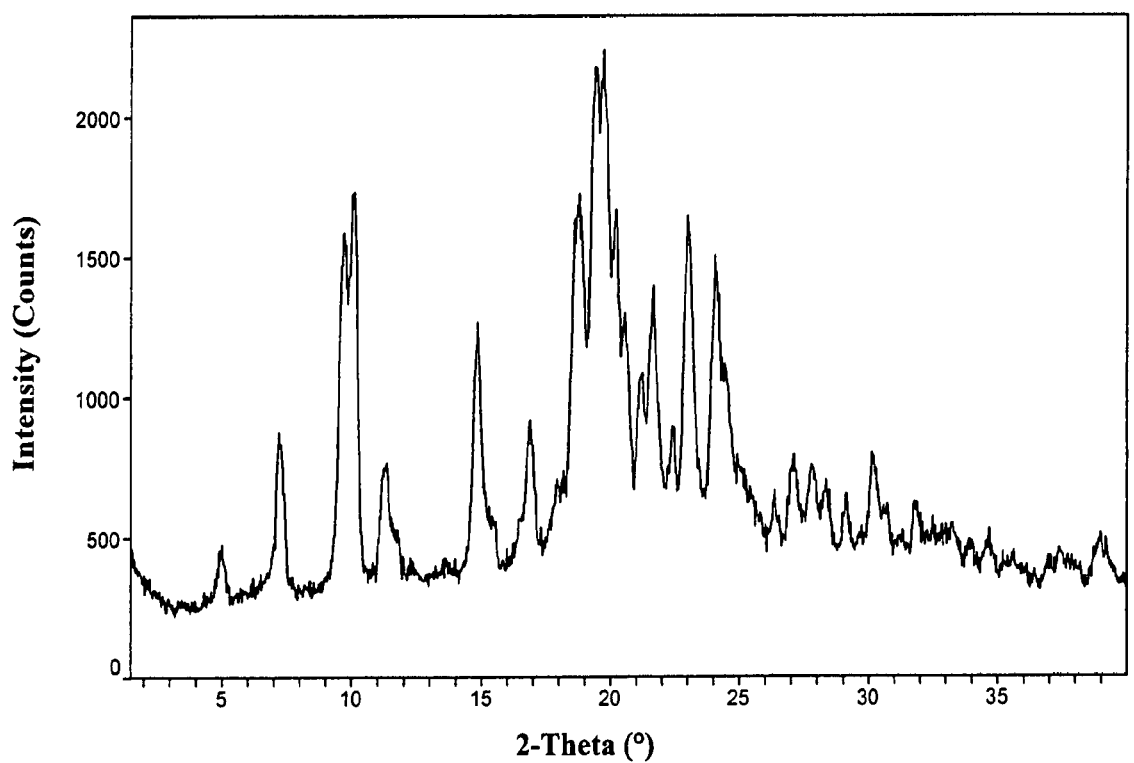
FIG. 5 shows a PXRD pattern of a crystalline dipropionate salt of the compound of Example 1. DSC and TGA traces for this crystalline salt are shown in FIG. 6.

The crystalline dipropionate salt is characterized by a PXRD pattern in which the peak positions are substantially in accordance with those shown in FIG. 5. Those peaks are listed below, in order of descending relative intensity.

| I % | 2-Theta |
| --- | --- |
| 100 | 10.108 |
| 91.2 | 9.691 |
| 84.9 | 19.381 |
| 82 | 18.751 |
| 69.4 | 23.012 |
| 66.8 | 20.218 |
| 65.4 | 14.850 |
| 59.6 | 24.063 |
| 48 | 21.659 |
| 41.7 | 7.201 |
| 34.6 | 16.889 |
| 31.8 | 24.479 |
| 29.2 | 11.338 |
| 24.8 | 21.234 |
| 24.5 | 30.125 |
| 19.3 | 27.781 |
| 16.7 | 27.090 |
| 15 | 28.348 |
| 14.3 | 20.553 |
| 13.9 | 29.107 |
| 13.6 | 5.007 |
| 13.4 | 22.418 |
| 12.9 | 38.968 |
| 12.3 | 15.420 |

-continued

| I % | 2-Theta |
| --- | --- |
| 11.7 | 26.364 |
| 10.9 | 11.759 |
| 10.5 | 30.719 |
| 10.5 | 31.775 |
| 10.3 | 34.676 |
| 9.3 | 37.381 |
| 7.9 | 32.482 |
| 6.6 | 35.604 |
| 5.8 | 39.294 |
| 5.5 | 33.894 |
| 4.8 | 36.954 |

Figure 6:
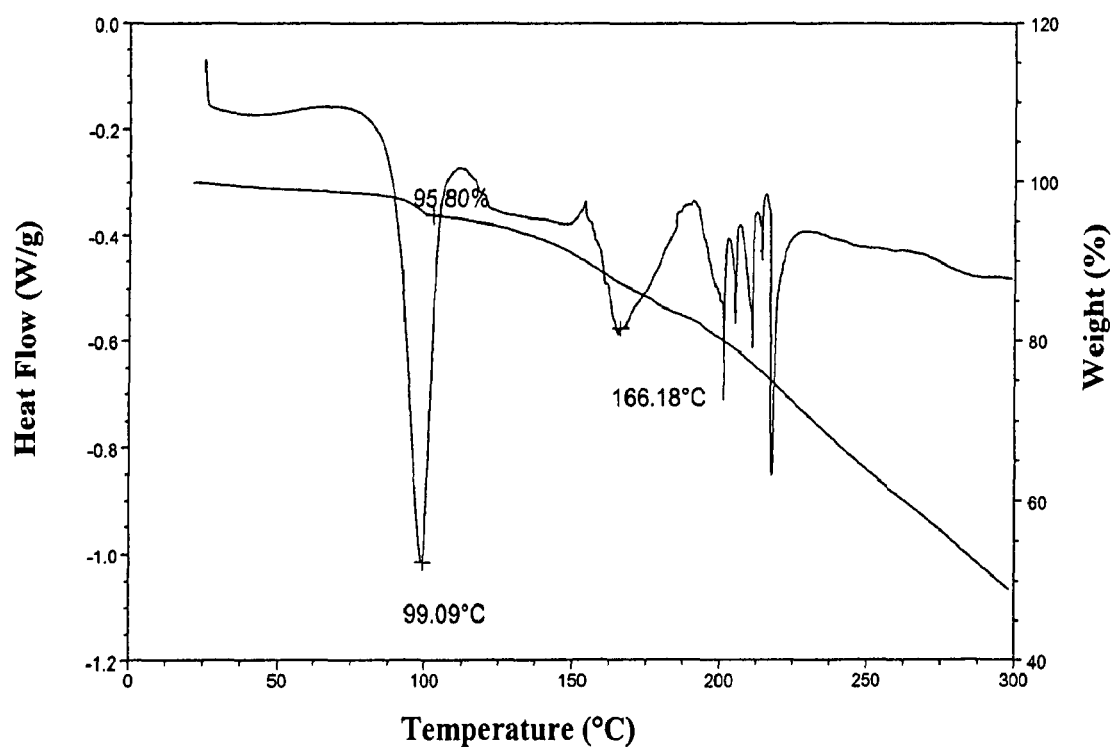

Thus, in one embodiment, the crystalline dipropionate salt of the present invention is characterized by a powder x-ray diffraction (PXRD) pattern having two or more diffraction peaks at 2θ values selected from 5.01±0.20, 7.20±0.20, 9.69±0.20, 10.11±0.20, 11.34±0.20, 11.76±0.20, 14.85±0.20, 15.42±0.20, 16.89±0.20, 18.75±0.20, 19.38±0.20, 20.22±0.20, 20.55±0.20, 21.23±0.20, 21.66±0.20, 22.42±0.20, 23.01±0.20, 24.06±0.20, 24.48±0.20, 26.36±0.20, 27.09±0.20, 27.78±0.20, 28.35±0.20, 29.11±0.20, 30.13±0.20, 30.72±0.20, 31.78±0.20, 32.48±0.20, 33.89±0.20, 34.68±0.20, 35.60±0.20, 36.95±0.20, 37.38±0.20, 38.97±0.20, and 39.29±0.20; and in a specific embodiment, this crystalline form is characterized by a powder x-ray diffraction pattern comprising diffraction peaks at 2θ values of 7.20±0.20, 9.69±0.20, 10.11±0.20, 11.34±0.20, 14.85±0.20, 16.89±0.20, 18.75±0.20, 19.38±0.20, 20.22±0.20, 21.23±0.20, 21.66±0.20, 23.01±0.20, 24.06±0.20, 24.48±0.20, and 30.13±0.20. A representative DSC trace of the crystalline dipropionate salt is shown in FIG. 6 and depicts one transition at about 100° C., no thermal decomposition below about 150° C., and maximum endothermic heat flow at about 99° C. This dipropionate salt had a melting point of about 100° C. FIG. 6 also depicts a representative TGA trace of this salt, which shows a loss of solvents and/or water (5%) at temperatures below about 100° C. Ion analysis of this crystalline salt determined 18.85% w/w propionate (calculated value: 18.5% w/w). A representative DMS trace for a sample of this crystalline salt showed a reversible sorption/desorption profile with less than about 11% weight gain when exposed to up to 90% RH.

Hemiedisylate Salt Crystal

The ester (1.07 g, 1.66 mmol amorphous freebase; prepared as described above) was dissolved in a round bottom flask in a solvent mixture of 20% MeOH and 80% ACN (10 mL). A free acid solution of 1,2 ethane disulfonic acid (½ equivalent of acid, 0.19 g, 0.83 mmol) was dissolved in the same solvent system (20% MeOH, 80% ACN, 1 mL). The acid solution was added drop wise to the freebase solution over 10 minutes, while stirring at approximately 22° C. Once the acid was completely fed to the flask, the liquor appeared cloudy-white. The liquor was heated to 50° C. for one-half hour, then slowly cooled to 22° C. Agitation was continued for 2 hours to enable greater recovery and growth of the crystals. The crystals were recovered from the slurry by vacuum filtration, and the cake was washed with ACN (1 mL×3), followed by vacuum drying. The yield was 87.6% with respect to the freebase starting material. HPLC, XRPD, NMR and ion analysis confirmed this was a crystalline hemiedisylate salt.

Heminapadisylate Methanolate Crystal

The ester (18.87 g, 29.04 mmol, 98.57% pure amorphous freebase; prepared as described above) was dissolved in a solvent mixture of 20% MeOH and 80% ACN (250 mL). 1,5 naphthalene disulfonic acid (½ mole equivalent, 4.573 g, 3.97 mmol) was dissolved in 170 mL of equivalent solvent mixture. The acid went into solution after vigorous sonication (heating could alternately be used to speed dissolution of the acid). The overall salt mass to solvent volume ratio was 1:18. The freebase solution was placed in round bottom flask, in a large oil bath. To the freebase solution, the acid solution was added drop wise via an addition funnel, while stirring at room temperature. The acid feed rate was approximately 5 mL per minute. After adding approximately 75 mL of the acid solution the reaction mixture was heated to 30° C. The mixture became partially cloudy at this temperature. After addition of the 170 mL of acid, the solution was heated to 50° C. The mixture was stirred at 50° C. for one-half hour before it was slowly cooled to room temperature, while stirring over night. Over this period, crystallization occurred. The solid was filtered, washed with a solvent mixture containing 10% MeOH/90% ACN (100 mL×3) and a yield of 84% was obtained (freebase equivalent).

Heminapadisylate Ethanolate Crystal

A solid mixture of the ester (75 mg amorphous freebase; prepared as described above) and crystalline 1,5 naphthalene disulphonic acid (20.3 mg) was prepared in a 15 mL vial. The solids were dissolved by adding 2.5 mL of EtOH and heating to 40° C. for 5 minutes. Crystallization was induced by adding 2.5 mL of ACN and cooling to room temperature (approximately 22° C.) and leaving over night. Large birefringent well formed solid particles were obtained. These solids were analyzed by single crystal X-ray diffraction and found to be crystalline heminapadisylate ethanolate ester.

Heminapadisylate Salt Crystal

Crystalline heminapadisylate methanolate, prepared as described above, was converted to the desolvated crystal form of the ester by the following procedure: The filter cake was dried in a vacuum oven at 50° C., with a purging nitrogen flow, overnight, then at 40° C. over 3 days. 19.75 g of the heminapadisylate salt was obtained as a white crystalline solid (84% yield freebase equivalent).

Alternately, the desolvated crystal form was prepared by heating the crystalline heminapadisylate methanolate form in a vacuum oven at 100° C., with a purging nitrogen flow for 4 hours.

Alternately, the desolvated crystal form was prepared reslurrying the crystalline heminapadisylate methanolate form in an excess of ACN (approximately 1-5% solids concentration) at 22° C. for two to four days.

Freebase Crystal (Polymorph Form I)

The ester (20 g amorphous freebase; prepared as described in Example 1) was dissolved in 200 mL of EtOAc and 60 mL of IPA room temperature. The solution was washed with water 2×100 mL. The organic phase was dried over MgSO4 then filtered. A small amount of crystals (90 mg) formed after filtration. The crystals were collected and dried under high vacuum.

Freebase Crystal (Polymorph Form II)

A 200 mg/mL solution was prepared by dissolving 50 mg of the ester (amorphous freebase; prepared as described above) in 0.25 mL of IPA at 22° C. in a glass HPLC vial. After two days, the vial was inspected by stereozoom microscope under polarized light. Birefringent particles were observed, indicating a crystalline morphology. After 7 days from initial dissolution, inspection of the vial found that crystals had continued to grow. The mother liquor was decanted and the crystals were washed with approximately 100-200 µL of 1:1 IPA:water. This material was confirmed to be crystalline by PXRD.

A larger batch was prepared for further characterization, by dissolving 200 mg of the amorphous freebase ester (prepared as described in Example 1) into 1.0 mL of IPA and 20 µL, of water (2% vol/vol), at 22° C. Approximately 1-3 mg of seed crystals from the initial batch was added to the vial. The vial was left at 22° C. overnight, then inspected by stereozoom microscopy with crossed polarizing filters. Birefringent well formed crystals were observed covering the base of the vial). These were further crystallized by cooling at 4° C., before isolation and characterization. HPLC analysis confirmed that the crystalline solid was consistent with the retention time of the parent compound (amorphous freebase ester) and the crystals had a purity of 98.6%, while the mother liquor purity was 96.7%. The amorphous feed material had a purity of 98.4%. Hence there was some purification achieved by crystallization of the freebase ester.

Example 2

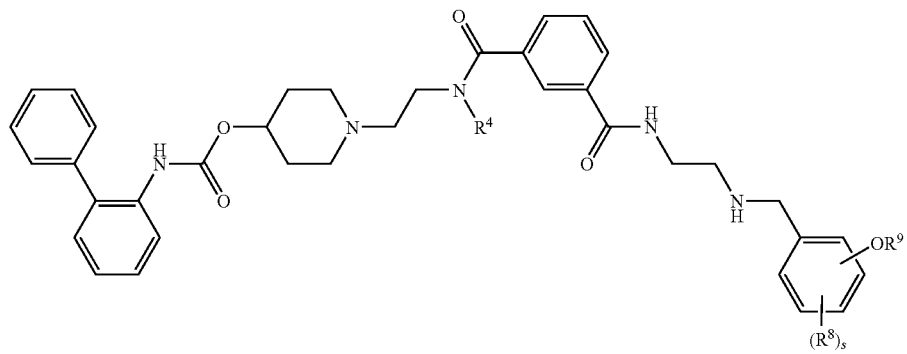

Following the procedure described in Example 1 and substituting the appropriate starting materials and reagents, the following compounds were prepared.

| # | Name | R⁴ | ![structure](OR⁹ phenyl with (R⁸)ₛ) |
|---|------|-----|---|
| 2-1 | Biphenyl-2-ylcarbamic acid 1-[2-({3-[2-(4-hydroxy-3-methoxybenzylamino)ethylcarbamoyl]benzoyl}methylamino)ethyl]piperidin-4-yl ester. MS m/z: [M + H⁺] calcd for $C_{39}H_{45}N_5O_6$, 680.35; found, 680.4. | Me | 4-OH, 3-OCH₃ phenyl |
| 2-2 | Biphenyl-2-ylcarbamic acid 1-[2-({3-[2-(2-hydroxybenzylamino)ethylcarbamoyl]benzoyl}ethylamino)ethyl]piperidin-4-yl ester. MS m/z: [M + H⁺] calcd for $C_{38}H_{43}N_5O_5$, 650.34; found, 650.4. | Me | 2-OH phenyl |
| 2-3 | Biphenyl-2-ylcarbamic acid 1-[2-({3-[2-(4-methoxybenzylamino)ethylcarbamoyl]benzoyl}ethylamino)ethyl]piperidin-4-yl ester. MS m/z: [M + H⁺] calcd for $C_{39}H_{45}N_5O_5$, 664.35; found, 664.4. | Me | 4-OCH₃ phenyl |
| 2-4 | Biphenyl-2-ylcarbamic acid 1-(2-{3-[2-(4-hydroxy-2-methoxybenzylamino)ethylcarbamoyl]benzoylamino}ethyl)piperidin-4-yl ester. MS m/z: [M +H⁺] calcd for $C_{38}H_{43}N_5O_6$, 666.33; found, 666.2. | H | 4-OH, 2-OCH₃ phenyl |
| 2-5 | Biphenyl-2-ylcarbamic acid 1-(2-{3-[2-(2-hydroxybenzylamino)ethylcarbamoyl]benzoylamino}ethyl)piperidin-4-yl ester. MS m/z: [M +H⁺] calcd for $C_{37}H_{41}N_5O_5$, 636.32; found, 636.2. | H | 2-OH phenyl |
| 2-6 | Biphenyl-2-ylcarbamic acid 1-(2-{3-[2-(4-methoxybenzylamino)ethylcarbamoyl]benzoylamino}ethyl)piperidin-4-yl ester. MS m/z: [M +H⁺] calcd for $C_{38}H_{43}N_5O_5$, 650.34; found, 650.2. | H | 4-OCH₃ phenyl |
| 2-7 | Biphenyl-2-ylcarbamic acid 1-[2-({3-[2-(3-hydroxybenzylamino)ethylcarbamoyl]benzoyl}methylamino)ethyl]piperidin-4-yl ester. MS m/z: [M + H⁺] calcd for $C_{38}H_{43}N_5O_5$, 650.34; found, 650.4. | Me | 3-OH phenyl |
| 2-8 | Biphenyl-2-ylcarbamic acid 1-[2-({3-[2-(3-hydroxy-4-methoxybenzylamino)ethylcarbamoyl]benzoyl}methylamino)ethyl]piperidin-4-yl ester. MS m/z: [M + H⁺] calcd for $C_{39}H_{45}N_5O_6$, 680.35; found, 680.4. | Me | 3-OH, 4-OCH₃ phenyl |
| 2-9 | Biphenyl-2-ylcarbamic acid 1-[2-({3-[2-(3,4-dihydroxybenzylamino)ethylcarbamoyl]benzoyl}methylamino)ethyl]piperidin-4-yl ester. MS m/z: [M + H⁺] calcd for $C_{38}H_{43}N_5O_6$, 666.33; found, 666.4. | Me | 3,4-diOH phenyl |

Example 3

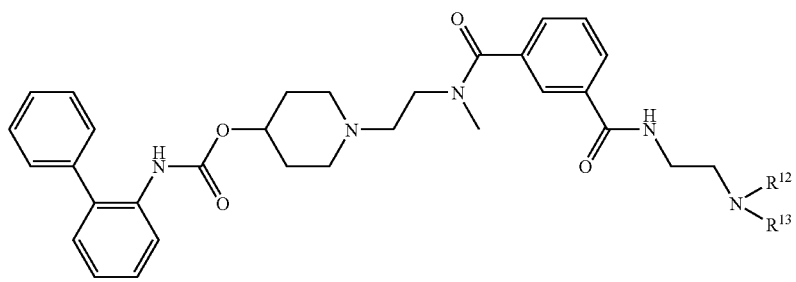

Compound 3-3 was prepared as follows: To a solution of biphenyl-2-ylcarbamic acid 1-(2-{-[3-(2-amino ethylcarbamoyl) benzoyl]methylamino}ethyl)piperidin-4-yl ester (55 mg, 0.1 mmol; prepared as described in Preparation 8) in 1 mL of MeOH was added the appropriated aldehyde (0.1 mmol) at room temperature. The reaction was stirred at room temperature for 30 minutes before it was treated with Na(OAc)$_3$BH (64 mg, 0.3 mmol). Stirring was continued for an additional 1 hour. The reaction mixture was concentrated, then dissolved in 1 mL of 1:1 HOAc/water solution and purified on reverse phase HPLC. Compound 3-3 was obtained as a tri(trifluoroacetate) salt, while compound 3-4 was isolated as a by product.

Compounds 3-1 and 3-2 were also prepared by following a similar procedure and substituting the appropriate aldehyde.

| # | Name | $\begin{array}{c}\phantom{X}R^{12}\\ -N\\ R^{13}\end{array}$ |
|---|------|---|
| 3-1 | Biphenyl-2-ylcarbamic acid 1-{2-[methyl(3-{2-[(thiophen-2-ylmethyl)amino]ethylcarbamoyl}benzoyl)amino]ethyl}piperidin-4-yl ester. MS m/z: [M + H$^+$] calcd for C$_{36}$H$_{41}$N$_5$O$_4$S, 640.30; found, 640.2. | |
| 3-2 | Biphenyl-2-ylcarbamic acid 1-{2-[(3-{2-[(furan-2-ylmethyl)amino]ethyl-carbamoyl}benzoyl)methylamino]ethyl}piperidin-4-yl ester. MS m/z: [M + H$^+$] calcd for C$_{36}$H$_{41}$N$_5$O$_5$, 624.32; found, 624.2. | |
| 3-3 | Biphenyl-2-ylcarbamic acid 1-{2-[(3-{2-[(1H-imidazol-2-ylmethyl)amino]ethyl-carbamoyl}benzoyl)methylamino]ethyl}piperidin-4-yl ester. MS m/z: [M + H$^+$] calcd for C$_{35}$H$_{41}$N$_7$O$_4$, 624.33; found, 624.4. | |
| 3-4 | Biphenyl-2-ylcarbamic acid 1-{2-[(3-{2-[bis-(1H-imidazol-2-ylmethyl)amino]ethyl-carbamoyl}benzoyl)methylamino]ethyl}piperidin-4-yl ester. MS m/z: [M + H$^+$] calcd for C$_{39}$H$_{45}$N$_9$O$_4$, 704.37. | |

Example 4

| # | Name | Y |
|---|------|---|
| 4-1 | Biphenyl-2-ylcarbamic acid 1-[2-({5-[2-(4-hydroxybenzylamino)ethylcarbamoyl] thiophene-2-carbonyl}methylamino)ethyl]piperidin-4-yl ester. MS m/z: [M + H$^+$] calcd for C$_{36}$H$_{41}$N$_5$O$_5$S, 656.29; found, 656.2. | |
| 4-2 | Biphenyl-2-ylcarbamic acid 1-{2-[methyl-(5-{2-[(pyridin-4-ylmethyl)amino]ethylcarbamoyl}thiophene-2-carbonyl)amino]ethyl}piperidin-4-yl ester. MS m/z: [M + H$^+$] calcd for C$_{35}$H$_{40}$N$_6$O$_4$S, 641.29; found, 641.2. | |

Example 5

To a solution of compound A (R$^4$=H, 1 g, 2.95 mmol) and 3-nitrobenzoic acid (0.59 g, 3.54 mmol) in DCM (30 mL) were added EDCI (0.85 g, 4.43 mmol), HOBT (0.6 g, 4.43 mmol) and DIPEA (1 mL, 5.9 mmol). The reaction was stirred at room temperature overnight before it was taken up in 50 mL of DCM. The mixture was washed with water 2×100 mL. Organic phase was dried over MgSO$_4$ and concentrated to give crude compound B (R$^4$=H) as a pale yellow solid in quantitative yield:

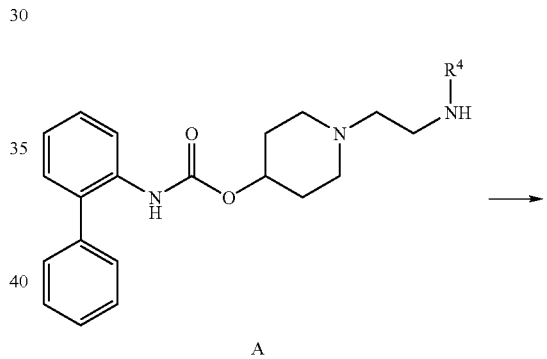

A

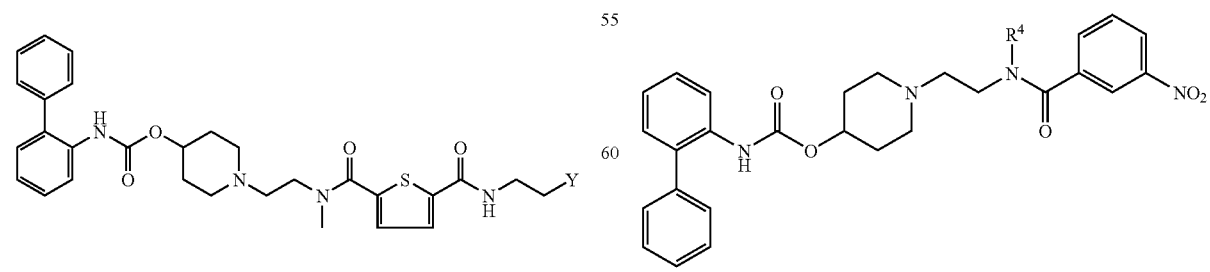

B

Following the procedures described in the previous examples, and substituting the appropriate starting materials and reagents, the following compounds were prepared.

The solution of compound B (R[4]=H, 1.45 g, 2.95 mmol) in 100 mL MeOH was stirred under $H_2$ atmosphere in the presence of Pd catalyst (10% Pd/C, 300 mg) at room temperature for overnight. The catalyst was removed by filtration and the solvent was concentrated to give crude C(R[4]=H, 1.46 g, 108%) as an off-white solid.

To the solution of compound C(R[4]=H, 243 mg, 0.53 mmol) in 5 mL of DCM was added 3-chloropropionyl chloride (compound D, r=1; 0.066 mL, 0.69 mmol) followed by DIPEA (0.276 mL, 1.59 mmol). The reaction was stirred at room temperature for 2 hours before it was concentrated. The residue was dissolved in ACN (6 mL). An aliquot (1 mL) of the solution was treated with 4-hydroxybenzylamine (2 mmol) at 50° C. for 3 hours. The reaction was concentrated and purified via HPLC to give compound 5-1 as a bis(trifluoroacetate) salt.

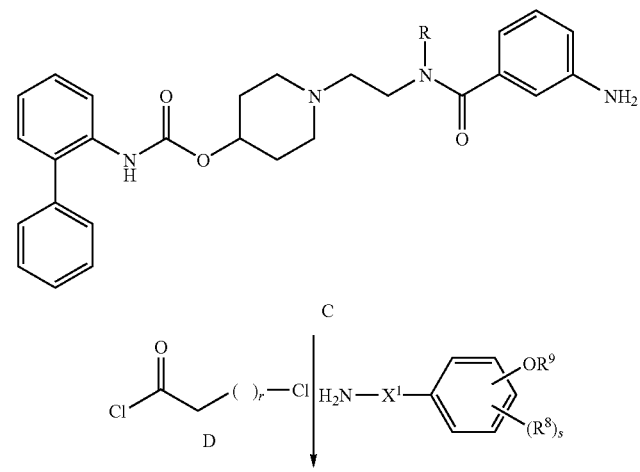

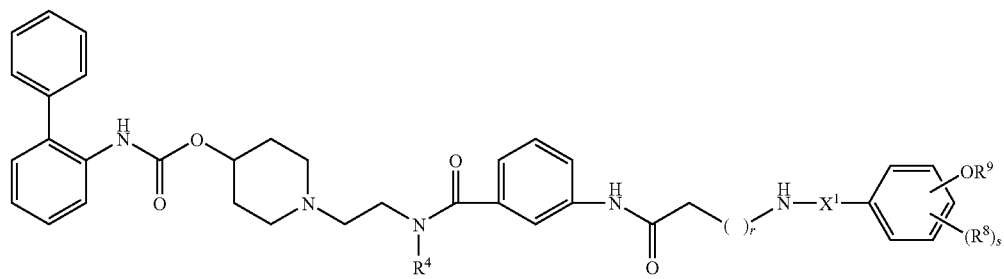

Compounds 5-2 to 5-7 were prepared by following a similar procedure and substituting the appropriate starting materials and reagents.

| # | Name | $R^4$ | r | —X¹—⟨Ar⟩(OR⁹)(R⁸)$_s$ |
|---|---|---|---|---|
| 5-1 | Biphenyl-2-ylcarbamic acid 1-(2-{3-[3-(4-hydroxybenzylamino)propionylamino]benzoylamino}ethyl)piperidin-4-yl ester. MS m/z: [M + H⁺] calcd for $C_{37}H_{41}N_5O_5$, 636.32; found, 636.4. | H | 1 | —CH₂—C₆H₄—OH |
| 5-2 | Biphenyl-2-ylcarbamic acid 1-[2-(3-{3-[2-(4-hydroxyphenyl)ethylamino]propionylamino}benzoylamino)ethyl]piperidin-4-yl ester. MS m/z: [M + H⁺] calcd for $C_{38}H_{43}N_5O_5$, 650.34; found, 650.2. | H | 1 | —CH₂CH₂—C₆H₄—OH |
| 5-3 | Biphenyl-2-ylcarbamic acid 1-[2-({3-[3-(4-hydroxybenzylamino)propionylamino]benzoyl}methylamino)ethyl]piperidin-4-yl ester. MS m/z: [M + H⁺] calcd for $C_{38}H_{43}N_5O_5$, 650.34; found, 650.2. | Me | 1 | —CH₂—C₆H₄—OH |
| 5-4 | Biphenyl-2-ylcarbamic acid 1-{2-[(3-{3-[2-(4-hydroxyphenyl)ethylamino]propionylamino}benzoyl)methylamino]ethyl}piperidin-4-yl ester. MS m/z: [M + H⁺] calcd for $C_{39}H_{45}N_5O_5$, 664.35; found, 664.2. | Me | 1 | —CH₂CH₂—C₆H₄—OH |
| 5-5 | Biphenyl-2-ylcarbamic acid 1-[2-({3-[2-(4-hydroxybenzylamino)acetylamino]benzoyl}methylamino)ethyl]piperidin-4-yl ester. MS m/z: [M + H⁺] calcd for $C_{37}H_{41}N_5O_5$, 636.32; found, 636.4. | Me | 0 | —CH₂—C₆H₄—OH |
| 5-6 | Biphenyl-2-ylcarbamic acid 1-{2-[(3-{2-[2-(4-hydroxyphenyl)ethylamino]acetylamino}benzoyl)methylamino]ethyl}piperidin-4-yl ester. MS m/z: [M + H⁺] calcd for $C_{38}H_{43}N_5O_5$, 650.34; found, 650.2. | Me | 0 | —CH₂CH₂—C₆H₄—OH |
| 5-7 | Biphenyl-2-ylcarbamic acid 1-[2-(3-{2-[2-(4-hydroxyphenyl)ethylamino]acetylamino}benzoylamino)ethyl]piperidin-4-yl ester. MS m/z: [M + H⁺] calcd for $C_{37}H_{41}N_5O_5$, 636.32; found, 636.2. | H | 0 | —CH₂CH₂—C₆H₄—OH |

Example 6

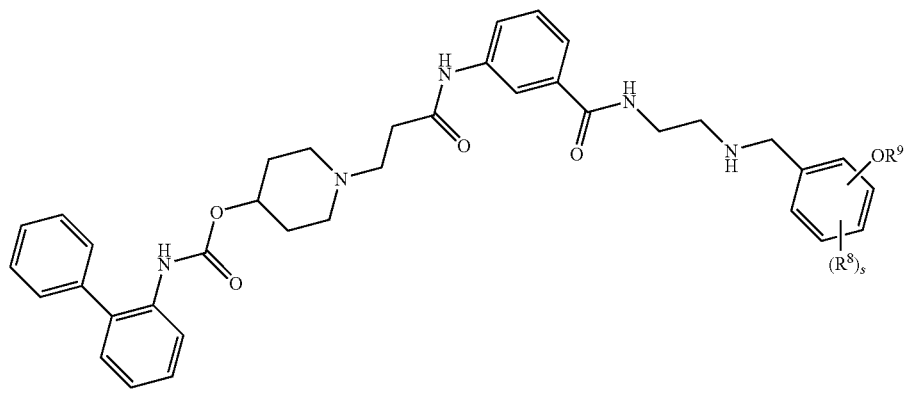

Following the procedures described in the previous examples and substituting the appropriate starting materials and reagents, the following compounds were prepared.

| # | Name | Structure |
|---|---|---|
| 6-1 | Biphenyl-2-ylcarbamic acid 1-(2-{3-[2-(4-hydroxybenzylamino)ethylcarbamoyl]phenylcarbamoyl}ethyl)piperidin-4-yl ester. MS m/z: [M + H$^+$] calcd for C$_{37}$H$_{41}$N$_5$O$_5$, 636.32; found, 636.2. | 4-hydroxybenzyl |
| 6-2 | Biphenyl-2-ylcarbamic acid 1-(2-{3-[2-(4-hydroxy-3-methoxybenzylamino)ethylcarbamoyl]phenylcarbamoyl}ethyl) piperidin-4-yl ester. MS m/z: [M + H$^+$] calcd for C$_{38}$H$_{43}$N$_5$O$_6$, 666.33; found, 666.2. | 4-hydroxy-3-methoxybenzyl |
| 6-3 | Biphenyl-2-ylcarbamic acid 1-(2-{3-[2-(2-hydroxybenzylamino)ethylcarbamoyl]phenylcarbamoyl}ethyl)piperidin-4-yl ester. MS m/z: [M + H$^+$] calcd for C$_{37}$H$_{41}$N$_5$O$_5$, 636.32; found, 636.2. | 2-hydroxybenzyl |

| # | Name | Structure |
|---|---|---|
| 7-1 | Biphenyl-2-ylcarbamic acid 1-(2-{3-[3-(4-hydroxybenzylamino)propionylamino]phenylcarbamoyl}ethyl) piperidin-4-yl ester. MS m/z: [M + H$^+$] calcd for C$_{37}$H$_{41}$N$_5$O$_5$, 636.32; found, 636.2. | 4-hydroxybenzyl |
| 7-2 | Biphenyl-2-ylcarbamic acid 1-(2-{3-[3-(4-hydroxy-3-methoxybenzylamino)propionylamino]phenylcarbamoyl}ethyl)piperidin-4-yl ester. MS m/z: [M + H$^+$] calcd for C$_{38}$H$_{43}$N$_5$O$_6$, 666.33; found, 666.2. | 4-hydroxy-3-methoxybenzyl |
| 7-3 | Biphenyl-2-ylcarbamic acid 1-(2-{3-[3-(2-hydroxybenzylamino)propionylamino]phenylcarbamoyl}ethyl)piperidin-4-yl ester. MS m/z: [M + H$^+$] calcd for C$_{37}$H$_{41}$N$_5$O$_5$, 636.32; found, 636.2. | 2-hydroxybenzyl |

Example 7

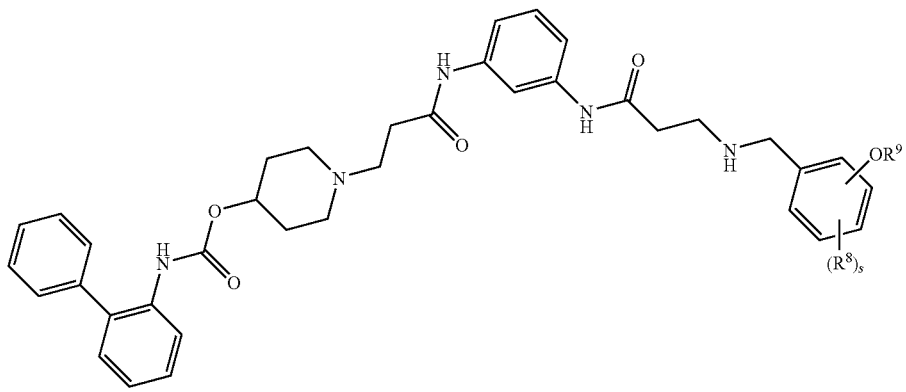

Following the procedures described in the proceeding examples, and substituting the appropriate starting materials and reagents, the following compounds were prepared.

Example 8

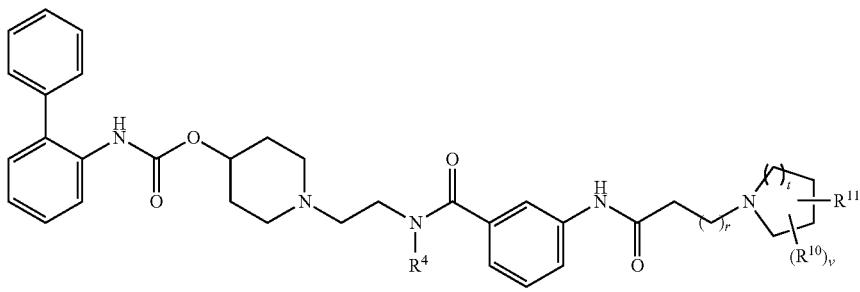

Following the procedures described in the previous examples, and substituting the appropriate starting materials and reagents, the following compounds were prepared.

| # | Name | $R^4$ | r | |
|---|---|---|---|---|
| 8-1 | Biphenyl-2-ylcarbamic acid 1-(2-{methyl-[3-(3-pyrrolidin-1-ylpropionylamino)benzoyl]amino}ethyl)piperidin-4-yl ester. MS m/z: [M + H$^+$] calcd for C$_{35}$H$_{43}$N$_5$O$_5$, 598.34; found, 598.2. | Me | 1 | pyrrolidine |
| 8-2 | Biphenyl-2-ylcarbamic acid 1-{2-[3-(3-pyrrolidin-1-ylpropionylamino)benzoylamino]ethyl}piperidin-4-yl ester. MS m/z: [M + H$^+$] calcd for C$_{34}$H$_{41}$N$_5$O$_4$, 584.33; found, 584.4. | H | 1 | pyrrolidine |
| 8-3 | Biphenyl-2-ylcarbamic acid 1-[2-({3-[3-(4-carbamoyl-piperidin-1-yl)propionyl-amino]benzoyl}methylamino)ethyl]piperidin-4-yl ester. MS m/z: [M + H$^+$] calcd for C$_{37}$H$_{46}$N$_6$O$_5$, 655.36; found, 655.4. | Me | 1 | 4-carbamoylpiperidine |
| 8-4 | Biphenyl-2-ylcarbamic acid 1-(2-{3-[3-(4-carbamoyl-piperidin-1-yl)propionyl-amino]benzoylamino}ethyl)piperidin-4-yl ester. MS m/z: [M + H$^+$] calcd for C$_{36}$H$_{44}$N$_6$O$_5$, 641.35; found, 641.2. | H | 1 | 4-carbamoylpiperidine |
| 8-5 | Biphenyl-2-ylcarbamic acid 1-(2-{methyl[3-(2-pyrrolidin-1-yl-acetylamino)benzoyl]amino}ethyl)piperidin-4-yl ester. MS m/z: [M + H$^+$] calcd for C$_{34}$H$_{41}$N$_5$O$_4$, 584.33; found, 584.2. | Me | 0 | pyrrolidine |
| 8-6 | Biphenyl-2-ylcarbamic acid 1-[2-({3-[2-(4-hydroxy-piperidin-1-yl)acetylamino]benzoyl}methylamino)ethyl]piperidin-4-yl ester. MS m/z: [M + H$^+$] calcd for C$_{35}$H$_{43}$N$_5$O$_5$, 614.34; found, 614.4. | Me | 0 | 4-hydroxypiperidine |
| 8-7 | Biphenyl-2-ylcarbamic acid 1-{2-[3-(2-pyrrolidin-1-yl-acetylamino)benzoylamino]ethyl}piperidin-4-yl ester. MS m/z: [M + H$^+$] calcd for C$_{33}$H$_{39}$N$_5$O$_4$, 570.31; found, 570.2. | H | 0 | pyrrolidine |
| 8-8 | Biphenyl-2-ylcarbamic acid 1-(2-{3-[2-(4-hydroxy-piperidin-1-yl)acetylamino]benzoylamino}ethyl)piperidin-4-yl ester. MS m/z: [M + H$^+$] calcd for C$_{34}$H$_{41}$N$_5$O$_5$, 560.32; found, 600.2. | H | 0 | 4-hydroxypiperidine |
| 8-9 | Biphenyl-2-ylcarbamic acid 1-(2-{3-[2-(4-carbamoyl-piperidin-1-yl)acetylamino]benzoylamino}ethyl)piperidin-4-yl ester. MS m/z: [M + H$^+$] calcd for C$_{35}$H$_{42}$N$_6$O$_5$, 627.33; found, 627.2. | H | 0 | 4-carbamoylpiperidine |

Example 9

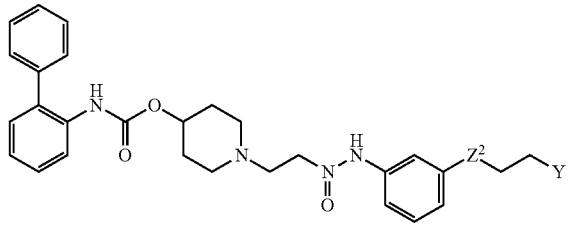

Following the procedures described in the previous examples, and substituting the appropriate starting materials and reagents, the following compounds were prepared.

| # | Name | $Z^2$ | $-N(R^{12})(R^{13})$ on methyl |
|---|---|---|---|
| 9-1 | Biphenyl-2-ylcarbamic acid 1-(2-{3-[2-(cyclopropyl-methylamino)ethyl-carbamoyl]phenyl-carbamoyl} ethyl)piperidin-4-yl ester. MS m/z: [M + H$^+$] calcd for $C_{34}H_{41}N_5O_4$, 584.33; found, 584.2. | —C(O)NH— | methylaminomethyl-cyclopropyl |
| 9-2 | Biphenyl-2-ylcarbamic acid 1-(2-{3-[3-(cyclopropyl-methylamino)propionyl-amino]phenylcarbamoyl} ethyl)piperidin-4-yl ester. MS m/z: [M + H$^+$] calcd for $C_{34}H_{41}N_5O_4$, 584.33; found, 584.2. | —NHC(O)— | methylaminomethyl-cyclopropyl |
| 9-3 | Biphenyl-2-ylcarbamic acid 1-[2-(3-{2-[(1H-imidazol-2-ylmethyl)amino]ethyl-carbamoyl}phenyl-carbamoyl) ethyl]piperidin-4-yl ester. MS m/z: [M + H$^+$] calcd for $C_{34}H_{39}N_7O_4$, 610.32; found 610.4. | —C(O)NH— | methylamino-(1H-imidazol-2-ylmethyl) |
| 9-4 | Biphenyl-2-ylcarbamic acid 1-[2-(3-{3-[(1H-imidazol-2-ylmethyl)amino]propionyl-amino}phenylcarbamoyl) ethyl]piperidin-4-yl ester. MS m/z: [M + H$^+$] calcd for $C_{34}H_{39}N_7O_4$, 610.32; found 610.2. | —NHC(O)— | methylamino-(1H-imidazol-2-ylmethyl) |
| 9-5 | Biphenyl-2-ylcarbamic acid 1-[2-(3-{2-[(furan-2-yl-methyl)amino]ethyl-carbamoyl}phenyl-carbamoyl)ethyl]piperidin-4-yl ester. MS m/z: [M + H$^+$] calcd for $C_{35}H_{39}N_5O_5$, 610.31; found 610.2. | —C(O)NH— | methylamino-(furan-2-ylmethyl) |
| 9-6 | Biphenyl-2-ylcarbamic acid 1-[2-(3-{3-[(furan-2-yl-methyl)amino] propionyl-amino}phenylcarbamoyl) ethyl]piperidin-4-yl ester. MS m/z: [M + H$^+$] calcd for $C_{35}H_{39}N_5O_5$, 610.31; found 610.2. | —NHC(O)— | methylamino-(furan-2-ylmethyl) |

Example 10

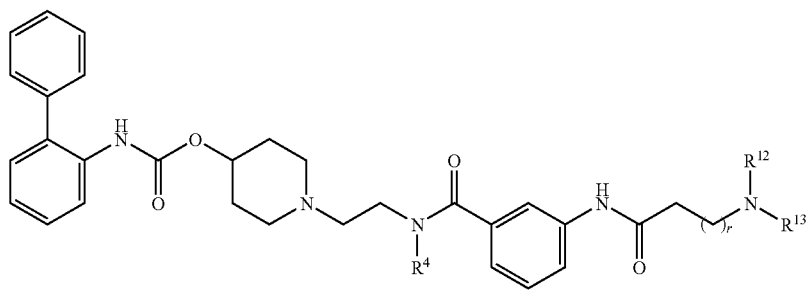

Following the procedures described in the previous examples, and substituting the appropriate starting materials and reagents, the following compounds were prepared.

| # | Name | $R^4$ | r | $-N(R^{12})(R^{13})$ |
|---|---|---|---|---|
| 10-1 | Biphenyl-2-ylcarbamic acid 1-(2-{[3-(3-cyclopropylamino-propionylamino)benzoyl]methylamino}ethyl)piperidin-4-yl ester. MS m/z: [M + H$^+$] calcd for $C_{34}H_{41}N_5O_4$, 584.33; found, 584.2. | Me | 1 | —NH-cyclopropyl |
| 10-2 | Biphenyl-2-ylcarbamic acid 1-{2-[3-(3-cyclopropylamino-propionylamino)benzoyl-amino]ethyl}piperidin-4-yl ester. MS m/z: [M + H$^+$] calcd for $C_{33}H_{39}N_5O_4$, 570.31; found, 570.2. | H | 1 | —NH-cyclopropyl |
| 10-3 | Biphenyl-2-ylcarbamic acid 1-(2-{methyl-[3-(3-methylamino-propionylamino)benzoyl]amino}ethyl)piperidin-4-yl ester. MS m/z: [M +H$^+$] calcd for $C_{32}H_{39}N_5O_4$, 578.31; found, 558.2. | Me | 1 | —NH(CH$_3$) |
| 10-4 | Biphenyl-2-ylcarbamic acid 1-{2-[3-(3-methylaminopro-pionylamino)benzoylamino]ethyl}piperidin-4-yl ester. MS m/z: [M + H$^+$] calcd for $C_{31}H_{37}N_5O_4$, 544.29; found, 544.2. | H | 1 | —NH(CH$_3$) |
| 10-5 | Biphenyl-2-ylcarbamic acid 1-(2-{3-[2-(2-hydroxyethyl-amino)acetylamino]benzoyl-amino}ethyl)piperidin-4-yl ester. MS m/z: [M + H$^+$] calcd for $C_{31}H_{37}N_5O_5$, 560.29; found, 560.2. | H | 0 | —NH-CH$_2$CH$_2$OH |
| 10-6 | Biphenyl-2-ylcarbamic acid 1-(2-{3-[2-(carbamoylmethyl-amino)acetylamino]benzoyl-amino}ethyl)piperidin-4-yl ester. MS m/z: [M + H$^+$] calcd for $C_{31}H_{36}N_6O_5$, 573.28; found, 573.2. | H | 0 | —NH-CH$_2$-C(O)NH$_2$ |
| 10-7 | Biphenyl-2-ylcarbamic acid 1-[2-(methyl-{3-[2-(3-oxo-piperazin-1-yl)acetylamino]benzoyl}amino)ethyl] piperidin-4-yl ester. MS m/z: [M + H$^+$] calcd for $C_{34}H_{40}N_6O_5$, 613.32; found, 613.2. | Me | 0 | 3-oxopiperazin-1-yl |
| 10-8 | Biphenyl-2-ylcarbamic acid 1-[2-({3-[2-(cyclopropylmethyl-amino)acetylamino]benzoyl}methylamino)ethyl]piperidin-4-yl ester. MS m/z: [M + H$^+$] calcd for $C_{34}H_{41}N_5O_4$, 584.33; found, 584.3. | Me | 0 | —NH-CH$_2$-cyclopropyl |
| 10-9 | Biphenyl-2-ylcarbamic acid 1-(2-{methyl-[3-(2-methylamino-acetylamino)benzoyl]amino}ethyl)piperidin-4-yl ester. MS m/z: [M + H$^+$] calcd for $C_{31}H_{37}N_5O_4$, 544.29; found, 544.2. | Me | 0 | —NH(CH$_3$) |
| 10-10 | Biphenyl-2-ylcarbamic acid 1-(2-{[3-(2-ethylaminoacetyl-amino)benzoyl]methylamino}ethyl) piperidin-4-yl ester. MS m/z: [M + H$^+$] calcd for $C_{32}H_{39}N_5O_4$, 558.31; found, 558.2. | Me | 0 | —NH—(CH$_2$CH$_3$) |
| 10-11 | Biphenyl-2-ylcarbamic acid 1-(2-{[3-(2-cyclopropylamino-acetylamino)benzoyl]methyl-amino}ethyl)piperidin-4-yl ester. MS m/z: [M + H$^+$] calcd for $C_{33}H_{39}N_5O_4$, 570.31; found, 570.2. | Me | 0 | —NH-cyclopropyl |
| 10-12 | Biphenyl-2-ylcarbamic acid 1-[2-({3-[2-(2-hydroxyethyl-amino)acetylamino]benzoyl}methylamino)ethyl]piperidin-4-yl ester. MS m/z: [M + H$^+$] calcd for $C_{32}H_{39}N_5O_5$, 574.31; found, 574.2. | Me | 0 | —NH-CH$_2$CH$_2$OH |
| 10-13 | Biphenyl-2-ylcarbamic acid 1-(2-{3-[2-(cyclopropylmethyl-amino)acetylamino]benzoyl amino}ethyl)piperidin-4-yl ester. MS m/z: [M + H$^+$]calcd for $C_{33}H_{39}N_5O_4$, 570.31; found, 570.2. | H | 0 | —NH-CH$_2$-cyclopropyl |
| 10-14 | Biphenyl-2-ylcarbamic acid 1-[2-({3-[2-(cyclopropylmethyl-amino)ethylcarbamoyl]benzoyl}methylamino)ethyl] piperidin-4-yl ester. MS m/z: [M + H$^+$]calcd for $C_{35}H_{43}N_5O_4$, 598.34; found 598.4. | Me | 1 | —NH-CH$_2$-cyclopropyl |
| 10-15 | Biphenyl-2-ylcarbamic acid 1-{2-[3-(2-methylaminoacetyl-amino)benzoylamino]ethyl} piperidin-4-yl ester. MS m/z: [M + H$^+$] calcd for $C_{30}H_{35}N_5O_4$, 530.28; found, 530.2. | H | 0 | —NH(CH$_3$) |
| 10-16 | Biphenyl-2-ylcarbamic acid 1-{2-[3-(2-ethylaminoacetyl-amino)benzoylamino]ethyl} piperidin-4-yl ester. MS m/z: [M + H$^+$] calcd for $C_{31}H_{37}N_5O_4$, 544.29; found, 544.2. | H | 0 | —NH—(CH$_2$CH$_3$) |
| 10-17 | Biphenyl-2-ylcarbamic acid 1-{2-[3-(2-cyclopropylamino-acetylamino)benzoylamino]ethyl}piperidin-4-yl ester. MS m/z: [M + H$^+$] calcd for $C_{32}H_{37}N_5O_4$, 556.29; found, 558.2. | H | 0 | —NH-cyclopropyl |

Preparation 9

N-(2,2-Dimethoxyethyl)isophthalamic Acid Methyl Ester

Mono-methyl isophthalate (1 g, 5.55 mmol), amino acetaldehyde dimethyl acetal (569 μL, 5.28 mmol) and EDCI (1.52 g, 7.92 mmol) were dissolved in 55 mL DCM, followed by the addition of DIPEA (1.84 mL, 10.56 mmol). The reaction was allowed to stir at room temperature for 2 hours. It was then taken up in 50 mL of DCM, washed with saturated NaHCO₃ solution (100 mL), and brine (100 mL). The organic layer was dried over MgSO₄, filtered and concentrated to afford the crude product (1.48 g) as a clear oil which was used in the next step without further purification.

Preparation 10

N-(2,2-Dimethoxyethyl)isophthalamic Acid 1.48 g of the product of Preparation 9 was dissolved in DMF (5 mL), and NaOH (2.8 ml, of 10 N solution, 27.75 mmol) was added. The reaction was stirred at room temperature overnight. It was then adjusted to pH 5 using 1.0 N HCl and extracted with EtOAc 3×50 mL and DCM 3×50 mL. The organic phases were combined, dried over MgSO4 and concentrated to afford 0.55 g crude product as an off-white solid which was used in the next step without further purification.

Preparation 11

Biphenyl-2-ylcarbamic Acid 1-(2-{-[3-(2,2-Dimethoxyethylcarbamoyl)benzoyl]methylamino}ethyl)piperidin-4-yl Ester To a solution of the product of Preparation 10 (0.55 g, 2.2 mmol) and biphenyl-2-ylcarbamic acid 1-(2-methylaminoethyl)piperidin-4-yl ester (0.77 g, 2.2 mmol; prepared as described in Preparation 6) in 12 mL of DCM was added EDCI (0.55 g, 2.86 mmol) followed by 0.77 mL of DIPEA (4.4 mmol, 2 eq). After stirring at room temperature for 3 hours, the reaction was taken up in 100 mL DCM. The mixture was then washed with 100 mL of a 1:1 solution of 1.0 N HCl in brine, then washed with brine 100 mL. The organic phase was then dried over MgSO₄, filtered and concentrated. The crude product was obtained as a white solid (0.86 g, 68%).

Preparation 12

Biphenyl-2-ylcarbamic Acid 1-(2-{Methyl-[3-(2-oxoethylcarbamoyl)benzoyl]amino}ethyl)piperidin-4-yl Ester To a solution of the product of Preparation 11 (0.86 g, 1.46 mmol) in 25 mL of acetone was added 3 mL of 1 N HCl. The reaction was stirred at room temperature overnight before it was concentrated under reduced pressure. The residual aqueous solution was lyophilized to give 0.8 g of crude product as an off-white solid.

Example 11

Biphenyl-2-ylcarbamic Acid 1-(2-{Methyl-[3-(2-methylaminoethylcarbamoyl)benzoyl]amino}ethyl)piperidin-4-yl Ester

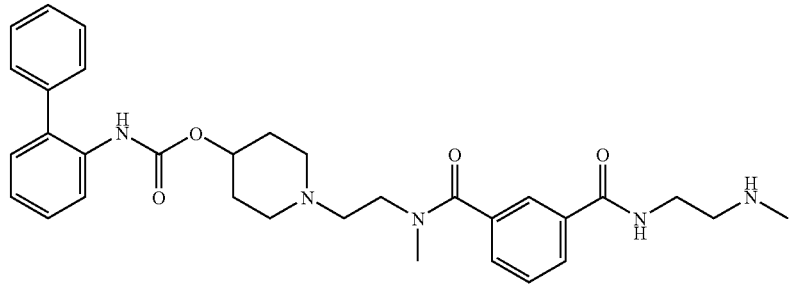

A solution of the product of Preparation 12 (56 mg, 0.1 mmol) and methyl amine (1M in THF, 0.2 mL, 0.2 mmol) in 1 mL of MeOH was stirred at room temperature for 1 hour before Na(OAc)₃BH (60 mg, 0.3 mmol) was added to the reaction. The mixture was allowed to stir for an additional hour and was concentrated under reduced pressure. The residue was dissolved in 1.5 mL of a 1:1 HOAc/H₂O mixture, and was purified by reversed-phase HPLC to afford the title compound as a bis(trifluoroacetate) salt. MS m/z: [M+H⁺] calcd for $C_{32}H_{39}N_5O_4$, 558.31; found, 558.2.

Example 12

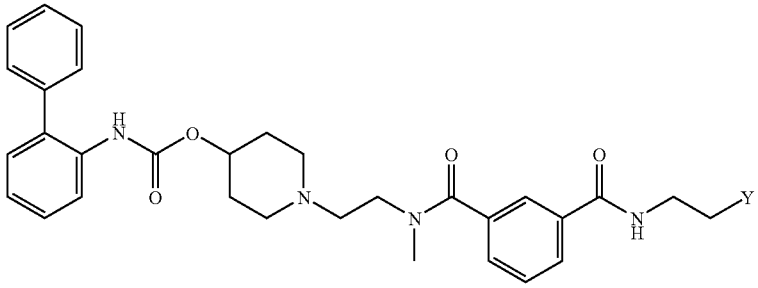

Following the procedure described in Example 11 and substituting the appropriate amine in place of methyl amine, the following compounds were prepared.

| # | Name | Y |
|---|------|---|
| 12-1 | Biphenyl-2-ylcarbamic acid 1-[2-({3-[2-(2-hydroxyethylamino)ethyl-carbamoyl]benzoyl}methylamino)ethyl]piperidin-4-yl ester. MS m/z: [M + H$^+$] calcd for C$_{33}$H$_{41}$N$_5$O$_5$, 588.32; found, 588.2. | —NH(CH$_2$CH$_2$OH) |
| 12-2 | Biphenyl-2-ylcarbamic acid 1-{2-[(3-{2-[2-(4-hydroxy-phenyl)ethylamino]ethyl-carbamoyl}benzoyl)methylamino]ethyl} piperidin-4-yl ester. MS m/z: [M + H$^+$] calcd for C$_{39}$H$_{45}$N$_5$O$_5$, 664.35; found, 664.4. | ![structure: —NH-CH2CH2-C6H4-OH] |

Example 13

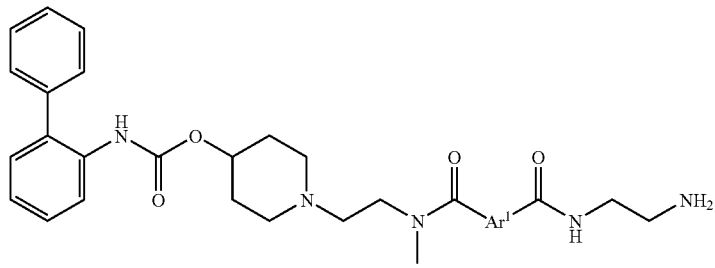

Compound 13-6 was prepared as follows. A solution of terephthalic acid (33 mg, 0.2 mmol), HATU (228 mg, 0.6 mmol) and DIPEA (0.1 mL, 0.6 mmol) in DMF (0.5 mL) was stirred at room temperature for 0.5 hours. Biphenyl-2-ylcarbamic acid 1-(2-methylaminoethyl)piperidin-4-yl ester (70.7 mg, 0.2 mmol; prepared as described in Preparation 6) and t-butyl n-(2-aminoethyl) carbamate (32 mg, 0.2 mmol) were added to the reaction sequentially in one hour interval. The mixture was then stirred at room temperature for an additional 1 hour. Solvent was removed under reduced pressure. The residue was purified by HPLC to give the titled compound as a bis(trifluoroacetate) salt.

Following the procedure described above and substituting the appropriate aromatic diacid, compounds 13-1 to 13-5 were also prepared.

| # | Name | Ar$^1$ |
|---|------|--------|
| 13-1 | Biphenyl-2-ylcarbamic acid 1-(2-{[6-(2-amino ethylcarbamoyl)pyridine-2-carbonyl]methyl amino}ethyl)piperidin-4-yl ester. MS m/z: [M + H$^+$] calcd for C$_{30}$H$_{36}$N$_6$O$_4$, 545.28; found 545.2. | 2,6-pyridyl |
| 13-2 | Biphenyl-2-ylcarbamic acid 1-(2-{[5-(2-amino ethylcarbamoyl)pyridine-3-carbonyl]methyl amino}ethyl)piperidin-4-yl ester. MS m/z: [M + H$^+$] calcd for C$_{30}$H$_{36}$N$_6$O$_4$, 545.28; found 545.2. | 3,5-pyridyl |
| 13-3 | Biphenyl-2-ylcarbamic acid 1-(2-{[6-(2-amino ethylcarbamoyl)pyridine-3-carbonyl]methyl amino}ethyl)piperidin-4-yl ester. MS m/z: [M + H$^+$] calcd for C$_{30}$H$_{36}$N$_6$O$_4$, 545.28; found 545.2. | 2,5-pyridyl |
| 13-4 | Biphenyl-2-ylcarbamic acid 1-(2-{[5-(2-amino ethylcarbamoyl)thiophene-2-carbonyl]methyl amino}ethyl)piperidin-4-yl ester. MS m/z: [M + H$^+$] calcd for C$_{29}$H$_{35}$N$_5$O$_4$S, 550.24; found 550.2. | 2,5-thiophene |

-continued

| # | Name | Ar$^1$ |
|---|------|--------|
| 13-5 | Biphenyl-2-ylcarbamic acid 1-(2-{[5-(2-amino ethylcarbamoyl)furan-2-carbonyl]methyl amino}ethyl)piperidin-4-yl ester. MS m/z: [M + H$^+$] calcd for C$_{29}$H$_{35}$N$_5$O$_5$, 534.26; found 534.2. | 2,5-furan |
| 13-6 | Biphenyl-2-ylcarbamic acid 1-(2-{[4-(2-aminoethylcarbamoyl)benzoyl]methylamino}ethyl)piperidin-4-yl ester. MS m/z: [M + H$^+$] calcd for C$_{31}$H$_{37}$N$_5$O$_4$, 544.28; found 544.2. | 1,4-phenyl |

Example 14

Biphenyl-2-ylcarbamic Acid 1-{2-[3-(2-Aminoethylcarbamoyl)benzoylamino]ethyl}piperidin-4-yl Ester

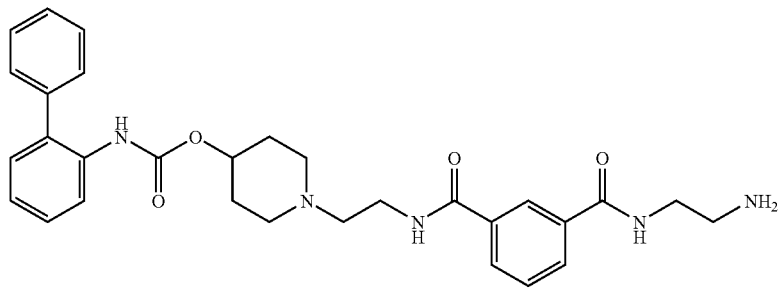

The title compound was prepared following a similar procedure as described in Example 13, by substituting the appropriate biphenyl-2-ylcarbamic acid 1-(aminoethyl)piperidin-4-yl ester in place of biphenyl-2-ylcarbamic acid 1-(2-methylaminoethyl)piperidin-4-yl ester and substituting isophthalic acid in place of terephthalic acid.

MS m/z: [M+H$^+$] calcd for $C_{30}H_{35}N_5O_4$, 530.27; found 530.3.

Example 15

Biphenyl-2-ylcarbamic Acid 1-(2-{[5-(3-Aminopropylcarbamoyl)thiophene-2-carbonyl]methylamino}ethyl)piperidin-4-yl Ester

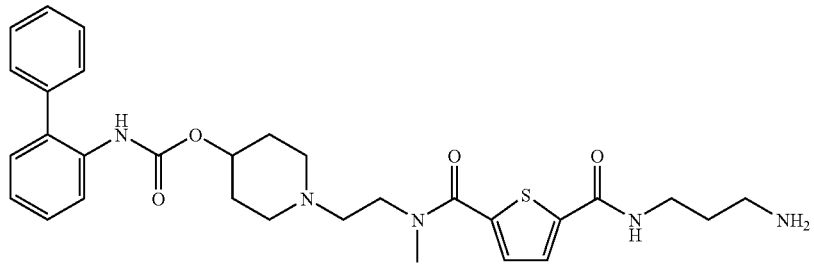

The title compound was prepared following a similar procedure as described in Example 13, and substituting 2,5-thiophenedicarboxylic acid in place of terephthalic acid, and substituting t-butyl n-(3-aminopropyl) carbamate in place of t-butyl n-(2-aminoethyl) carbamate.

MS m/z: [M+H$^+$] calcd for $C_{30}H_{37}N_5O_4S$, 564.26; found 564.2.

Assay 1

Radioligand Binding Assay

Membrane Preparation from Cells Expressing hM$_1$, hM$_2$, hM$_3$ and hM$_4$ Muscarinic Receptor Subtypes CHO cell lines stably expressing cloned human hM$_1$, hM$_2$, hM$_3$ and hM$_4$ muscarinic receptor subtypes, respectively, were grown to near confluency in medium consisting of HAM's F-12 supplemented with 10% FBS and 250 µg/mL Geneticin. The cells were grown in a 5% $CO_2$, 37° C. incubator and lifted with 2 mM EDTA in dPBS. Cells were collected by 5 minute centrifugation at 650×g, and cell pellets were either stored frozen at −80° C. or membranes were prepared immediately. For membrane preparation, cell pellets were resuspended in lysis buffer and homogenized with a Polytron PT-2100 tissue disrupter (Kinematica AG; 20 seconds×2 bursts). Crude membranes were centrifuged at 40,000×g for 15 minutes at 4° C. The membrane pellet was then resuspended with resuspension buffer and homogenized again with the Polytron tissue disrupter. The protein concentration of the membrane suspension was determined by the method described in Lowry, O. et al., *Journal of Biochemistry* 193:265 (1951). All membranes were stored frozen in aliquots at −80° C. or used immediately. Aliquots of prepared hM$_5$ receptor membranes were purchased directly from Perkin Elmer and stored at −80° C. until use.

Radioligand Binding Assay on Muscarinic Receptor Subtypes hM$_1$, hM$_2$, hM$_3$, hM$_4$ and hM$_5$ Radioligand binding assays were performed in 96-well microtiter plates in a total assay volume of 100 µL. CHO cell membranes stably expressing either the hM$_1$, hM$_2$, hM$_3$, hM$_4$ or hM$_5$ muscarinic subtype were diluted in assay buffer to the following specific target protein concentrations (µg/well): 10 µg for hM$_1$, 10-15 µg for hM$_2$, 10-20 µg for hM$_3$, 10-20 µg for hM$_4$, and 10-12 µg for hM$_5$. The membranes were briefly homogenized using a Polytron tissue disrupter (10 seconds) prior to assay plate addition. Saturation binding studies for determining K$_D$ values of the radioligand were performed using L-[N-methyl-3H]scopolamine methyl chloride ([$^3$H]-NMS) (TRK666, 84.0 Ci/mmol, Amersham Pharmacia Biotech, Buckinghamshire, England) at concentrations ranging from 0.001 nM to 20 nM. Displacement assays for determination of $K_i$ values of test compounds were performed with [$^3$H]-NMS at 1 nM and eleven different test compound concentrations. The test compounds were initially dissolved to a concentration of 400 μM in dilution buffer and then serially diluted 5× with dilution buffer to final concentrations ranging from 10 μM to 100 μM. The addition order and volumes to the assay plates were as follows: 25 μL radioligand, 25 μL diluted test compound, and 50 μL membranes. Assay plates were incubated for 60 minutes at 37° C. Binding reactions were terminated by rapid filtration over GF/B glass fiber filter plates (PerkinElmer Inc., Wellesley, Mass.) pre-treated in 1% BSA. Filter plates were rinsed three times with wash buffer (10 mM HEPES) to remove unbound radioactivity. Plates were then air dried, and 50 μL Microscint-20 liquid scintillation fluid (PerkinElmer Inc., Wellesley, Mass.) was added to each well. The plates were then counted in a PerkinElmer Topcount liquid scintillation counter (PerkinElmer Inc., Wellesley, Mass.). Binding data were analyzed by nonlinear regression analysis with the GraphPad Prism Software package (GraphPad Software, Inc., San Diego, Calif.) using the one-site competition model. $K_i$ values for test compounds were calculated from observed $IC_{50}$ values and the $K_D$ value of the radioligand using the Cheng-Prusoff equation (Cheng Y; Prusoff W. H. *Biochemical Pharmacology* 22(23):3099-108 (1973)). $K_i$ values were converted to $pK_i$ values to determine the geometric mean and 95% confidence intervals. These summary statistics were then converted back to $K_i$ values for data reporting.

In this assay, a lower $K_i$ value indicates that the test compound has a higher binding affinity for the receptor tested. For example, the compound of Example 1 was found to have a $K_i$ value of less than about 5 nM for the $M_3$ muscarinic receptor subtype when tested in this or a similar assay.

Assay 2

Muscarinic Receptor Functional Potency Assays

Blockade of Agonist-Mediated Inhibition of cAMP Accumulation

In this assay, the functional potency of a test compound is determined by measuring the ability of the test compound to block oxotremorine-inhibition of forskolin-mediated cAMP accumulation in CHO-K1 cells expressing the hM$_2$ receptor.

cAMP assays are performed in a radioimmunoassay format using the Flashplate Adenylyl Cyclase Activation Assay System with $^{125}$I-cAMP (NEN SMP004B, PerkinElmer Life Sciences Inc., Boston, Mass.), according to the manufacturer's instructions.

Cells are rinsed once with dPBS and lifted with Trypsin-EDTA solution (0.05% trypsin/0.53 mM EDTA) as described in the Cell Culture and Membrane Preparation section above. The detached cells are washed twice by centrifugation at 650×g for five minutes in 50 mLs dPBS. The cell pellet is then re-suspended in 10 mL dPBS, and the cells are counted with a Coulter Z1 Dual Particle Counter (Beckman Coulter, Fullerton, Calif.). The cells are centrifuged again at 650×g for five minutes and re-suspended in stimulation buffer to an assay concentration of 1.6×10$^6$-2.8×10$^6$ cells/mL.

The test compound is initially dissolved to a concentration of 400 μM in dilution buffer (dPBS supplemented with 1 mg/mL BSA (0.1%)), and then serially diluted with dilution buffer to final molar concentrations ranging from 100 μM to 0.1 nM. Oxotremorine is diluted in a similar manner.

To measure oxotremorine inhibition of adenylyl cyclase (AC) activity, 25 μL forskolin (25 μM final concentration diluted in dPBS), 25 μL diluted oxotremorine, and 50 μL cells are added to agonist assay wells. To measure the ability of a test compound to block oxotremorine-inhibited AC activity, 25 μL forskolin and oxotremorine (25 μM and 5 μM final concentrations, respectively, diluted in dPBS) 25 μL diluted test compound, and 50 μL cells are added to remaining assay wells.

Reactions are incubated for 10 minutes at 37° C. and stopped by addition of 100 μL ice-cold detection buffer. Plates are sealed, incubated overnight at room temperature and counted the next morning on a PerkinElmer TopCount liquid scintillation counter (PerkinElmer Inc., Wellesley, Mass.). The amount of cAMP produced (pmol/well) is calculated based on the counts observed for the samples and cAMP standards, as described in the manufacturer's user manual. Data are analyzed by nonlinear regression analysis with the GraphPad Prism Software package (GraphPad Software, Inc., San Diego, Calif.) using the non-linear regression, one-site competition equation. The Cheng-Prusoff equation is used to calculate the $K_i$, using the $EC_{50}$ of the oxotremorine concentration-response curve and the oxotremorine assay concentration as the $K_D$ and [L], respectively. The $K_i$ values are converted to $pK_i$ values to determine the geometric mean and 95% confidence intervals. These summary statistics are then converted back to Ic values for data reporting.

In this assay, a lower $K_i$ value indicates that the test compound has a higher functional activity at the receptor tested. Compounds of the invention are expected to have a $K_i$ value of less than about 10 nM for blockade of oxotremorine-inhibition of forskolin-mediated cAMP accumulation in CHO-K1 cells expressing the hM$_2$ receptor, when tested in this or a similar assay.

Blockade of Agonist-Mediated [$^{35}$S]GTPγS Binding

In a second functional assay, the functional potency of test compounds can be determined by measuring the ability of the compounds to block oxotremorine-stimulated [$^{35}$S] GTPγS binding in CHO-K1 cells expressing the hM$_2$ receptor.

At the time of use, frozen membranes are thawed and then diluted in assay buffer with a final target tissue concentration of 5-10 μg protein per well. The membranes are briefly homogenized using a Polytron PT-2100 tissue disrupter and then added to the assay plates.

The $EC_{90}$ value (effective concentration for 90% maximal response) for stimulation of [$^{35}$S]GTPγS binding by the agonist oxotremorine is determined in each experiment.

To determine the ability of a test compound to inhibit oxotremorine-stimulated [$^{35}$S]GTPγS binding, the following is added to each well of 96 well plates: 25 μL of assay buffer with [$^{35}$S]GTPγS (0.4 nM), 25 μL, of oxotremorine($EC_{90}$) and GDP (3 μM), 25 μL, of diluted test compound and 25 μL, CHO cell membranes expressing the hM$_2$ receptor. The assay plates are then incubated at 37° C. for 60 minutes. The assay plates are filtered over 1% BSA-pretreated GF/B filters using a PerkinElmer 96-well harvester. The plates are rinsed with ice-cold wash buffer for 3×3 seconds and then air or vacuum dried. Microscint-20 scintillation liquid (50 μL) is added to each well, and each plate is sealed and radioactivity counted on a topcounter (PerkinElmer). Data are analyzed by nonlinear regression analysis with the GraphPad Prism Software package (GraphPad Software, Inc., San Diego, Calif.) using the non-linear regression, one-site competition equation. The Cheng-Prusoff equation is used to calculate the using the $IC_{50}$ values of the concentration-response curve for the test compound and the oxotremorine concentration in the assay as the $K_D$ and [L], ligand concentration, respectively.

In this assay, a lower $K_i$ value indicates that the test compound has a higher functional activity at the receptor tested. Compounds of the invention are expected to have a $K_i$ value of less than about 10 nM for blockade of oxotremorine-stimulated [$^{35}$S]GTPγS binding in CHO-K1 cells expressing the hM$_2$ receptor, when tested in this or a similar assay.

Blockade of Agonist-Mediated Calcium Release via FLIPR Assays

Muscarinic receptor subtypes (M$_1$, M$_3$ and M$_5$ receptors), which couple to G$_q$ proteins, activate the phospholipase C (PLC) pathway upon agonist binding to the receptor. As a result, activated PLC hydrolyzes phosphatyl inositol diphosphate (PIP$_2$) to diacylglycerol (DAG) and phosphatidyl-1,4,5-triphosphate (IP$_3$), which in turn generates calcium release from intracellular stores, i.e., endoplasmic and sarcoplasmic reticulum. The FLIPR (Molecular Devices, Sunnyvale, Calif.) assay capitalizes on this increase in intracellular calcium by using a calcium sensitive dye (Fluo-4AM, Molecular Probes, Eugene, Oreg.) that fluoresces when free calcium binds. This fluorescence event is measured in real time by the FLIPR, which detects the change in fluorescence from a monolayer of cells cloned with human M$_1$ and M$_3$, and chimpanzee M$_5$ receptors. Antagonist potency can be determined by the ability of antagonists to inhibit agonist-mediated increases in intracellular calcium.

For FLIPR calcium stimulation assays, CHO cells stably expressing the hM$_1$, hM$_3$ and cM$_5$ receptors are seeded into 96-well FLIPR plates the night before the assay is done. Seeded cells are washed twice by Cellwash (MTX Labsystems, Inc.) with FLIPR buffer (10 mM HEPES, pH 7.4, 2 mM calcium chloride, 2.5 mM probenecid in Hank's Buffered Salt Solution (HBSS) without calcium and magnesium) to remove growth media and leaving 50 μL/well of FLIPR buffer. The cells are then incubated with 50 μL/well of 4 μM FLUO-4AM (a 2× solution was made) for 40 minutes at 37° C., 5% carbon dioxide. Following the dye incubation period, cells are washed two times with FLIPR buffer, leaving a final volume of 50 μL/well.

To determine antagonist potency, the dose-dependent stimulation of intracellular Ca$^{2+}$ release for oxotremorine is first determined so that antagonist potency can later be measured against oxotremorine stimulation at an EC$_{90}$ concentration. Cells are first incubated with compound dilution buffer for 20 minutes, followed by agonist addition, which is performed by the FLIPR. An EC$_{90}$ value for oxotremorine is generated according to the method detailed in the FLIPR measurement and data reduction section below, in conjunction with the formula EC$_F$=((F/100-F)^1/H)*EC$_{50}$. An oxotremorine concentration of 3×EC$_F$ is prepared in stimulation plates such that an EC$_{90}$ concentration of oxotremorine is added to each well in the antagonist inhibition assay plates.

The parameters used for the FLIPR are: exposure length of 0.4 seconds, laser strength of 0.5 watts, excitation wavelength of 488 nm, and emission wavelength of 550 nm. Baseline is determined by measuring the change in fluorescence for 10 seconds prior to addition of agonist. Following agonist stimulation, the FLIPR continuously measured the change of fluorescence every 0.5 to 1 second for 1.5 minutes to capture the maximum fluorescence change. The change of fluorescence is expressed as maximum fluorescence minus baseline fluorescence for each well. The raw data is analyzed against the logarithm of drug concentration by nonlinear regression with GraphPad Prism (GraphPad Software, Inc., San Diego, Calif.) using the built-in model for sigmoidal dose-response.

Antagonist $K_i$ values are determined by Prism using the oxotremorine EC$_{50}$ value as the K$_D$ and the oxotremorine EC$_{90}$ for the ligand concentration according to the Cheng-Prusoff equation (Cheng & Prusoff, 1973).

In this assay, a lower $K_i$ value indicates that the test compound has a higher functional activity at the receptor tested. Compounds of the invention are expected to have a $K_i$ value of less than about 10 nM for blockade of agonist-mediated calcium release in CHO cells stably expressing the hM$_3$ receptor, when tested in this or a similar assay.

Assay 3

Determination of Duration of Bronchoprotection in Guinea Pig Model of Acetylcholine-Induced Bronchoconstriction This in vivo assay is used to assess the bronchoprotective effects of test compounds exhibiting muscarinic receptor antagonist activity. Groups of six male guinea pigs (Duncan-Hartley (HsdPoc:DH) Harlan, Madison, Wis.) weighing between 250 and 350 g are individually identified by cage cards. Throughout the study animals are allowed access to food and water ad libitum.

Test compounds are administered via inhalation over 10 minutes in a whole-body exposure dosing chamber (R&S Molds, San Carlos, Calif.). The dosing chambers are arranged so that an aerosol was simultaneously delivered to 6 individual chambers from a central manifold. Guinea pigs are exposed to an aerosol of a test compound or vehicle (WFI). These aerosols are generated from aqueous solutions using an LC Star Nebulizer Set (Model 22F51, PARI Respiratory Equipment, Inc. Midlothian, Va.) driven by a mixture of gases (CO$_2$=5%, O$_2$=21% and N$_2$=74%) at a pressure of 22 psi. The gas flow through the nebulizer at this operating pressure is approximately 3 L/minute. The generated aerosols are driven into the chambers by positive pressure. No dilution air is used during the delivery of aerosolized solutions. During the 10 minute nebulization, approximately 1.8 mL of solution is nebulized. This is measured gravimetrically by comparing pre- and post-nebulization weights of the filled nebulizer.

The bronchoprotective effects of test compounds administered via inhalation are evaluated using whole body plethysmography at 1.5, 24, 48 and 72 hours post-dose. Forty-five minutes prior to the start of the pulmonary evaluation, each guinea pig is anesthetized with an intramuscular injection of ketamine (43.75 mg/kg), xylazine (3.50 mg/kg) and acepromazine (1.05 mg/kg). After the surgical site is shaved and cleaned with 70% alcohol, a 2-3 cm midline incision of the ventral aspect of the neck was made. Then, the jugular vein is isolated and cannulated with a saline-filled polyethylene catheter (PE-50, Becton Dickinson, Sparks, Md.) to allow for intravenous infusions of ACh (Sigma-Aldrich, St. Louis, Mo.) in saline. The trachea is then dissected free and cannulated with a 14G teflon tube (#NE-014, Small Parts, Miami Lakes, Fla.). If required, anesthesia is maintained by additional intramuscular injections of the aforementioned anesthetic mixture. The depth of anesthesia is monitored and adjusted if the animal responds to pinching of its paw or if the respiration rate is greater than 100 breaths/minute.

Once the cannulations are complete, the animal is placed into a plethysmograph (#PLY3114, Buxco Electronics, Inc., Sharon, Conn.) and an esophageal pressure cannula (PE-160, Becton Dickinson, Sparks, Md.) is inserted to measure pulmonary driving pressure (pressure). The teflon tracheal tube is attached to the opening of the plethysmograph to allow the guinea pig to breathe room air from outside the chamber. The chamber is then sealed. A heating lamp is used to maintain body temperature and the guinea pig's lungs are inflated 3 times with 4 mL of air using a 10 mL calibration syringe (#5520 Series, Hans Rudolph, Kansas City, Mo.) to ensure that the lower airways do not collapse and that the animal does not suffer from hyperventilation.

Once it is determined that baseline values are within the range 0.3-0.9 mL/cm $H_2O$ for compliance and within the range 0.1-0.199 cm $H_2O$/mL per second for resistance, the pulmonary evaluation is initiated. A Buxco pulmonary measurement computer program enables the collection and derivation of pulmonary values.

Starting this program initiates the experimental protocol and data collection. The changes in volume over time that occur within the plethysmograph with each breath are measured via a Buxco pressure transducer. By integrating this signal over time, a measurement of flow is calculated for each breath. This signal, together with the pulmonary driving pressure changes, which are collected using a Sensym pressure transducer (#TRD4100), is connected via a Buxco (MAX 2270) preamplifier to a data collection interface (#'s SFT3400 and SFT3813). All other pulmonary parameters are derived from these two inputs.

Baseline values are collected for 5 minutes, after which time the guinea pigs are challenged with ACh. ACh (0.1 mg/mL) is infused intravenously for 1 minute from a syringe pump (sp210iw, World Precision Instruments, Inc., Sarasota, Fla.) at the following doses and prescribed times from the start of the experiment: 1.9 µg/minute at 5 minutes, 3.8 µg/minute at 10 minutes, 7.5 µg/minute at 15 minutes, 15.0 µg/minute at 20 minutes, 30 µg/minute at 25 minutes and 60 µg/minute at 30 minutes. If resistance or compliance has not returned to baseline values at 3 minutes following each ACh dose, the guinea pig's lungs are inflated 3 times with 4 mL of air from a 10 mL calibration syringe. Recorded pulmonary parameters includes respiration frequency (breaths/minute), compliance (mL/cm $H_2O$) and pulmonary resistance (cm $H_2O$/mL per second). Once the pulmonary function measurements are completed at minute 35 of this protocol, the guinea pig is removed from the plethysmograph and euthanized by carbon dioxide asphyxiation.

The data are evaluated in one or both of the following ways:

(a) Pulmonary resistance ($R_L$, cm $H_2O$/mL per second) is calculated from the ratio of "change in pressure" to "the change in flow." The $R_L$ response to ACh (60 µg/min, 1H) is computed for the vehicle and the test compound groups. The mean ACh response in vehicle-treated animals, at each pre-treatment time, is calculated and used to compute % inhibition of ACh response, at the corresponding pre-treatment time, at each test compound dose. Inhibition dose-response curves for '$R_L$' are fitted with a four parameter logistic equation using GraphPad Prism, version 3.00 for Windows (GraphPad Software, San Diego, Calif.) to estimate bronchoprotective $ID_{50}$ (dose required to inhibit the ACh (60 µg/min) bronchoconstrictor response by 50%). The equation used is as follows:

$$Y = Min + (Max - Min)/(1 + 10^{((log ID50 - X) * Hillslope)})$$

where X is the logarithm of dose, Y is the response (% Inhibition of ACh induced increase in $R_L$). Y starts at Min and approaches asymptotically to Max with a sigmoidal shape.

(b) The quantity $PD_2$, which is defined as the amount of ACh or histamine needed to cause a doubling of the baseline pulmonary resistance, is calculated using the pulmonary resistance values derived from the flow and the pressure over a range of ACh or histamine challenges using the following equation (which is derived from a equation used to calculate $PC_{20}$ values described in American Thoracic Society. Guidelines for methacholine and exercise challenge testing—1999. *Am J Respir Crit. Care Med.* 161:309-329 (2000)):

$$PD_2 = \text{antilog}\left[\log C_1 + \frac{(\log C_2 - \log C_1)(2R_0 - R_1)}{R_2 - R_1}\right]$$

where: $C_1$ is the concentration of ACh or histamine preceding $C_2$; $C_2$ is the concentration of ACh or histamine resulting in at least a 2-fold increase in pulmonary resistance ($R_L$); $R_0$ is the baseline $R_L$ value; $R_1$ is the $R_L$ value after $C_1$; and $R_2$ is the $R_L$ value after $C_2$. An efficacious dose is defined as a dose that limits the bronchrestriction response to a 50 µg/mL dose of ACh to a doubling of the baseline pulmonary resistance ($PD_{2(50)}$).

Statistical analysis of the data is performed using a two-tailed Students t-test. A P-value <0.05 is considered significant. Generally, test compounds having a $PD_{2(50)}$ less than about 200 µg/mL for ACh-induced bronchoconstriction at 1.5 hours post-dose in this assay are preferred. Compounds of the invention are expected to have a $PD_{2(50)}$ of less than about 200 µg/mL for ACh-induced bronchoconstriction at 1.5 hours post-dose, when tested in this or a similar assay.

Assay 4

Inhalation Guinea Pig Salivation Assay

Guinea pigs (Charles River, Wilmington, Mass.) weighing 200-350 g are acclimated to the in-house guinea pig colony for at least 3 days following arrival. Test compound or vehicle are dosed via inhalation (IH) over a 10 minute time period in a pie shaped dosing chamber (R&S Molds, San Carlos, Calif.). Test solutions are dissolved in sterile water and delivered using a nebulizer filled with 5.0 mL of dosing solution. Guinea pigs are restrained in the inhalation chamber for 30 minutes. During this time, guinea pigs are restricted to an area of approximately 110 sq. cm. This space is adequate for the animals to turn freely, reposition themselves, and allow for grooming. Following 20 minutes of acclimation, guinea pigs are exposed to an aerosol generated from a LS Star Nebulizer Set (Model 22F51, PARI Respiratory Equipment, Inc. Midlothian, Va.) driven by house air at a pressure of 22 psi. Upon completion of nebulization, guinea pigs are evaluated at 1.5, 6, 12, 24, 48, or 72 hrs after treatment. Guinea pigs are anesthetized one hour before testing with an intramuscular (IM) injection of a mixture of ketamine 43.75 mg/kg, xylazine 3.5 mg/kg, and acepromazine 1.05 mg/kg at an 0.88 mL/kg volume. Animals are placed ventral side up on a heated (37° C.) blanket at a 20 degree incline with their head in a downward slope. A 4-ply 2×2 inch gauze pad (Nu-Gauze General-use sponges, Johnson and Johnson, Arlington, Tex.) is inserted in the guinea pig's mouth. Five minutes later, the muscarinic agonist pilocarpine (3.0 mg/kg, SC) is administered and the gauze pad is immediately discarded and replaced by a new pre-weighed gauze pad. Saliva is collected for 10 minutes, at which point the gauze pad is weighed and the difference in weight recorded to determine the amount of accumulated saliva (in mg). The mean amount of saliva collected for animals receiving the vehicle and each dose of test compound is calculated. The vehicle group mean is considered to be 100% salivation. Results are calculated using result means (n=3 or greater). Confidence intervals (95%) are calculated for each dose at each time point using two-way ANOVA. This model is a modified version of the procedure described in Rechter, "Estimation of anticholinergic drug effects in mice by antagonism against pilocarpine-induced salivation" *Ata Pharmacol Toxicol* 24:243-254 (1996).

The mean weight of saliva in vehicle-treated animals, at each pre-treatment time, is calculated and used to compute % inhibition of salivation, at the corresponding pre-treatment time, at each dose. The inhibition dose-response data are fitted to a four parameter logistic equation using GraphPad Prism, version 3.00 for Windows (GraphPad Software, San Diego, Calif.) to estimate anti-sialagogue $ID_{50}$ (dose required to inhibit 50% of pilocarpine-evoked salivation). The following equation is used:

$$Y=\text{Min}+(\text{Max}-\text{Min})/(1+10^{((\log ID50-X)*Hillslope)})$$

where X is the logarithm of dose, Y is the response (% inhibition of salivation). Y starts at Min and approaches asymptotically to Max with a sigmoidal shape. The ratio of the anti-sialagogue $ID_{50}$ to bronchoprotective $ID_{50}$ is used to compute the apparent lung-selectivity index of the test compound. Generally, compounds having an apparent lung-selectivity index greater than about 5 are preferred. Compounds of the invention are expected to have an apparent lung-selectivity index greater than 5, when tested in this or a similar assay.

Assay 5

Methacholine-Induced Depressor Responses in Conscious Guinea Pigs

Healthy, adult, male Sprague-Dawley guinea pigs (Harlan, Indianapolis, Ind.), weighing between 200 and 300 g are used in these studies. Under isoflurane anesthesia (to effect), animals are instrumented with common carotid artery and jugular vein catheters (PE-50 tubing). The catheters are exteriorized utilizing a subcutaneous tunnel to the subscapular area. All surgical incisions are sutured with 4-0 Ethicon Silk and the catheters locked with heparin (1000 units/mL). Each animal is administered saline (3 mL, SC) at the end of surgery as well as buprenorphine (0.05 mg/kg, IM). Animals are allowed to recover on a heating pad before being returned to their holding rooms.

Approximately 18 to 20 hours following surgery, the animals are weighed and the carotid artery catheter on each animal is connected to a transducer for recording arterial pressure. Arterial pressure and heart rate are recorded using a Biopac MP-100 Acquisition System. Animals are allowed to acclimate and stabilize for a period of 20 minutes.

Each animal is challenged with MCh (0.3 mg/kg, IV) administered through the jugular venous line and the cardiovascular response is monitored for 10 minutes. The animals are then placed into the whole body dosing chamber, which is connected to a nebulizer containing the test compound or vehicle solution. The solution is nebulized for 10 minutes using a gas mixture of breathable air and 5% carbon dioxide with a flow rate of 3 liters/minute. The animals are then removed from the whole body chamber and returned to their respective cages. At 1.5 and 24 hours post-dosing, the animals are re-challenged with MCh (0.3 mg/kg, IV) and the hemodynamic response is determined. Thereafter, the animals are euthanized with sodium pentobarbital (150 mg/kg, IV).

MCh produces a decrease in mean arterial pressure (MAP) and decrease in heart rate (bradycardia). The peak decrease, from baseline, in MAP (depressor responses) is measured for each MCh challenge (before and after IH dosing). The effects of treatment on the MCh responses are expressed as % inhibition (mean+/−SEM) of the control depressor responses. Two-way ANOVA with the appropriate post-hoc test is used to test the effects of treatment and pre-treatment time. The depressor responses to MCh are expected to be relatively unchanged at 1.5 and 24 hours after inhalation dosing with vehicle. The ratio of the anti-depressor $ID_{50}$ to bronchoprotective $ID_{50}$ is used to compute apparent lung-selectivity of the test compound. Generally, compounds having an apparent lung-selectivity index greater than 5 are preferred. It is expected that the compounds of the invention will exhibit an apparent lung-selectivity index greater than 5, when tested in this or a similar assay.

While the present invention has been described with reference to specific aspects or embodiments thereof, it will be understood by those of ordinary skilled in the art that various changes can be made or equivalents can be substituted without departing from the true spirit and scope of the invention. Additionally, to the extent permitted by applicable patent statues and regulations, all publications, patents and patent applications cited herein are hereby incorporated by reference in their entirety to the same extent as if each document had been individually incorporated by reference herein.

What is claimed is:

1. A compound of formula Ic:

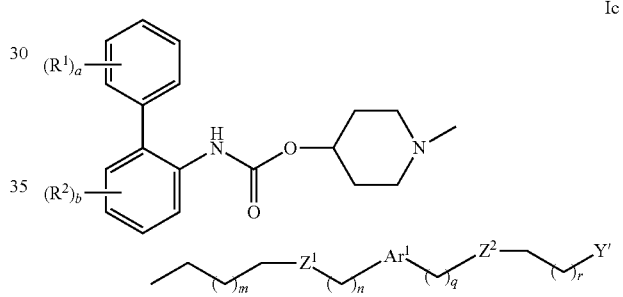

wherein:
a is 0 or 1; $R^1$ is halo;
b is 0 or 1; $R^2$ is halo;
m is 0 or 1;
$Z^1$ is selected from —C(O)N($R^4$)— and —N($R^4$)C(O)—, where $R^4$ is selected from hydrogen, (1-4C)alkyl, and (3-4C)cycloalkyl;
n is 0 or 1;
$Ar^1$ represents a phenylene group substituted with $(R^5)_p$ where p is 0 or an integer from 1 to 4 and each $R^5$ is independently selected from halo, hydroxy, (1-4C)alkyl, and (1-4C)alkoxy;
q is 0 or 1;
$Z^2$ is selected from —C(O)N($R^6$)— and —N($R^6$)C(O)—, where $R^6$ is selected from hydrogen, (1-4C)alkyl, and (3-4C)cycloalkyl;
r is 0, 1 or 2;
Y' is selected from

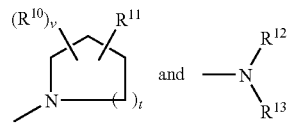

where:

t is 0 or an integer from 1 to 3; v is 0 or an integer from 1 to 4; each $R^{10}$ independently represents fluoro or (1-4C)alkyl; $R^{11}$ is selected from hydrogen, —OH, -(1-4C)alkyleneOH, —C(O)NR$^{11a}$R$^{11b}$, and —CH$_2$C(O)NR$^{11a}$R$^{11b}$, where R$^{11a}$ and R$^{11b}$ are independently selected from hydrogen, (1-4C)alkyl, hydroxy, (1-4C)alkoxy, (1-4C)alkyleneOR$^{11c}$, (3-6C)cycloalkyl, phenyl optionally substituted with hydroxy, and (1-4C)alkyleneC(O)NR$^{11d}$R$^{11e}$, where said (3-6C)cycloalkyl is unsubstituted or substituted with 1 or 2 (1-6C)alkyl or —NR$^{11d}$R$^{11e}$ groups, and where each of R$^{11c}$, R$^{11d}$ and R$^{11e}$ is independently hydrogen or (1-4C)alkyl; or R$^{11a}$ is taken together with R$^{11b}$ to form a 3-7 membered ring, optionally substituted with hydroxyl;

$R^{12}$ and $R^{13}$ are taken together to form a ring selected from piperazinone, morpholine, and piperazine; and said piperazine is substituted with (R$^{13c}$)$_w$ where w is 0 or an integer from 1 to 3 and each R$^{13c}$ is independently selected from (1-4C)alkyl, phenyl, and benzyl, optionally substituted with 1 to 5 fluoro substituents, or two R$^{13c}$ groups are joined to form (1-3C)alkylene;

wherein each alkyl and alkoxy group in R$^5$ is optionally substituted with 1 to 5 fluoro substituents;

or a pharmaceutically acceptable salt or stereoisomer thereof.

2. The compound of claim 1, wherein a and b each represent 0.

3. The compound of claim 1, wherein m is 0.

4. The compound of claim 1, wherein $Z^1$ is —N(R$^4$)C(O)—, and R$^4$ is selected from hydrogen and (1-4C)alkyl.

5. The compound of claim 4, wherein $Z^2$ is —C(O)N(R$^6$)— or —N(R$^6$)C(O)—, and R$^6$ is hydrogen.

6. The compound of claim 1, wherein $Z^1$ is —C(O)N(R$^4$)—, and R$^4$ is hydrogen.

7. The compound of claim 6, wherein $Z^2$ is —C(O)N(R$^6$)— or —N(R$^6$)C(O)—, and R$^6$ is hydrogen.

8. The compound of claim 1, wherein n is 0.

9. The compound of claim 1, wherein Ar$^1$ represents phen-1,3-ylene.

10. The compound of claim 1, wherein q is 0.

11. The compound of claim 1, wherein r is 0 or 1.

12. The compound of claim 1, wherein Y' is —NR$^{12}$R$^{13}$.

13. The compound of claim 12, wherein R$^{12}$ and R$^{13}$ are taken together to form a piperazinone ring.

14. The compound of claim 1, wherein Y' is

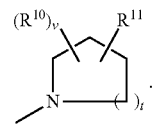

15. The compound of claim 14, wherein t is 1 or 2.

16. The compound of claim 14, wherein v is 0.

17. The compound of claim 14, wherein R$^{11}$ is selected from hydrogen, —OH, and —C(O)NR$^{11a}$R$^{11b}$, where R$^{11a}$ and R$^{11b}$ are hydrogen.

18. The compound of claim 1, selected from:

biphenyl-2-ylcarbamic acid 1-(2-{methyl-[3-(3-pyrrolidin-1-ylpropionylamino)benzoyl]amino}ethyl)piperidin-4-yl ester;

biphenyl-2-ylcarbamic acid 1-{2-[3-(3-pyrrolidin-1-ylpropionylamino)benzoylamino]ethyl}piperidin-4-yl ester;

biphenyl-2-ylcarbamic acid 1-[2-({3-[3-(4-carbamoylpiperidin-1-yl)propionylamino]benzoyl}methylamino)ethyl]piperidin-4-yl ester;

biphenyl-2-ylcarbamic acid 1-(2-{3-[3-(4-carbamoylpiperidin-1-yl)propionylamino]benzoylamino}ethyl)piperidin-4-yl ester;

biphenyl-2-ylcarbamic acid 1-(2-{methyl[3-(2-pyrrolidin-1-yl-acetylamino)benzoyl]amino}ethyl)piperidin-4-yl ester;

biphenyl-2-ylcarbamic acid 1-[2-({3-[2-(4-hydroxypiperidin-1-yl)acetylamino]benzoyl}methylamino)ethyl]piperidin-4-yl ester;

biphenyl-2-ylcarbamic acid 1-{2-[3-(2-pyrrolidin-1-ylacetylamino)benzoylamino]ethyl}piperidin-4-yl ester;

biphenyl-2-ylcarbamic acid 1-(2-{3-[2-(4-hydroxypiperidin-1-yl)acetylamino]benzoylamino}ethyl)piperidin-4-yl ester;

biphenyl-2-ylcarbamic acid 1-(2-{3-[2-(4-carbamoylpiperidin-1-yl)acetylamino]benzoylamino}ethyl)piperidin-4-yl ester; and biphenyl-2-ylcarbamic acid 1-[2-(methyl-{3-[2-(3-oxopiperazin-1-yl)acetylamino]benzoyl}amino)ethyl]piperidin-4-yl ester;

or a pharmaceutically acceptable salt thereof.

19. A pharmaceutical composition comprising a pharmaceutically acceptable carrier and the compound of claim 1.

20. A compound of formula Ic:

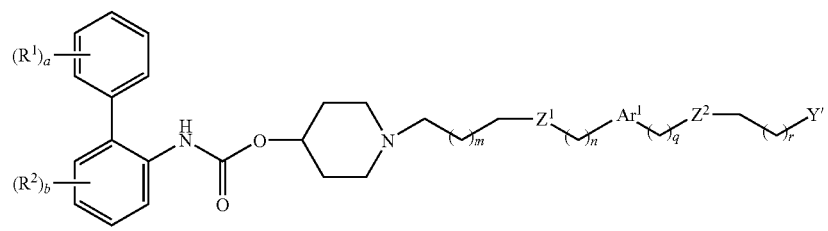

or a pharmaceutically acceptable salt or stereoisomer thereof, prepared by the process comprising:

(a) reacting a compound of formula II:

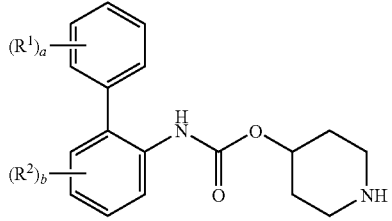

II or a salt thereof, with a compound of formula III:

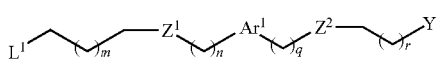

III wherein $L^1$ represents a leaving group; or (b) coupling a compound of formula IVa:

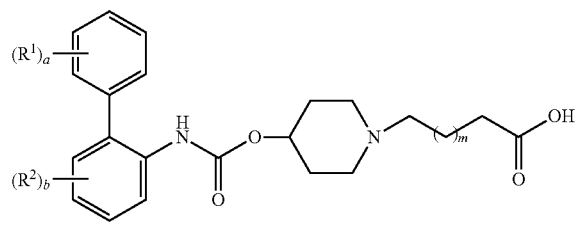

IVa with a compound of formula Va:

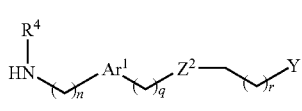

Va or (b') coupling a compound of formula IVb:

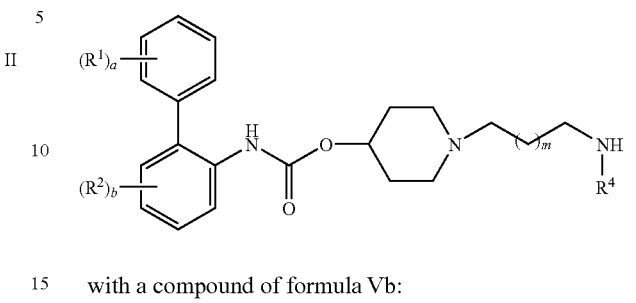

IVb with a compound of formula Vb:

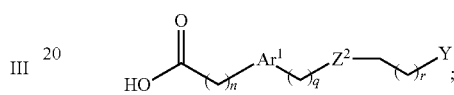

Vb or
(c) coupling a compound of formula VIa:

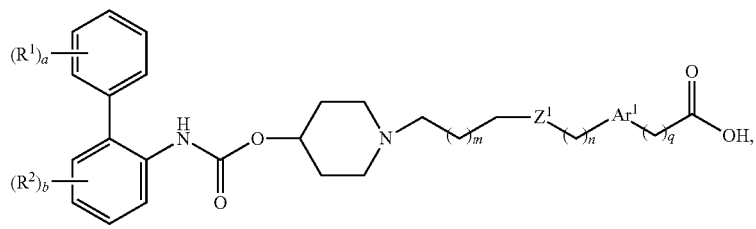

VIa with a compound of formula VIIa:

VIIa or (c') coupling a compound of formula VIb:

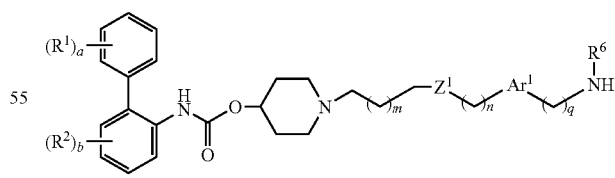

VIb with a compound of formula VIIb:

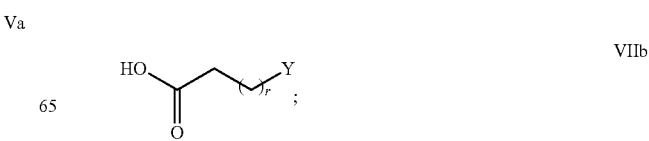

VIIb or
(d) reacting a compound of formula VIII:

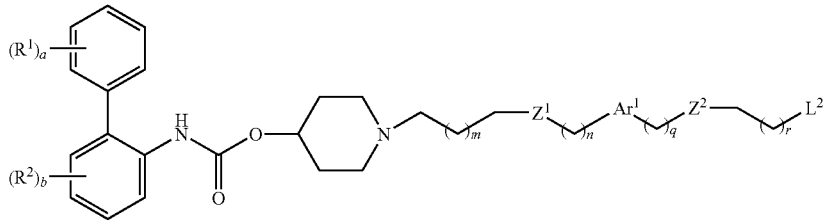

VIII wherein L² represents a leaving group, with a compound of formula IX:

H—Y  IX or
(e) reacting a compound of formula II with a compound of formula X:

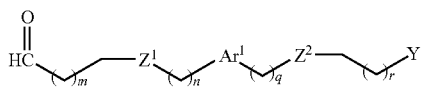

X in the presence of a reducing agent; or
(f) reacting a compound of formula XI:

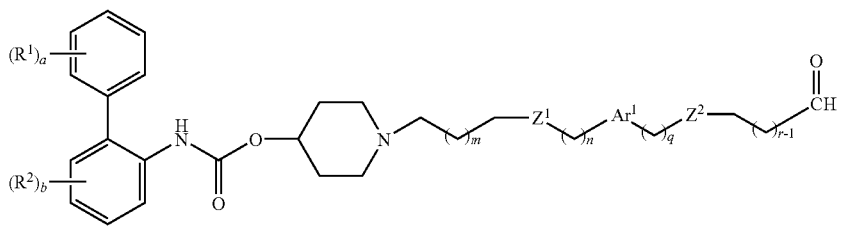

XI with a compound of formula IX in the presence of a reducing agent; and then
(g) removing any protecting groups that may be present to provide a compound of formula Ic; and
(h) optionally forming a pharmaceutically acceptable salt of the compound of formula Ic;
wherein:
a is 0 or 1; $R^1$ is halo;
b is 0 or 1; $R^2$ is halo;
m is 0 or 1;
$Z^1$ is selected from —C(O)N($R^4$)— and —N($R^4$)C(O)—, where $R^4$ is selected from hydrogen, (1-4C)alkyl, and (3-4C)cycloalkyl;
n is 0 or 1;
$Ar^1$ represents a phenylene group substituted with $(R^5)_p$ where p is 0 or an integer from 1 to 4 and each $R^5$ is independently selected from halo, hydroxy, (1-4C)alkyl, and (1-4C)alkoxy;
q is 0 or 1;
$Z^2$ is selected from —C(O)N($R^6$)— and —N($R^6$)C(O)—, where $R^6$ is selected from hydrogen, (1-4C)alkyl, and (3-4C)cycloalkyl;

r is 0, 1 or 2;
Y' is selected from

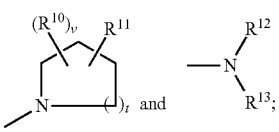

t is 0 or an integer from 1 to 3; v is 0 or an integer from 1 to 4; each $R^{10}$ independently represents fluoro or (1-4C)alkyl; $R^{11}$ is selected from hydrogen, —OH, -(1-4C)alkyleneOH, —C(O)NR$^{11a}$R$^{11b}$, and —CH$_2$C(O)NR$^{11a}$R$^{11b}$, where R$^{11a}$ and R$^{11b}$ are independently selected from hydrogen, (1-4C)alkyl, hydroxy, (1-4C)alkoxy, (1-4C)alkyleneOR$^{11c}$, (3-6C)cycloalkyl, phenyl optionally substituted with hydroxy, and (1-4C)alkyleneC(O)NR$^{11d}$R$^{11e}$, where said (3-6C)cycloalkyl is unsubstituted or substituted with 1 or 2 (1-6C)alkyl or —NR$^{11d}$R$^{11e}$ groups, and where each of R$^{11c}$, R$^{11d}$ and R$^{11e}$ is independently hydrogen or (1-4C)alkyl; or R$^{11a}$ is taken together with R$^{11b}$ to form a 3-7 membered ring, optionally substituted with hydroxyl;
$R^{12}$ and $R^{13}$ are taken together to form a ring selected from piperazinone, morpholine, and piperazine; and said piperazine is substituted with (R$^{13c}$), where w is 0 or an integer from 1 to 3 and each R$^{13c}$ is independently selected from (1-4C)alkyl, phenyl or benzyl, optionally substituted with 1 to 5 fluoro substituents, or two R$^{13c}$ groups are joined to form (1-3C)alkylene; and
wherein each alkyl and alkoxy group in $R^5$ is optionally substituted with 1 to 5 fluoro substituents.

* * * * *

UNITED STATES PATENT AND TRADEMARK OFFICE
CERTIFICATE OF CORRECTION

PATENT NO. : 8,133,905 B2
APPLICATION NO. : 12/640869
DATED : March 13, 2012
INVENTOR(S) : YongQi Mu et al.

It is certified that error appears in the above-identified patent and that said Letters Patent is hereby corrected as shown below:

At Column 104, line 58:

"$(R^{13c})$," should read "$(R^{13c})_w$".

Signed and Sealed this
Twelfth Day of June, 2012

David J. Kappos
*Director of the United States Patent and Trademark Office*